United States Patent
Arora et al.

(10) Patent No.: US 11,969,324 B2
(45) Date of Patent: Apr. 30, 2024

(54) ABSORBENT ARTICLE WITH IMPROVED PERFORMANCE

(71) Applicant: The Procter & Gamble Company, Cincinnati, OH (US)

(72) Inventors: Kelyn Anne Arora, Cincinnati, OH (US); Gerard A. Viens, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 309 days.

(21) Appl. No.: 17/490,312

(22) Filed: Sep. 30, 2021

(65) Prior Publication Data

US 2022/0104974 A1 Apr. 7, 2022

Related U.S. Application Data

(60) Provisional application No. 63/086,701, filed on Oct. 2, 2020.

(51) Int. Cl.
*A61F 13/511* (2006.01)
*A61F 13/49* (2006.01)
(Continued)

(52) U.S. Cl.
CPC .. *A61F 13/51121* (2013.01); *A61F 13/49007* (2013.01); *A61F 13/513* (2013.01);
(Continued)

(58) Field of Classification Search
CPC .............. A61F 13/513; A61F 13/51113; A61F 13/537; A61F 13/53717; A61F 13/5376;
(Continued)

(56) References Cited

U.S. PATENT DOCUMENTS

2007/0026753 A1* 2/2007 Neely .................. A61F 13/513
442/361
2014/0343523 A1 11/2014 Viens
(Continued)

FOREIGN PATENT DOCUMENTS

CA 3101871 A1 12/2019

OTHER PUBLICATIONS

PCT Search Report and Written Opinion for PCT/US2021/052820 dated Feb. 4, 2022, 13 pages.

*Primary Examiner* — Catharine L Anderson
*Assistant Examiner* — Lynne Anderson
(74) *Attorney, Agent, or Firm* — Sarah M. DeCristofaro; William E. Gallagher

(57) ABSTRACT

An absorbent article having a nonwoven topsheet, a backsheet, an absorbent core disposed therebetween, and a fluid management layer disposed between the topsheet and the absorbent core is disclosed. The fluid management layer is an integrated nonwoven material having a basis weight in a range of from 40 gsm to 75 gsm and has 10 percent to about 60 percent by weight of absorbent fibers, from between about 15 percent to about 70 percent of resilient fibers, and from between about 25 percent to about 70 percent stiffening fibers. The absorbent article exhibits a third dose acquisition time of less than 10 seconds, more preferably less than 8 seconds, and most preferably less than 7 seconds, and a Rewet of no greater than 0.40 g, more preferably less than about 0.3 grams, or most preferably less than about 0.2 grams.

17 Claims, 29 Drawing Sheets

(51) Int. Cl.
*A61F 13/513* (2006.01)
*A61F 13/537* (2006.01)
*A61F 13/539* (2006.01)
*A61F 13/15* (2006.01)
*A61F 13/51* (2006.01)
*A61F 13/53* (2006.01)

(52) U.S. Cl.
CPC .......... *A61F 13/537* (2013.01); *A61F 13/539* (2013.01); *A61F 2013/15959* (2013.01); *A61F 2013/15967* (2013.01); *A61F 2013/51066* (2013.01); *A61F 2013/51178* (2013.01); *A61F 2013/51366* (2013.01); *A61F 2013/530781* (2013.01)

(58) Field of Classification Search
CPC .. A61F 2013/15373; A61F 2013/15406; A61F 2013/15447; A61F 2013/51066
See application file for complete search history.

(56) References Cited

U.S. PATENT DOCUMENTS

| | | | |
|---|---|---|---|
| 2018/0098889 A1* | 4/2018 | Hardie | A61F 13/537 |
| 2018/0098893 A1 | 4/2018 | Viens | |
| 2018/0168893 A1* | 6/2018 | Ashraf | D04H 3/147 |
| 2020/0306105 A1 | 10/2020 | Peri et al. | |

* cited by examiner

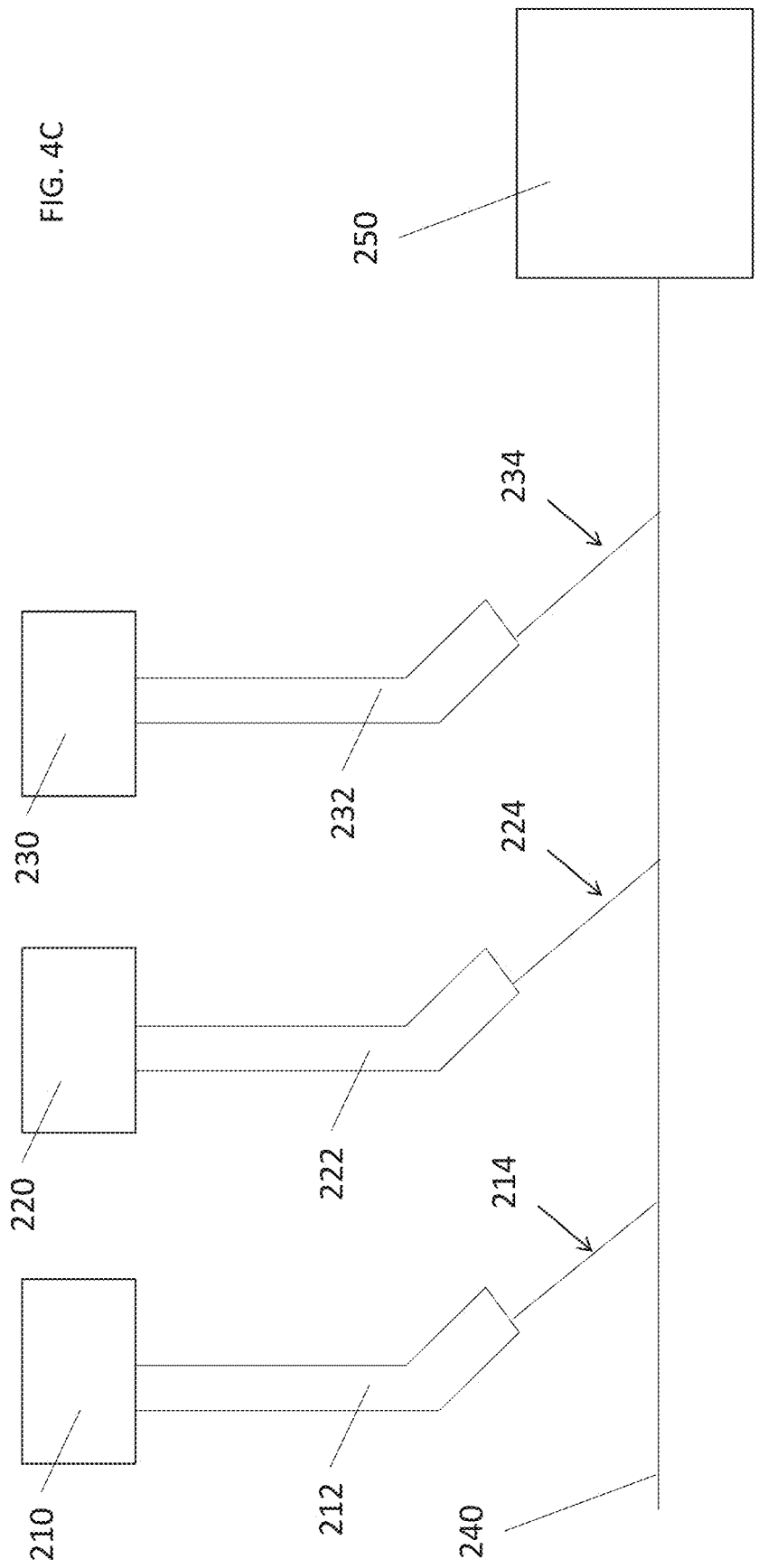

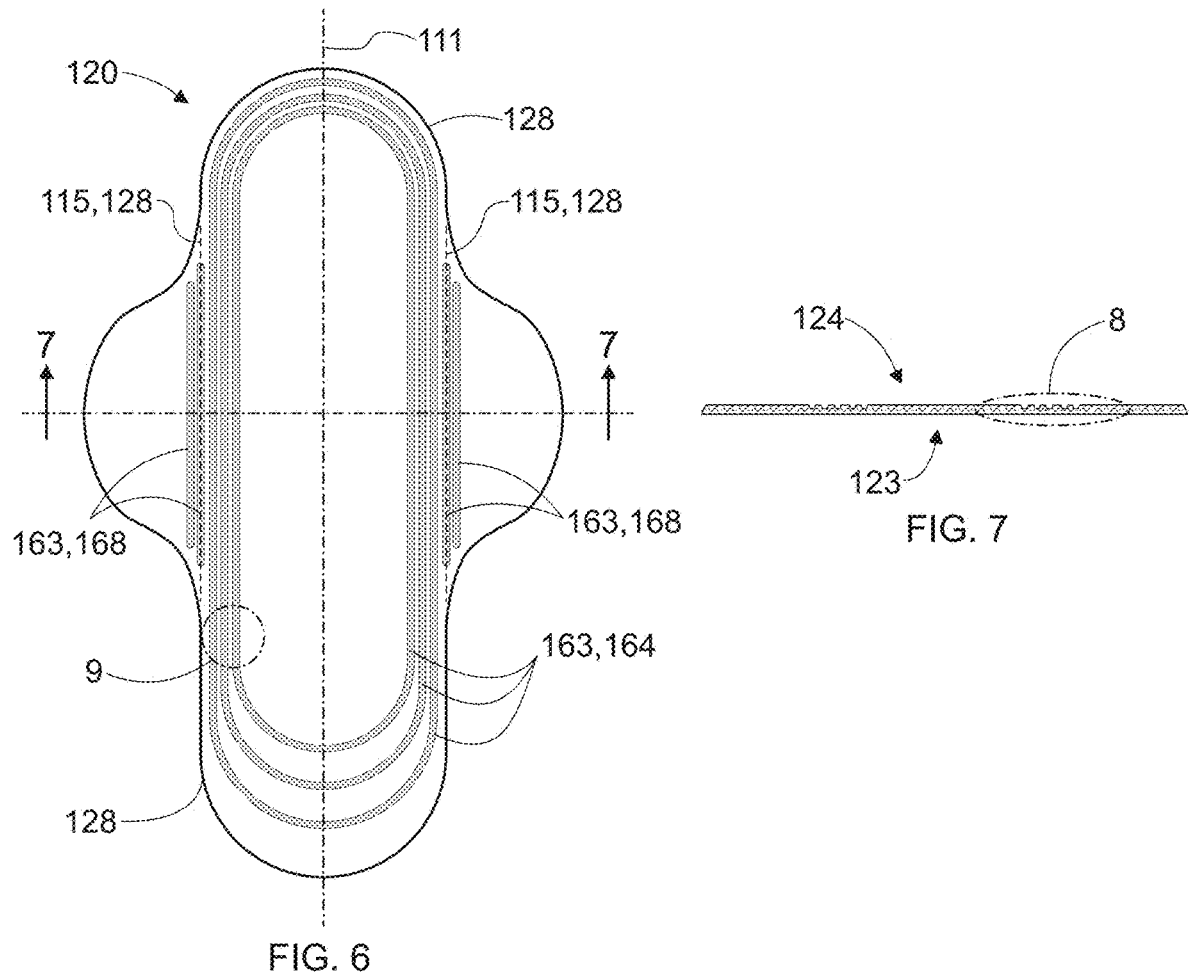
FIG. 6
FIG. 7
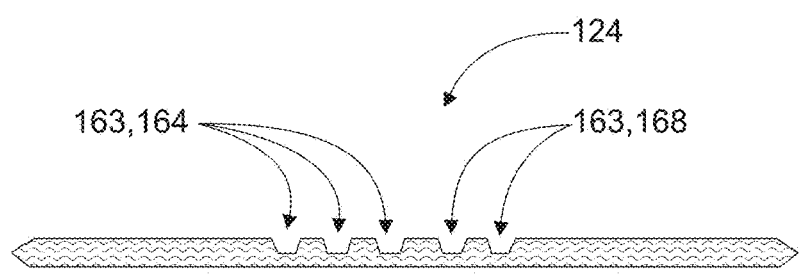
FIG. 8

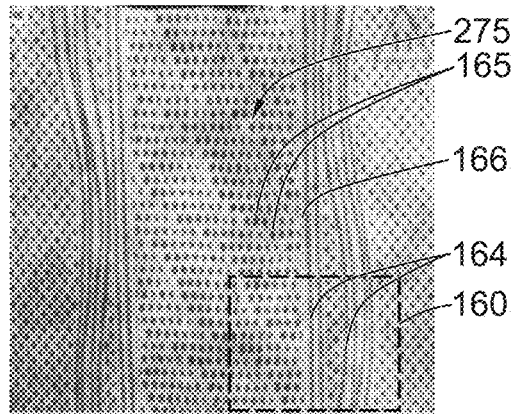
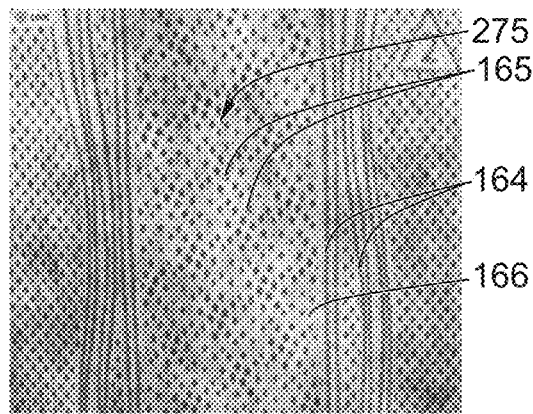
FIG. 26A
FIG. 26B
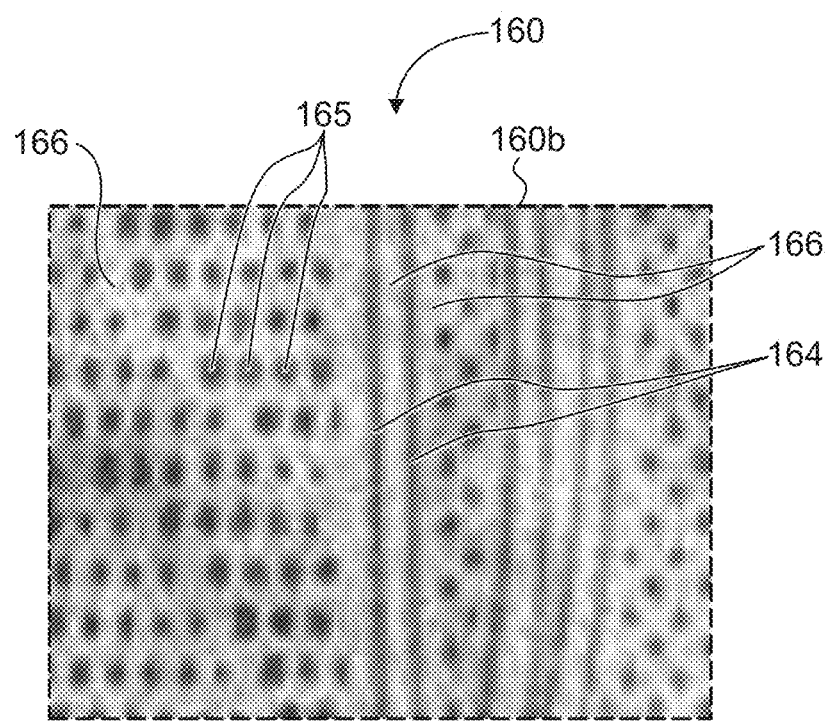
FIG. 27

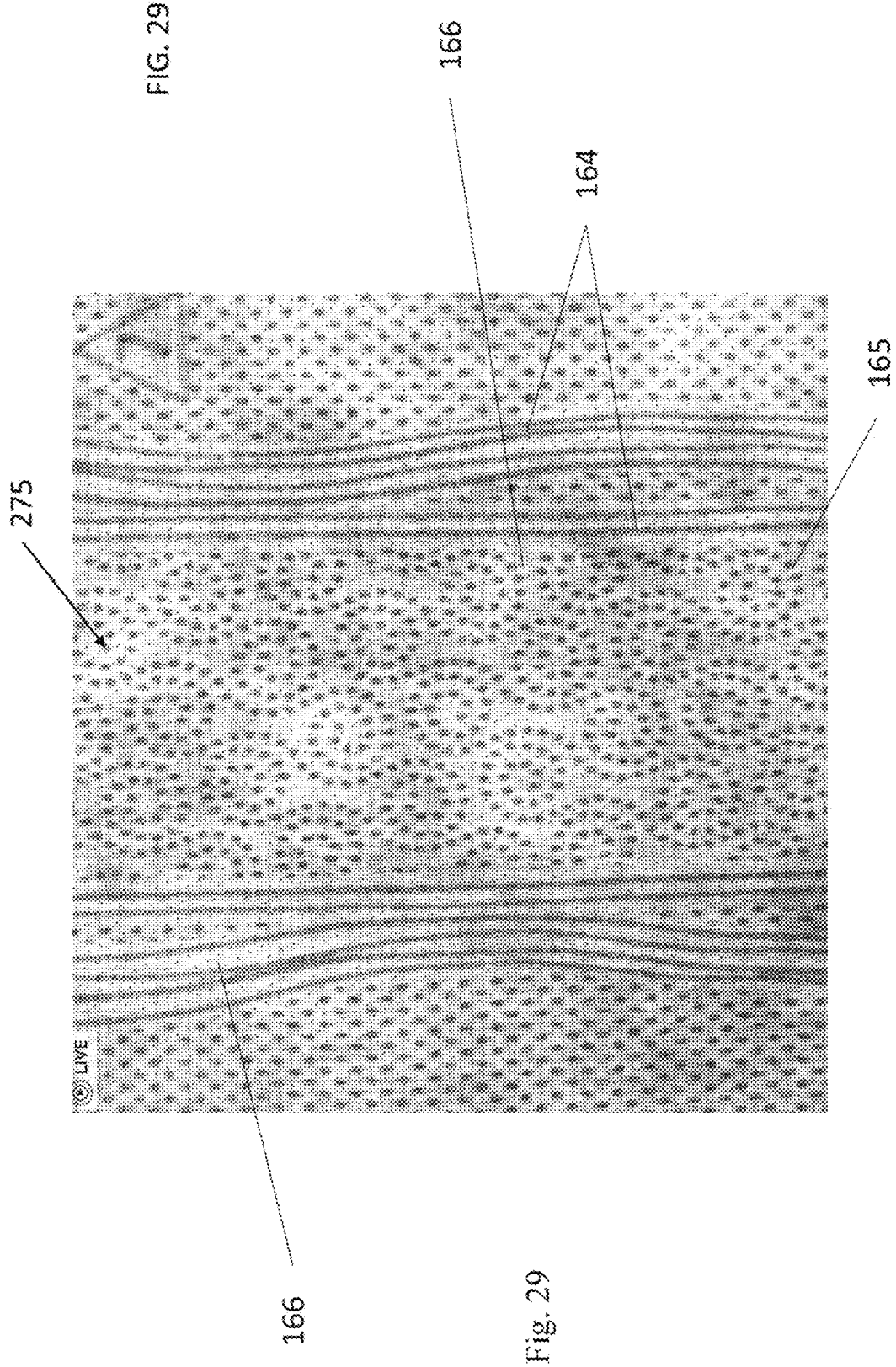

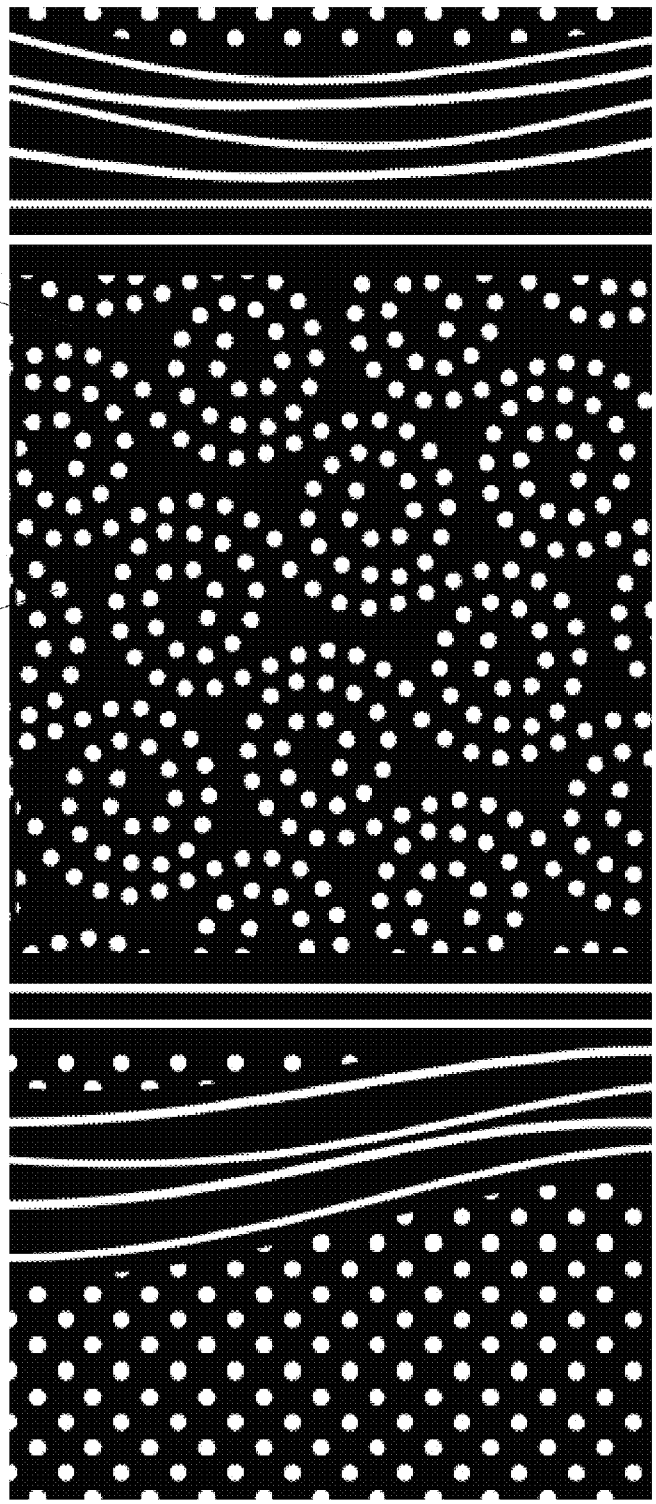

ABSORBENT ARTICLE WITH IMPROVED PERFORMANCE

CROSS REFERENCE TO RELATED APPLICATION

This application claims the benefit of U.S. Provisional Application No. 63/086,701, filed Oct. 2, 2020, the substance of which is incorporated herein by reference.

FIELD OF THE INVENTION

The present disclose relates to disposable absorbent articles such as feminine hygiene pads, and particularly articles and pads having topsheets having structural features formed therein.

BACKGROUND OF THE INVENTION

Wearable disposable absorbent articles such as feminine hygiene pads, adult incontinence pads and disposable diapers typically include a topsheet of material adapted to serve as the wearer-facing outer layer of an envelope structure that contains absorbent material. Typically the topsheet is adapted to be liquid permeable such that liquid body exudates may pass therethrough, to reach the absorbent material contained in the envelope structure and be absorbed and retained by the absorbent material until the time the article is removed and discarded. Generally it is desired that the topsheet serve to readily receive aqueous fluid such as urine or menstrual fluid, conduct the fluid in a z-direction therethrough, and release or desorb it to an absorbent structure disposed adjacently beneath the topsheet.

For combined purposes of cost effectiveness, wearer comfort and functionality, topsheets of many currently-marketed absorbent articles are made of nonwoven web material formed in some portion, or entirely, of filaments spun from polymer resins. Through a number of technologies currently known, various types of nonwovens may be manufactured to have sufficient liquid permeability, suitably soft feel to the skin, and mechanical strength making them suitable for forming topsheets. Nonwoven web materials ("nonwovens") may be formed of synthetic fibers, such as but not limited to fibers spun from polyolefins, polyesters, polyamides, etc., or combinations thereof. Nonwovens may be formed using various processes that form a cohesive fabric-like web in which the fibers are "continuous" (of relatively long, variable and indefinite lengths) or staple fibers (fibers cut into relatively short and substantially uniform lengths).

Various attempts have been made to make nonwovens used to form topsheets of absorbent articles. Unfortunately, currently available absorbent articles with nonwoven topsheets have left room for improvement in providing for rapid acceptance and movement of fluid down into the absorbent structure following discharge, avoidance of fluid retention in the topsheet, and rewetting. As such, there is a need for absorbent articles which have improved performance from an acquisition and rewet perspective.

BRIEF DESCRIPTION OF THE DRAWINGS

FIG. 4C is a schematic representation of a process for making fluid management layers of the present disclosure.

FIG. 6 is a plan view of an example of a topsheet for an absorbent article in the form of a feminine hygiene pad.

FIG. 7 is a schematic lateral cross section of the topsheet of FIG. 6, taken along a lateral axis.

FIG. 8 is an expanded schematic view of the portion of the cross section identified as "8" in FIG. 7.

FIGS. 26A and 26B are grayscale reproductions of photographs of samples of nonwoven web material having discrete low bulk portions, channel portions and built-up regions.

FIG. 27 is an enlarged view of the zone 160 identified in FIG. 26A.

FIG. 29 is a grayscale reproduction of photographs of samples of nonwoven web material constructed in accordance with the present disclosure.

FIG. 30 is an image of a portion of a mask used to produce a forming belt used to make the nonwoven web material of FIG. 29.

DESCRIPTION OF EXAMPLES

Definitions

Figure 1:
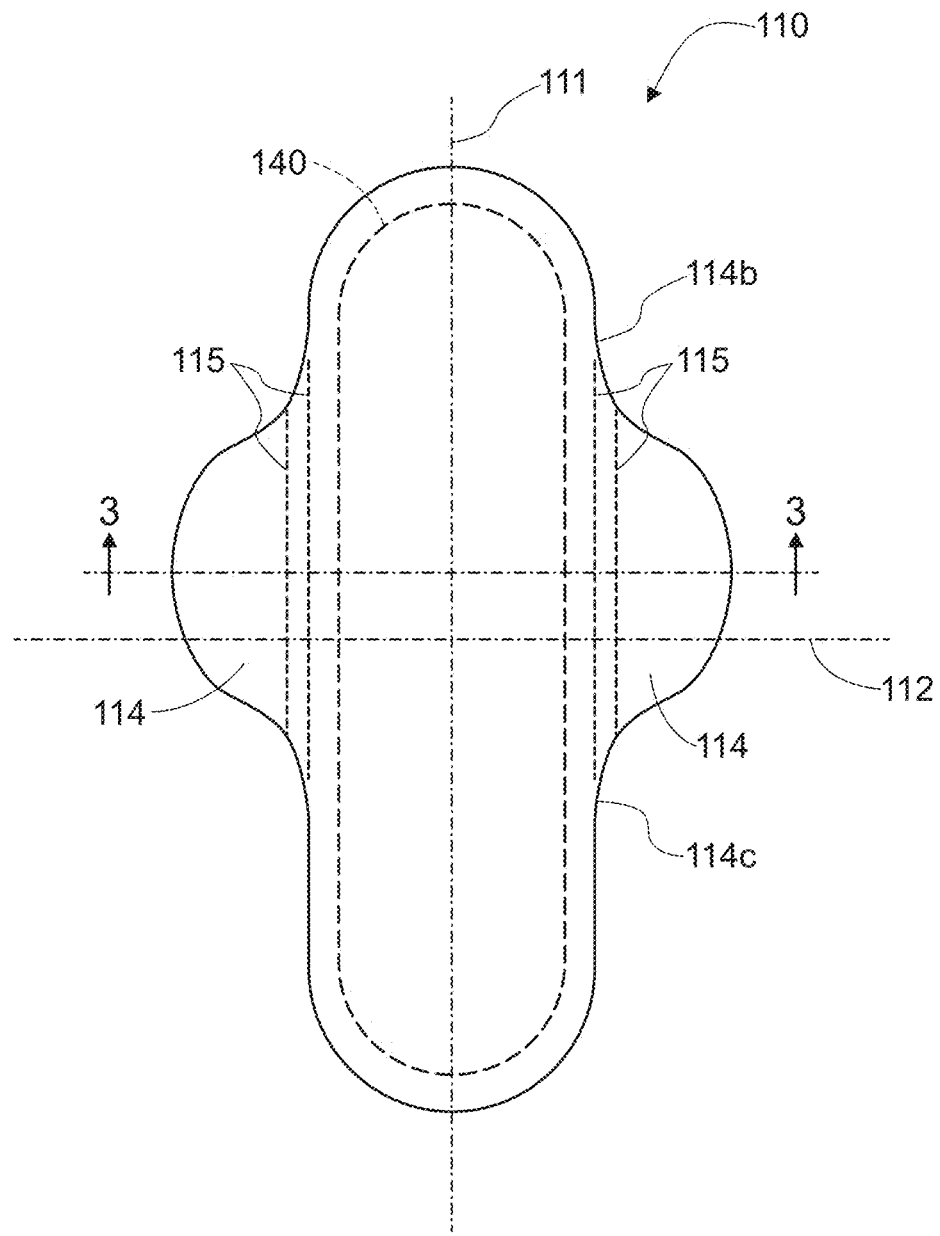
FIG. 1 is a plan view of an example of an absorbent article in the form of a feminine hygiene pad.
Figure 2:
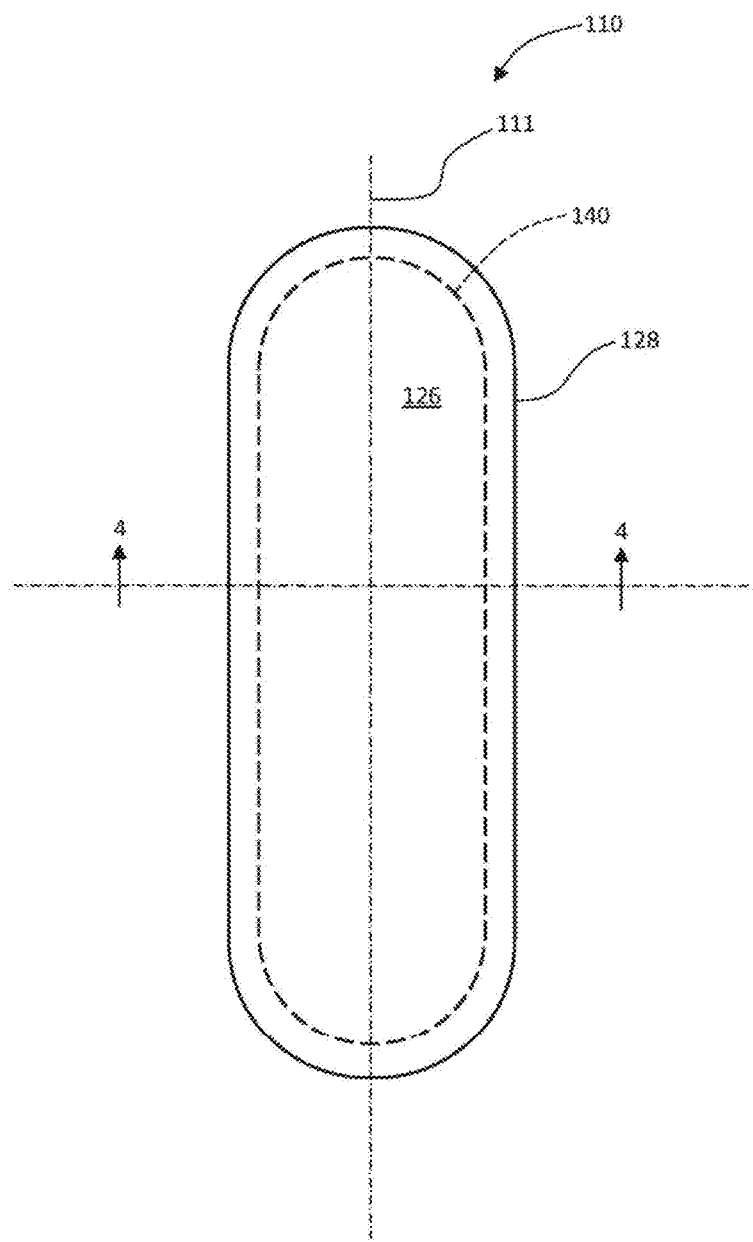
FIG. 2 is a plan view of the pad of FIG. 1, shown with wing portions turned under and thereby depicting an in-use wear-facing portion.

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments (e.g., liners, pads and briefs) and/or feminine hygiene products.

With respect to a nonwoven web material formed partially or entirely of fibers and/or filaments, a "bond" is a three-dimensional zone within the material in which a plurality of the filaments are held together in a unitary mass created by one or a combination of a deposit of adhesive applied to the material, thermal fusing caused by localized application of heating energy to the material (for example, heat from defined bonding protrusions on a heated bonding roller, or ultrasonic vibratory energy from a sonotrode in combination with a bonding roller with defined bonding protrusions), or plastic deformation and entanglement or intermeshing caused by localized application of pressure (for example, by a bonding roller with defined bonding protrusions) to the material in the z-direction. A bond has a two-dimensional profile along the x-y plane approximated by the large surfaces of the web material, as well as a z-direction dimension. When bonds are created via use of a bonding roller with defined bonding protrusions, the two-dimensional profiles of the bonds will approximately reflect the shape(s) of the bonding protrusions.

"Fiber" as used herein means an elongate particulate having a length less than 5.08 cm (2 in.). In the field of nonwoven web manufacturing, fibers are typically considered discontinuous in nature. Non-limiting examples of fibers include natural fibers such as wood pulp, cotton and bamboo fibers, and synthetic staple fibers (which may be manufactured by chopping filaments) such as polypropylene, polyethylene, polyester, copolymers thereof, rayon, lyocell, glass fibers and polyvinyl alcohol fibers.

"Filament" as used herein means an elongate particulate having a length equal to or greater than 5.08 cm (2 in.). In the field of nonwoven web manufacturing, filaments are typically considered to be of indefinite length and/or be substantially continuous in nature with respect to nonwoven web materials in which they appear, in contrast to fibers, it being recognized that they cannot be of infinite length. Non-limiting examples of filaments include meltblown and/or spunbond filaments. Non-limiting examples of polymers that may be spun into filaments include natural polymers, such as starch, starch derivatives, cellulose, such as rayon and/or lyocell, and cellulose derivatives, hemicellulose, hemicellulose derivatives, and synthetic polymers including, but not limited topolyvinyl alcohol filaments and/or polyvinyl alcohol derivative filaments, and thermoplastic polymers such as polyesters, nylons, polyolefins such as polypropylene, polyethylene, and copolymers thereof, and biodegradable or compostable thermoplastics such as polylactic acid, polyhydroxyalkanoate, polyesteramide, and polycaprolactone; bio-sourced or bi-derived polymers (such as but not limited to bio-sourced polyethylene); and recycled polymeric materials (such as but not limited to recycled PET). Spun filaments may be monocomponent or multicomponent, for example, bicomponent.

The "region basis weight" of a region of a section of formed nonwoven web material means the weight in grams of the region of interest, divided by its surface area on one side, measured by any appropriate measurement technique including but not necessarily limited to the Localized Basis Weight measurement method described herein.

"Intensive properties" of a region of a nonwoven web material include basis weight; aggregate total of the lengths of all fibers and/or filaments present per unit surface area of the material lying along an x-y plane (referred to herein as fiber and/or filament "area density"); caliper/thickness in the z-direction; and density (mass per unit volume).

"Lateral," with respect to a feminine hygiene pad, adult incontinence pad, or disposable diaper, refers to the direction perpendicular to the longitudinal direction, and from side-to-side of the article from the wearer's perspective.

"Longitudinal," with respect to a feminine hygiene pad, adult incontinence pad, or disposable diaper, refers to the direction from front-to-rear or from rear-to-front of the article from the wearer's perspective.

"Nonwoven," with respect to a fabric of web of material, means a fabric or web formed predominately of fibers, filaments or a combination thereof, which are not knitted or woven, but rather are laid down and accumulated into a batt and then consolidated and held together in a coherent fabric web of material by entangling, a dispersed binding agent, a pattern of discrete bonds formed by localized deposits of adhesive, localized thermal fusing, localized plastic deformation and entanglement between fibers or filaments caused by localized applications of pressure, or a combination thereof.

The term "integrated" as used herein is used to describe fibers of a nonwoven material which have been intertwined, entangled, and/or pushed/pulled in a positive and/or negative Z-direction (direction of the thickness of the nonwoven material). Some exemplary processes for integrating fibers of a nonwoven web include spunlacing and needlepunching. Spunlacing uses a plurality of high pressure water jets to entangle fibers. Needlepunching involves the use of needles to push and/or pull fibers to entangle them with other fibers in the nonwoven.

The term "carded" as used herein is used to describe structural features of the fluid management layers described herein. A carded nonwoven utilizes fibers which are cut to a specific length, otherwise known as "staple length fibers." Staple length fibers may be any suitable length. For example, staple length fibers may have a length of up to 120 mm or may have a length as short as 10 mm. However, if a particular group of fibers are staple length fibers, for example viscose fibers, then the length of each of the viscose fibers in the carded nonwoven is predominantly the same, i.e. the staple length. It is worth noting that where additional staple fiber length fiber types are included, for example, polypropylene fibers, the length of each of the polypropylene fibers in the carded nonwoven is also predominantly the same. But, the staple length of the viscose and the staple length of the polypropylene may be different.

In contrast, continuous filaments such as by spunbonding or meltblowing processes, do not create staple length fibers. Instead, these filaments are of an indeterminate length and are not cut to a specific length as noted regarding their staple fiber length counterparts.

"Ordered arrangement," with respect to a section of formed nonwoven web material having a regular (repeating) pattern or configuration of zones that each include adjacent regions of differing intensive properties, or an irregular (non-repeating) pattern or configuration of zones that each include adjacent regions of differing intensive properties, along a surface of the material, means an arrangement of such zones that is recognizable by a person of ordinary skill in the art of nonwoven web manufacturing as an ordered, non-random arrangement or pattern, as contrasted with a random, unordered accumulation and distribution of filaments and/or fibers. As will be recognized by persons of ordinary skill in the art relevant to this disclosure, an ordered arrangement of such zones will result from process steps and equipment used to manufacture the nonwoven web material, configured to repeatably effect the ordered arrangement in the nonwoven web material. An ordered arrangement of zones in a nonwoven web material may reflect an ordered arrangement of features of forming equipment, such as an ordered arrangement of features on a forming belt.

"Visually discernible" means visible and visually detectable from a distance of approximately 0.5 meter or more, to the naked eye of an ordinary observer having 20/20 vision, under indoor office lighting conditions deemed appropriate for reading printed text media. A "zone" is a zone of a nonwoven web material comprising at least first and second adjacent regions thereof, the first and second adjacent regions having differences in one or a combination of basis weight, caliper, density (mass/volume), and/or fiber and/or filament area density.

A "region" is a sub-portion of a "zone", defined by and distinguished from other sub-portions of the zone by one or a combination of a difference in basis weight, caliper, density (mass/volume), and/or fiber and/or filament area density.

An ordered arrangement of "attenuated regions" of relatively low basis weight in a nonwoven material, wherein filaments are present in relatively low numbers, is distinguishable from an ordered arrangement of apertures or holes through a nonwoven material, in that "attenuated regions" in an ordered arrangement have randomly and varyingly located and varyingly oriented filaments passing thereacross between portions of an adjacent built-up region(s) of relatively higher basis weight, whereas apertures or holes in an ordered arrangement will have an identifiable, consistent absence of filaments passing thereacross between neighboring unapertured portions.

A "discrete" low bulk portion or "discrete" attenuated region means one that is entirely surrounded (in an x-y plane) by a continuous area of built-up region, and has a largest dimension in the x-y plane no greater than 1 cm.

"z-direction," with respect to a nonwoven web material or portion thereof lying along an x-y plane, means the direction orthogonal to the x-y plane. "z-direction," with respect to a forming belt used to manufacture a nonwoven web material moving through a working location of belt travel lying along an x-y plane, means the direction orthogonal to the x-y plane.

"Liquid-permeable" and "liquid-impermeable" refer to the penetrability of materials in the context of the intended usage of disposable absorbent articles. Specifically, the term "liquid-permeable" refers to a layer or a layered structure having pores, openings, and/or interconnected void spaces that permit aqueous liquid such as water, urine, or synthetic urine to pass through its thickness in the absence of a forcing pressure. Conversely, the term "liquid-impermeable" refers to a layer or a layered structure through the thickness of which aqueous liquid such as water, urine, or synthetic urine cannot pass in the absence of a forcing pressure (aside from natural forces such as gravity). A layer or a layered structure that is liquid-impermeable according to this definition may be permeable to liquid vapor, i.e., may be "vapor-permeable."

With respect to a component of a wearable absorbent article constructed of a plurality of components, a "wearer-facing" component is the component disposed closest to the wearer's skin when the article is worn, and an "outward-facing" component is the component disposed furthest from the wearer's skin. With respect to two opposing major surfaces of a web, sheet or batt component of a wearable absorbent article, the "wearer-facing" surface is the surface facing the wearer's skin when the article is worn, and the opposing "outward-facing" surface is the surface facing away from the wearer's skin.

Absorbent Articles

Referring to FIGS. 1-4B, an absorbent article may have the form of a feminine hygiene pad 110. Pad 110 has a longitudinal axis 111 and a lateral axis 112 and may include a wearer-facing, liquid-permeable topsheet 120, outward-facing, liquid-impermeable backsheet 130, and an absorbent structure 140 disposed between and enveloped by the topsheet and backsheet. It will be recognized that adult incontinence pads, disposable absorbent pants and disposable diapers also may include this general structure.

Feminine hygiene pads 110 of the present disclosure may include wing portions such as depicted wing portions 114. Where the absorbent article is in the form of adult incontinence pads, they may similarly also include wing portions of similar positioning and configuration. Wing portions 114 may be portions of one or both of the topsheet and backsheet materials, without any substantial portion of the absorbent structure 140 or quantity of absorbent material between them, which extend laterally away from the longitudinal axis 111. Or the wing portions 114 may comprise discrete material which is attached to a portion of the topsheet and/or backsheet. Configurations regarding wings are discussed in additional detail in US Patent Application Publication No. 2018/0235819. Forms are also contemplated where the proximal edges of the layers of the cuffs are disposed on the backsheet and wherein one proximal edge is disposed more inboard than another of the proximal edges.

Figure 3A:
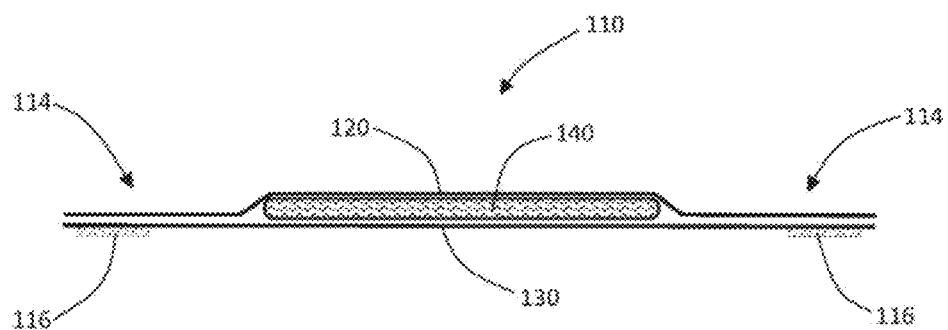
FIG. 3A is a schematic lateral cross section view of the pad of FIG. 1, taken along a lateral axis.
Figure 3B:
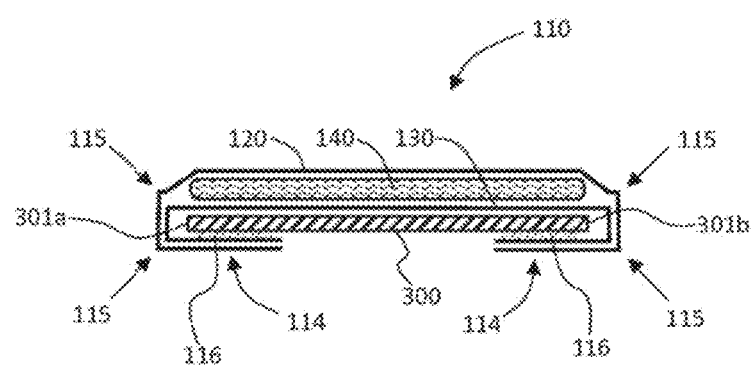
FIG. 3B is a schematic lateral cross section view of the pad with wing portions folded under as depicted in FIG. 2, taken along a lateral axis, shown associated with a crotch portion of a pair of underpants.

Referring to FIGS. 3A and 3B, wing portions 114 may be provided to allow the user to place the pad 110 inside the user's underpants over the crotch portion 300 thereof, and fold and wrap the wing portions 114 over the insides of the respective left and right leg opening edges 301a, 301b of the underpants, through the leg openings and about the outer surface of the underpants in the crotch region. Wing portions 114 may be provided with deposited patches of adhesive 116 to allow the user to adhere the wing portions 114 to the outer surface of the underpants in the crotch portion 300, helping hold the pad in place within the underpants during wear, and protecting the underpants about the leg opening edges from staining by exudates. When included and used for these purposes, wing portions 114 are required to flex and/or fold along approximately longitudinal wing fold lines 115 (see FIGS. 1 and 3B).

For purposes herein, a wing portion 114 of a feminine hygiene pad 110 may be identified as a portion that includes no substantial portion of the absorbent structure 140 and no substantial quantity of absorbent material therewithin, the portion having a profile that extends laterally away from the longitudinal axis 111 of the pad, beginning approximately at a forward inflection point 114b where the outer perimeter changes direction, away from a direction approximately parallel the longitudinal axis toward a direction perpendicular to the longitudinal axis, and ending approximately at a rearward inflection point 114c where the outer perimeter approaches the longitudinal axis and then changes direction away from a direction perpendicular the longitudinal axis, toward a direction to parallel to the longitudinal axis, where inflection points 114b, 114c are the two points along the perimeter that are closer to the longitudinal axis than any other points along the perimeter of the wing portion. See, e.g., FIG. 1. The wing portion may be substantially delineated from the main portion of the pad by a line connecting the two inflection points 114b, 114c.

When wing portions 114 of a pad 110 are folded for use as described above, the topsheet has an in-use wearer-facing surface 126 that does not include the wing portions 114. In-use wearer-facing surface 126 has an outer perimeter 128. In other types of pads and diapers, wing portions 114 may be omitted, in which circumstance the in-use wearer-facing surface 126 of the topsheet and the outer perimeter 128 may be coextensive. Various non-limiting examples of possible topsheets with in-use wearer-facing portions 126 and outer perimeters 128 thereof are illustrated in FIGS. 5A-5D. As suggested in FIGS. 5A, 5B and 5D, wing portions 114 with outer edges 114a may be included, or may be omitted, depending upon the style of article desired to be provided. As suggested in FIG. 5C, some types of wearable absorbent articles such as disposable diapers may have topsheets 120 with a simple rectangular shape.

Formed Topsheet Features

Referring now to FIGS. 6-10, a topsheet 120 for an absorbent article such as a feminine hygiene pad comprises a nonwoven material. The nonwoven material may be formed of a section of formed nonwoven web material imparted with certain features to enhance visual appearance and provide beneficial functionality. A topsheet 120 formed of a section of formed nonwoven web material may be provided with one or more attenuated regions 163 defining channel portions 164. Channel portions 164 may be disposed to the inside of, proximate to, and may approximately parallel, outer perimeter 128 of in-use wearer-facing portion. Although depicted as defining continuous oval- or stadium-shapes in FIG. 6, channel portions 164 may be discontinuous, and may be present only along the sides, only along the ends, or portions or intervals, of in-use wearer-facing portion 126 of topsheet 120 with outer perimeter 128.

For purposes of reducing the chances of exudate fluid migration across the topsheet to the edges thereof, it may be desired that the configuration of channel portion(s) 164 have certain features.

In some examples, it may be desired than any configuration of channel portion(s) 164 that is present, not have a portion that extends continuously along a path from an area proximate a discharge locus out to any edge of the topsheet. Avoiding inclusion of such a channel portion will avoid creating a channel for discharged fluid to migrate to an edge of the topsheet or in-use wearer-facing portion 126 thereof, with the attendant possibility of leakage of discharged fluid off the pad.

In non-limiting examples such as depicted in FIGS. 22 and 23A-23K, it may be desired that a configuration of channel portion(s) 164 be substantially symmetric about longitudinal axis 111 of the topsheet 120 and/or of the article 110. However asymmetric configurations of channel portion(s) 164, may also be utilized.

In some examples such as some types and/or sizes of feminine hygiene pads and baby diapers, it may be desired that a configuration of channel portion(s) 164 be longitudinally centered about a lateral discharge locus 112b that is offset from the lateral axis 112 of the article (as identified in FIG. 1), such that the configuration of channel portion(s) 164 is not longitudinally centered or symmetric about lateral axis 112.

For a feminine hygiene pad, for example, this configuration may be desired where it is preferred that the pad be placed within the user's underpants such that a greater proportion of absorbent structure surface area within the x-y plane be located rearward of the expected discharge locus 112b (which is the location on the article expected to first receive a discharge of fluid during normal use of the article, located along the longitudinal axis 111 and at the midpoint of the longitudinal dimension of the configuration of channel portion(s) 164). For example, for some types and sizes of feminine hygiene pads, it may be desired that the greater proportion of absorbent structure surface area be located to the rear of the expected discharge locus 112b on the topsheet (where the discharge locus 112b is the location on the topsheet expected to be most proximate the user's vaginal opening during use/wear). In such examples it may be preferred that the greater proportion of absorbent structure surface area be located rearward of the discharge locus because discharged menstrual fluid often moves rearward through a pad as a result of proximity of the pad to the user's body as held in place by underpants, anatomical features and typical ranges of body positions and movements during use/wear. When the configuration of channel portion(s) 164 is visually discernible when formed as described herein, its visible location may serve to guide the user in appropriately locating and placing the pad within the user's underpants for use/wear. In some examples, any wing portions 114 included may be approximately longitudinally centered about the lateral discharge locus 112b, as suggested by way of non-limiting example in FIG. 22.

In other examples, it may be desired that the configuration of channel portion(s) 164 be longitudinally centered about the lateral axis 112 of the article, and for some examples, be symmetric about the lateral axis 112. In such examples, the expected discharge locus may be at the intersection between the longitudinal axis 111 and lateral axis 112.

Figure 24A:
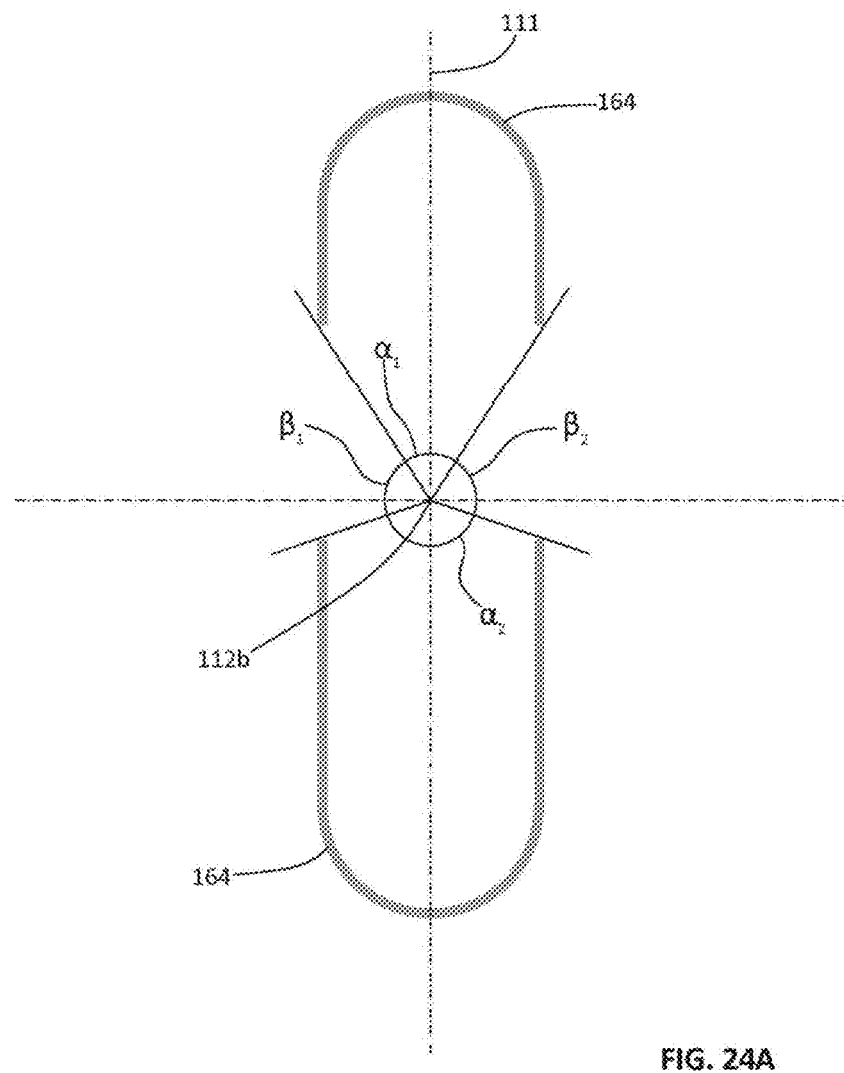
FIGS. 24A-24E are plan views of examples of configurations of channel portions for a topsheet, shown with geometric references for determining whether the configurations predominately circumscribe a discharge locus on the topsheet.
Figure 24B:
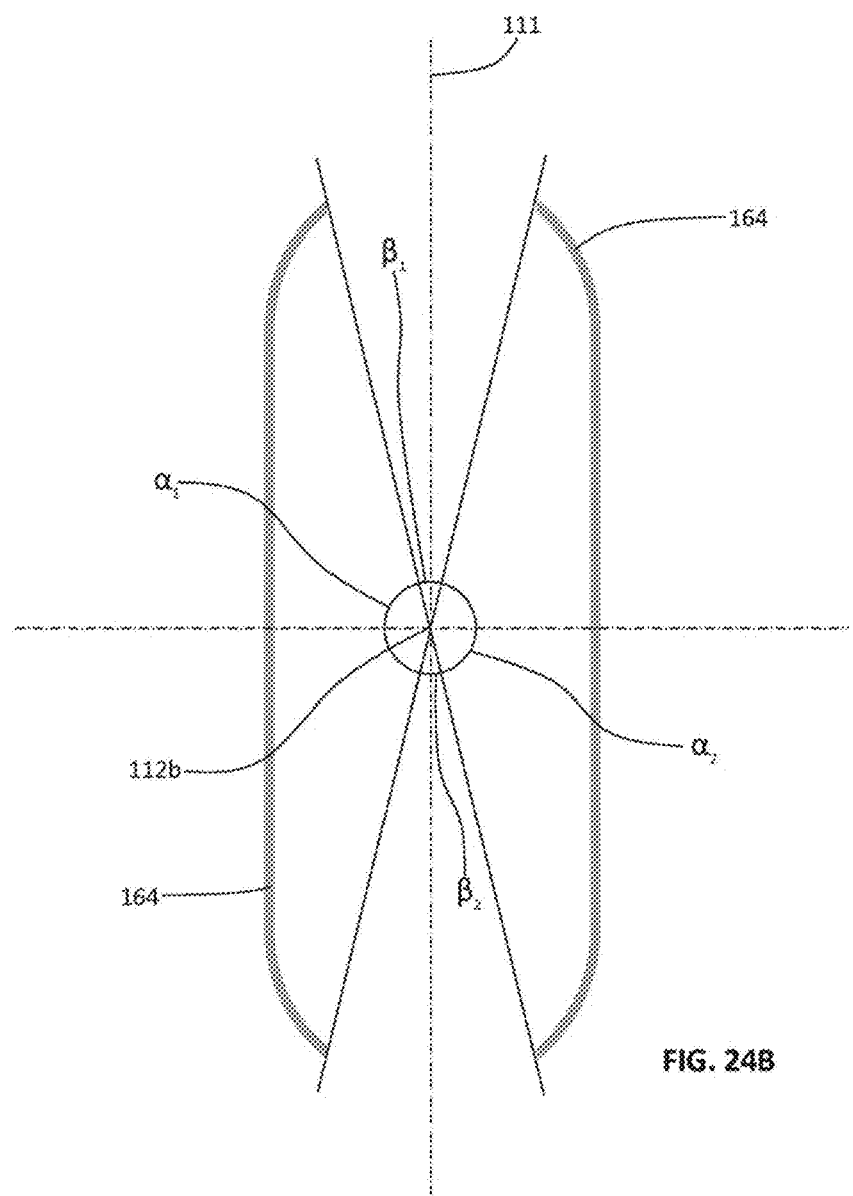
Figure 24C:
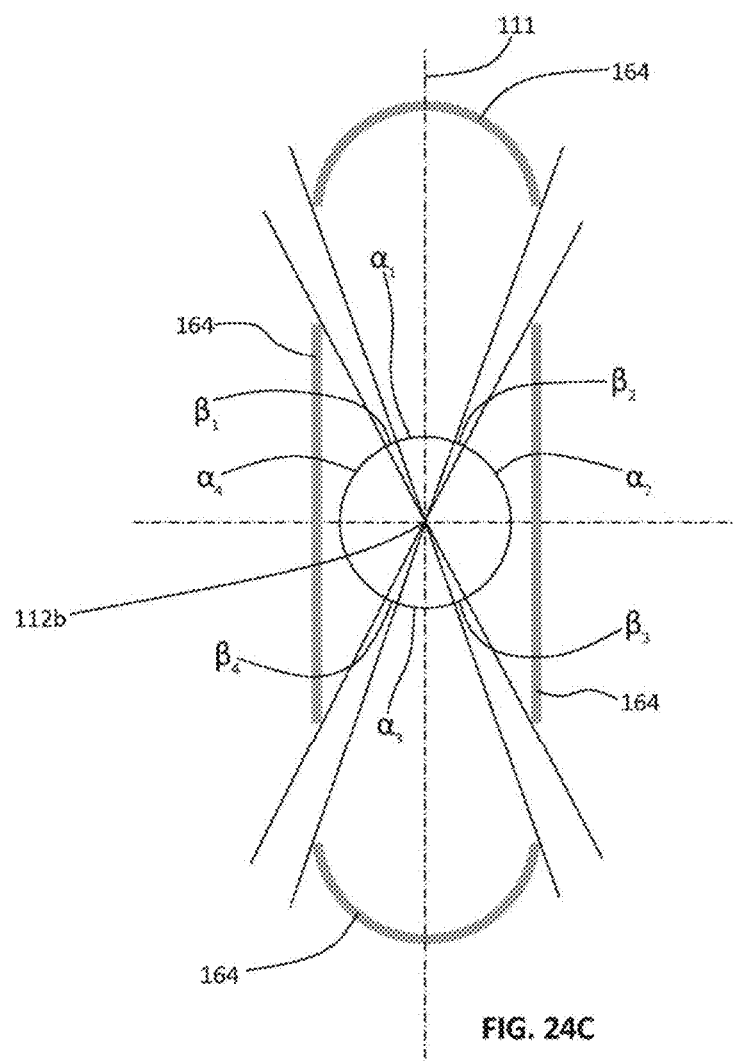

In many circumstances, it may be desired that a configuration of one or more channel portions 164 occupy one or more paths that, individually or in combination, predominately circumscribe a discharge locus 112b. Referring to FIGS. 24A-24C, for purposes herein, a path or plurality of paths of a configuration of channel portions 164 "predominately circumscribe" a discharge locus 112b, when a ray drawn in the x-y plane along the pad surface, originating at a discharge locus 112b and extending radially outwardly in the x-y plane therefrom, will intersect a channel portion 164 when drawn in any of a predominately greater number of possible angular positions about a 360-degree circle with its center at the discharge locus 112b. Referring to FIGS. 24A-24C, by way of illustration, angles α delineate angular portions of a circle within which any ray extending from the center thereof will intersect a channel portion 164; and angles β delineate angular portions of the circle within which any ray extending from the center will not intersect a channel portion 164. Thus, each of the illustrative examples of channel portion 164 configurations shown in FIGS. 24A-24C predominately circumscribe a discharge locus 112*b*, because the total of the angles α is greater than the total of the angles β, i.e., total of angles α is greater than 180 degrees. For FIGS. 24A and 24B, $$(\alpha_1+\alpha_2)>(\beta_1+\beta_2);$$

and for FIG. 24C, $$(\alpha_1+\alpha_2+\alpha_3+\alpha_4)>(\beta_1+\beta_2+\beta_3+\beta_4).$$

For purposes of identifying a discharge locus 112*b* and determining whether a configuration of channel portion(s) 164 predominately circumscribes it, a discharge locus 112*b* may lie anywhere on or approximately on longitudinal axis 111, at any point therealong that is predominately circumscribed by a configuration of channel portion(s) 164 as described above and is within the middle third of the length of the topsheet along the longitudinal axis 111. To illustrate, referring to FIG. 24E, a discharge locus 112*b*$_A$ is predominately circumscribed by channel portion 164 because angle α$_A$ is greater than angle β$_A$, where such a discharge locus 112*b*$_A$ may be identified along longitudinal axis 111 within the middle third (⅓ Lm) of length L. The condition is satisfied in any example in which such a discharge locus such as locus 112*b*$_A$ may be identified, despite the possibility, with some configurations of channel portions 164, of identifying alternate locations such as location 112*b*$_B$ along axis 111 where, e.g., angle α$_B$ is less than angle β$_B$.

Figure 24D:
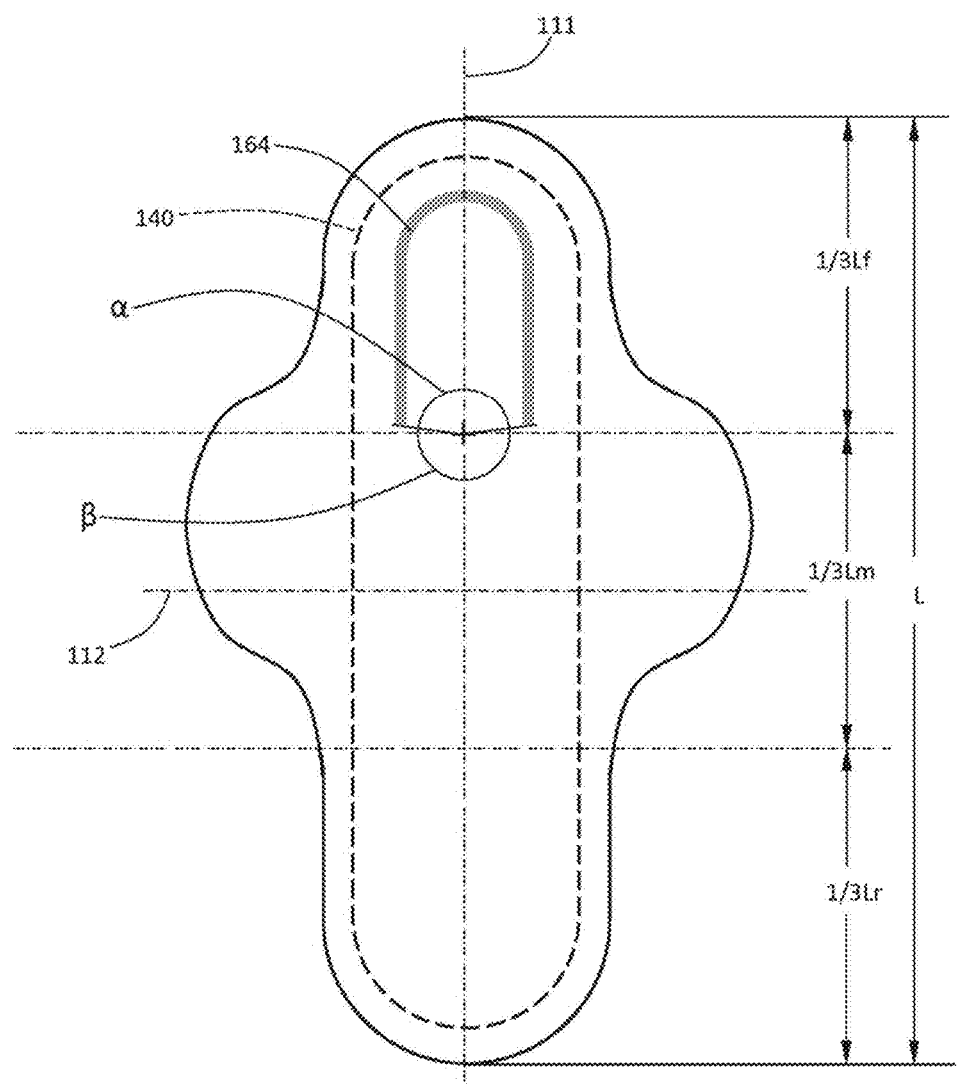
Figure 24E:
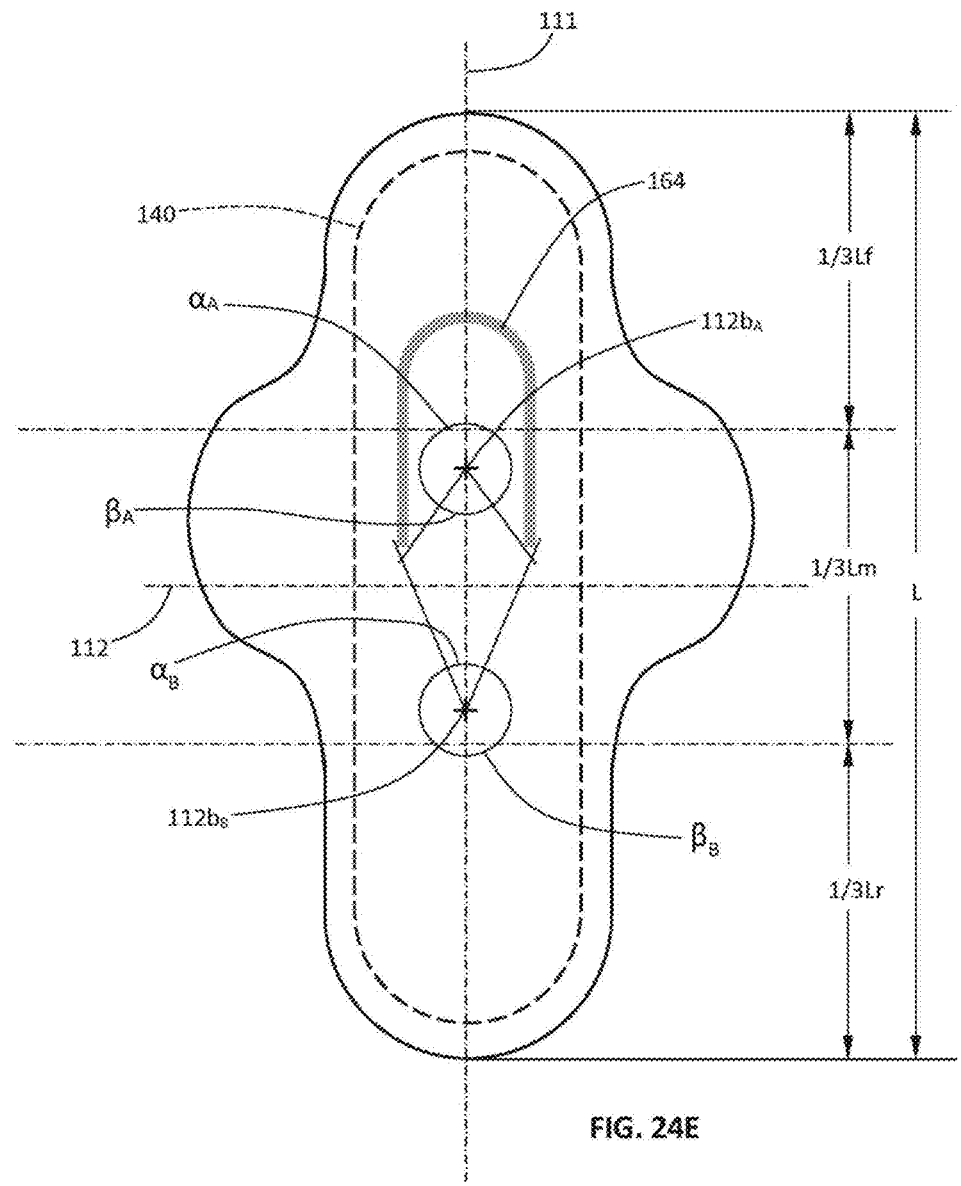

An example of a configuration of channel portion(s) 164 that does not predominately circumscribe a discharge locus is illustrated in FIG. 24D. The configuration shown in FIG. 24D does not predominately circumscribe a discharge locus because no discharge locus can be identified within the middle third (⅓ Lm) of length L, where angle α is greater than angle β. In the example illustrated in FIG. 24D, even when a possible discharge locus is identified at the very edge of middle third (⅓ Lm) of length L as shown, angle α is less than angle β. (In the example depicted in FIG. 24D, angle α is less than 180 degrees.)

From the foregoing description and from the associated figures, it will be appreciated that absence of a discharge locus within the middle third of the length of the pad, that is predominately circumscribed by a configuration of channel portion(s) 164, makes it less likely that a configuration of channel portion(s) 164 will be positioned to capture, channel, promote absorption of, and thereby help prevent migration of discharged fluid outwardly toward an edge of the topsheet.

Other non-limiting examples of configurations of channel portion(s) 164 are illustrated in FIGS. 23A-K, which are proportional as shown, and as shown, would predominately circumscribe a discharge locus located within the middle third of the length of a pad.

It may be desired that channel portion(s) 164 overlie the absorbent structure 140 of the article (in the z-direction), and preferably, be present only in locations on the topsheet overlying the absorbent structure. This is to ensure that any fluid channeled by channel portion(s) 164 is channeled along locations on the topsheet that are underlaid in the z-direction by the absorbent structure, such that channel portion(s) 164 are suitably disposed to facilitate absorption by the underlying absorbent structure 140, through the bottom(s) of the channel portion(s) 164.

Referring again to FIGS. 8-10, it can be seen that channel portions 164 are portions of the section of formed nonwoven web material forming topsheet 120 in which filaments 122 forming portions of the formed nonwoven web material are present in substantially lesser quantity than in built-up regions 166. The respective channel portions 164 and adjacent built-up regions 166 in a nonwoven web material may be formed by a process described below.

Figure 9:
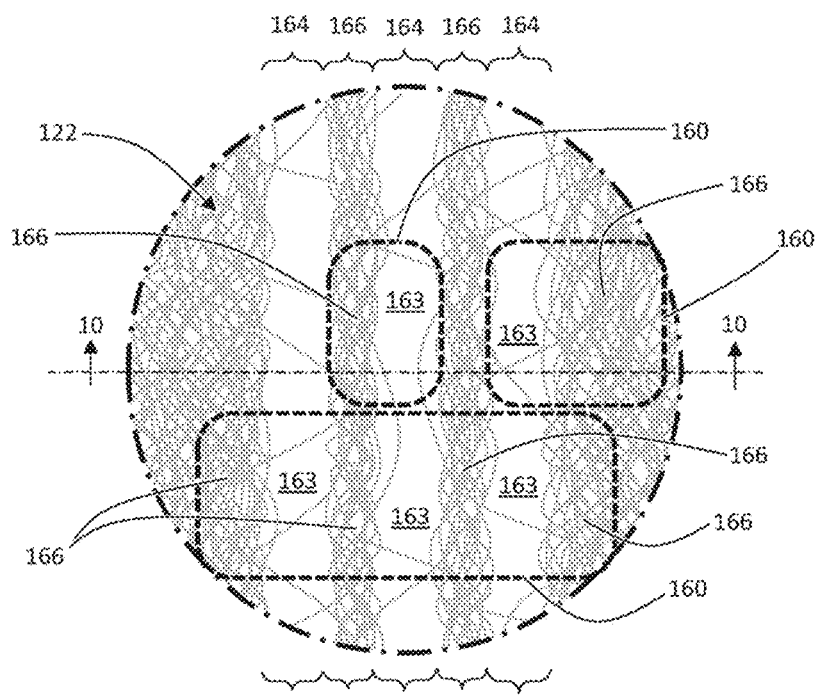
FIG. 9 is an expanded schematic view of the portion of the topsheet identified as "9" in FIG. 6.
Figure 10:
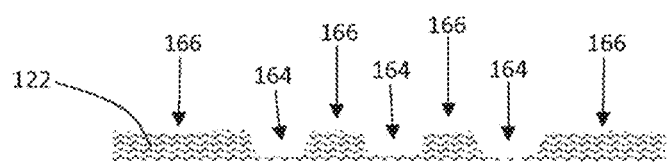
FIG. 10 is a schematic lateral cross section of the portion of the topsheet shown in FIG. 9.

Referring to FIG. 9, any number of zones 160 may be identified. Each zone includes at least one attenuated region 163 having a relatively substantially lesser fiber and/or filament area density adjacent to at least one built-up region 166 having a relatively substantially greater fiber and/or filament area density. Corresponding to the relatively lesser fiber and/or filament area density of the attenuated regions 163 and relatively greater fiber and/or filament area density of the built-up regions 166, attenuated regions 163 may have a relatively lower basis weight than adjacent built-up regions 166. The nonwoven web material may be manufactured as described below, such that these differences between adjacent regions 163, 166 within a zone 160 may be visually discernible. Visual discernibility of these regions and zones may be manifest in visible localized differences/variations in filament and/or fiber area density, web thickness/caliper and/or web transparency/opacity. For example, a viewer may perceive channel portions 164 in a section of formed nonwoven web material forming a topsheet 120 to be channels or grooves following oval-shaped paths along the surface of the topsheet 120, wherein the channels or grooves are visually discernible as regions of visually, discernibly lower filament and/or fiber area density, visually, discernibly lower web thickness/caliper and or visually, discernibly lower web opacity (conversely, higher translucency). In order to substantially ensure or enhance visual discernibility as well as the other functional aspects of the topsheet features described herein, it may be desired to control the filament deposition process and distribution between attenuated regions 163 and built-up regions 166, such that they differ in average basis weight by at least a factor of 2. As discussed below, distribution of filaments between attenuated regions and built-up regions may be controlled by selection of a substrate forming belt material for a given air permeability, and by control of the airflow drawing rate of the forming vacuum system.

Such channels or grooves may serve esthetic/decorative and functional purposes. A user/consumer of a feminine hygiene pad product having such features may perceive visible channels/grooves (with built-up regions therebetween and/or surrounding them) to serve a containment function by providing physical barriers to flow of exudate fluids across the surface of the pad and off the side(s) or end(s) thereof. In some configurations the combination of such channel portions with built-up regions therebetween or surrounding them may actually serve such a barrier function. The channel portions 164 may literally constitute channels in and along which exudate fluids may more freely collect and flow, while the surrounding built-up regions 166 may constitute physical barriers tending to inhibit fluid in the channels from flowing longitudinally or laterally outward toward the edge (outer perimeter 128) of the pad. This may be particularly true when filaments and/or fibers forming the pad have been spun from polymer resins (without or with hydrophobicity-enhancing melt additives) having hydrophobic surface energy properties, which can inhibit flow of aqueous fluids along their surfaces.

It will be appreciated that configurations of channel portions 164 such as those non-limiting examples described above and illustrated in FIGS. 6 and 23A-23K may provide visual appeal and liquid containment functionality not only to topsheets for feminine hygiene pads, but also to topsheets for adult incontinence pads, disposable absorbent pants and disposable diapers.

Referring to FIGS. 6-8, a section of formed nonwoven web material forming topsheet 120 of a feminine hygiene pad or adult incontinence pad may include one or more attenuated regions 163 defining hinge portions 168 formed therein, proximate to wing fold lines 115. Hinge portions 168 may extend approximately longitudinally along any portion, or substantially all, of the longitudinal length of wing portions 114 where they extend away from the main (central) portion of the pad. Hinge portions 168 may be formed in a manner similar to the manner in which channel portions 164 may be formed, as will be described below. Like channel portions 164, hinge portions 168 may be adapted to be visually discernible and may include visually discernible attenuated regions of comparatively lesser filament and/or fiber area density and basis weight, adjacent visually discernible built-up regions of comparatively greater filament and/or fiber area density and basis weight, within visually discernible zones. Because they are arranged longitudinally proximate to line(s) 115 along which wing portions are desirably folded to wrap about the crotch portion of underpants, and because they may constitute areas of visibly reduced presence of filaments and/or fibers and/or visibly reduced topsheet thickness/caliper, hinge portions 168 may serve to visually indicate a folding location. Additionally, the reduced number of filaments and/or fibers in hinge portions 168 causes the web material therealong to be less stiff than the surrounding built-up regions 166, functionally promoting and facilitating folding along the hinge portions.

Figure 25:
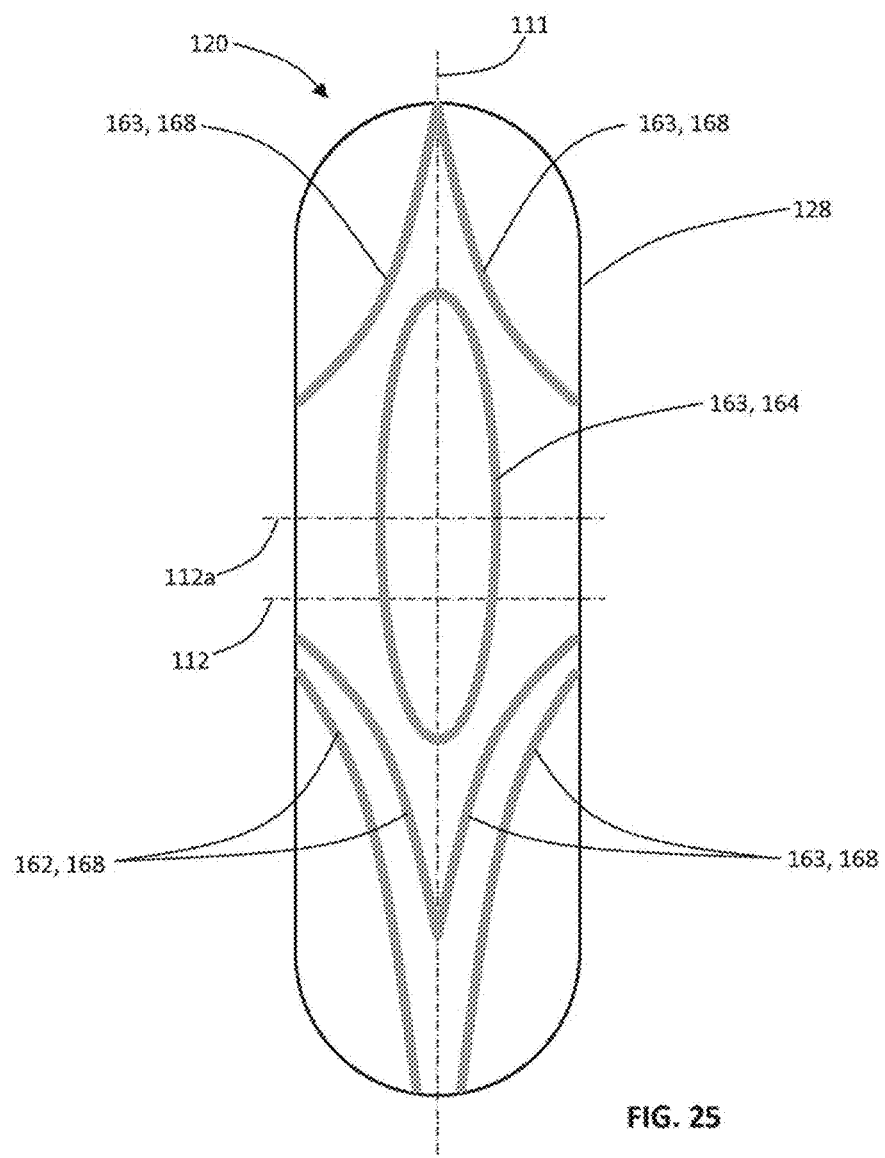
FIG. 25 is a plan view of an example of a topsheet with a configuration of channel portions and hinge portions.

In addition or as an alternative to providing hinge structures for wings, configurations of hinge portions 168 may be located along other portions of the topsheet to enhance flexibility, comfort and/or body conformity. Referring to FIG. 25, by way of non-limiting example, hinge portions 168 may be included to provide lines or paths along which the corners of the pad are enabled to more easily flex, to allow the pad to better and/or more comfortably conform to the user/wearer's body during wear.

It will be appreciated that a characteristic of a hinge portion 168 may be that it follows or parallels a path or line that extends between two edges of the topsheet where it defines wings 114, and one or more attenuated regions 163 occupy the majority of such path and form the hinge portion 168.

Other Ordered Arrangements

Figure 18:
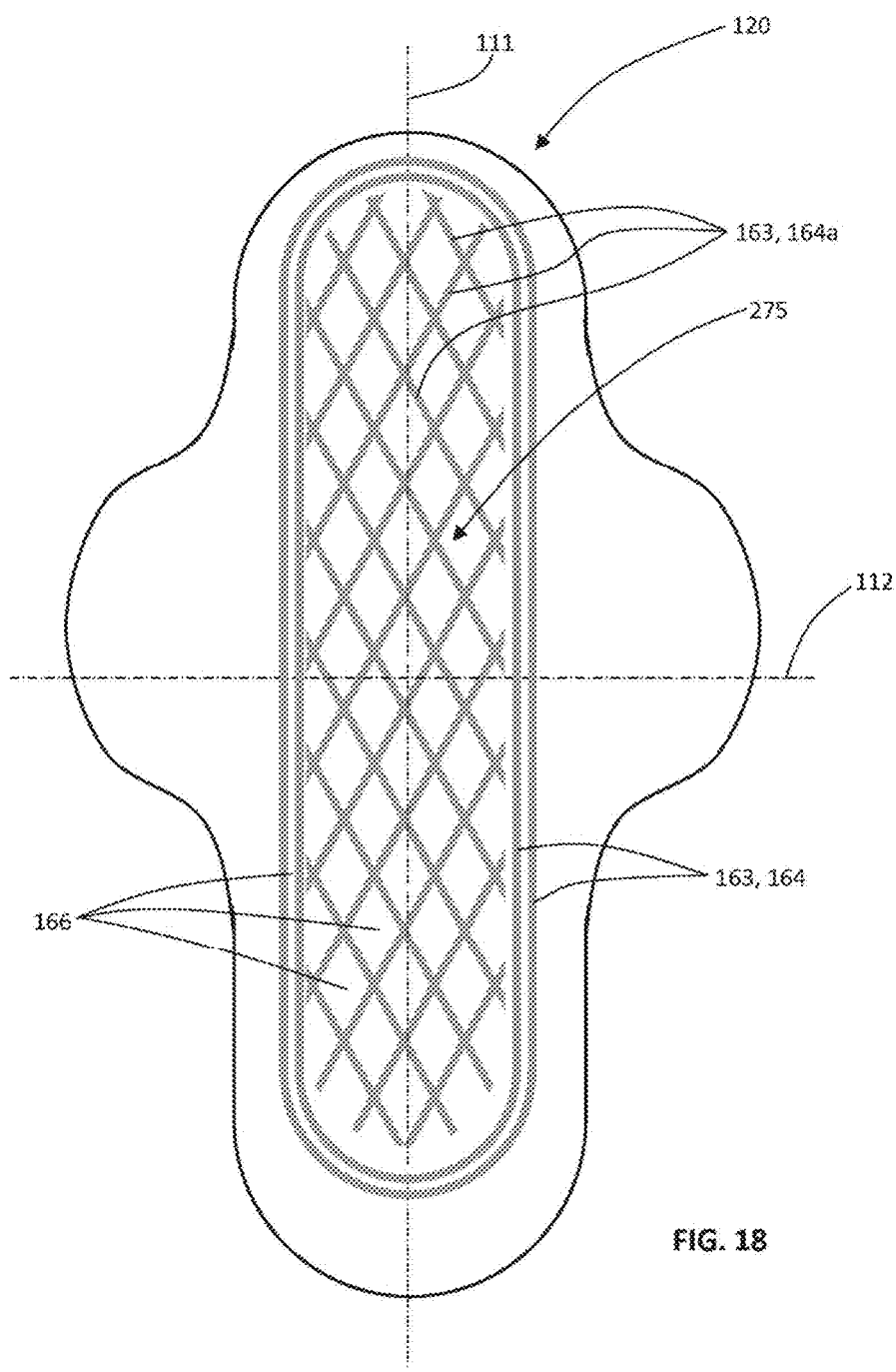
FIGS. 18 and 19 are schematic plan views of examples of topsheets having additional examples of features formed according to the processes described herein.
Figure 19:
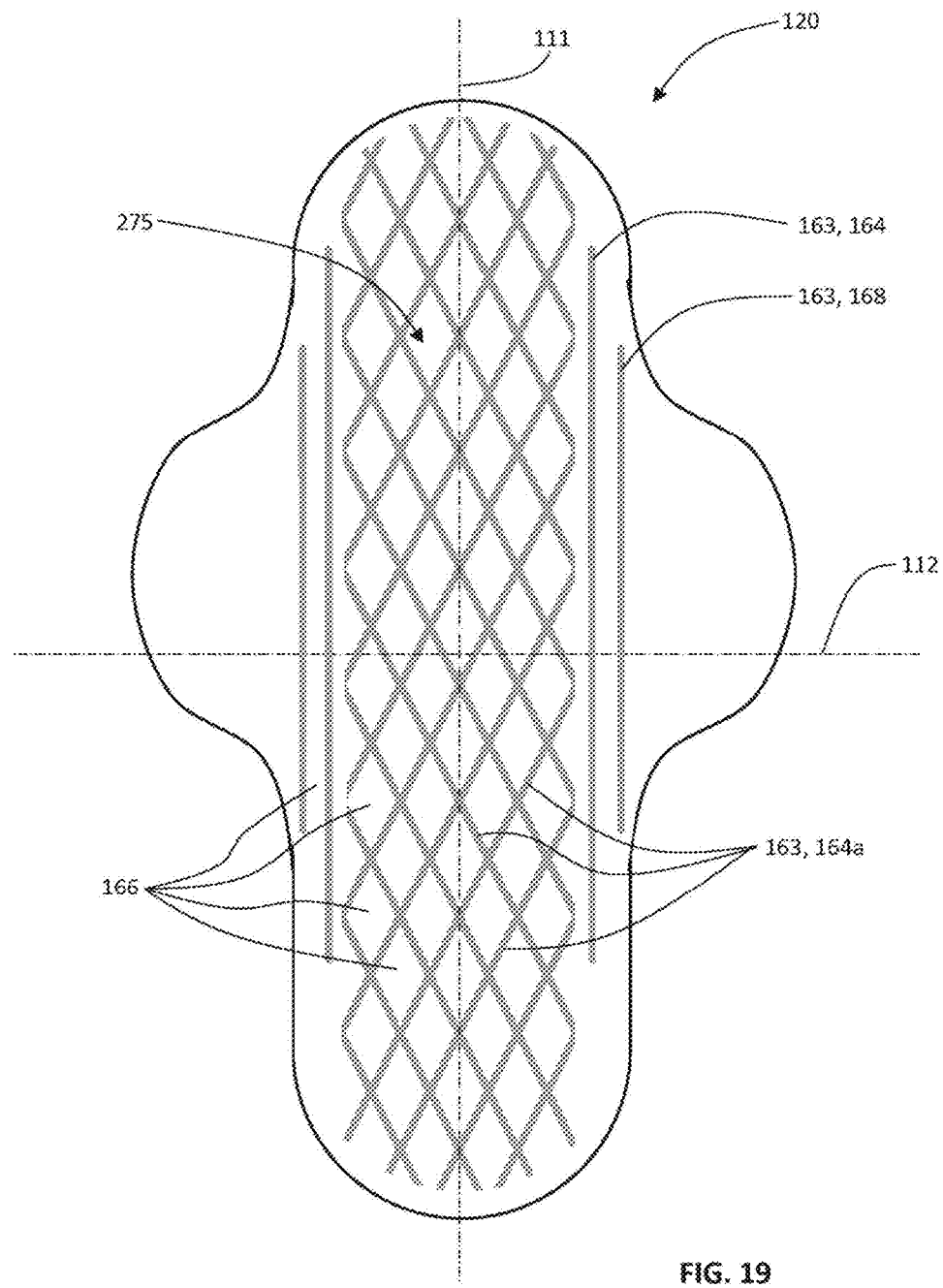

An advantage provided by the forming belt manufacturing technique described below and in the references incorporated by reference in the present disclosure, however, is that airflow blocking structures 262 may be formed and configured on a forming belt 260 according to an unlimited number of variants of desired combinations of recognizable, visually discernible shapes, images of natural or artificial objects, people, animals, fanciful characters, anthropomorphic characters, decorative elements, functional features, designs, patterns, sizes, spacings etc., by simply printing the negative of the desired configuration on the mask used to selectively block resin-curing light, as described below. It will be appreciated, therefore, that in addition to forming airflow blocking structures to impart the channel portions 164 and hinge portions 168 to a nonwoven web material formed on a forming belt as described herein, the airflow blocking structures may be designed and included on a forming belt to impart other functional features, decorative/ornamental features, or a combination thereof, to the nonwoven web material. FIGS. 18 and 19 illustrate two possible, non-limiting examples. In the examples shown in FIGS. 18 and 19, a pattern 275 of continuous low bulk portions 164a formed of attenuated region(s) 163, and defining a pattern of diamond-shaped built-up regions 166, may be formed on a section of formed nonwoven web material to form a feminine hygiene pad topsheet, in combination with one or more channel portions 164 and/or hinge portions 168. It will be appreciated that a pattern such as pattern 275 may be desired for functional and/or decorative purposes. In the examples depicted in FIGS. 18 and 19, pattern 275 of low bulk portions 164a may serve both purposes, by imparting a visually pleasing decorative appearance to the topsheet, and by providing a network of channel-like structures that may function as fluid channels in a manner similar to the channel portions 164 as described above, serving to help distribute flows of body exudate fluid across the pad surface area and drain them to underlying absorbent structure, while built-up regions 166 may serve to maintain separation between the channel-like structures' lower z-direction depths (and exudate fluid they carry) from the wearer's skin. Pattern 275 of low bulk portions 164a may be imparted by use of a forming belt with a suitable corresponding pattern of airflow blocking structures formed thereon, in the manner described below. As suggested by FIGS. 18 and 19, it may be desired in some circumstances that any pattern 275 configuration of continuous low bulk portions does not include portions that extend beyond the edges of the absorbent structure, or alternatively, to the edges of the topsheet, so as to avoid channeling exudate fluids to positions at which they may be unlikely to be absorbed by the absorbent structure, and/or might flow off the edges of the pad.

An unlimited number of other patterns 275 of attenuated regions and built-up regions are possible. As reflected in the additional non-limiting examples of FIGS. 26A, 26B, 27, and 29, it may be desired in some circumstances for a topsheet in its longitudinally and laterally central areas to include a pattern 275 of discrete low bulk portions 165 which, rather than being continuous across a substantial portion of the length or width of the topsheet in the manner of channel portions, and rather than intersecting or interconnecting with other low bulk portions 164a as suggested in FIGS. 18 and 19, are each discrete and entirely surrounded by a continuous area of built-up region 166, like "islands" (corresponding with low bulk portions 165) in a "sea" (corresponding with built-up region 166). A pattern of such discrete low bulk portions 165, without any traversing channel portions, may be included and may occupy a central area of the topsheet proximate a discharge locus and/or at the intersection of the longitudinal and lateral axes 111, 112. Non-limiting examples of such patterns are depicted in FIGS. 26A, 26B, and 29, appearing in the laterally central portions of the images and extending from top to bottom. In such examples each discrete low bulk portion 165, being relatively sparsely populated by filaments, can better serve as a pathway for fluid to move in a z-direction through the topsheet (behaving in a manner akin to a drain hole through the topsheet), while the surrounding, continuous built-up region 166 can serve as a barrier to inhibit x-y-direction lateral/longitudinal flow and thereby inhibit spreading of discharged fluid across the topsheet. These effects may be enhanced by manipulation of the hydrophobic/hydrophilic characteristics of various surfaces, portions and/or regions of the web from which the topsheet is made, through the techniques, materials and configurations described below. It has been learned that, generally, consumers/users of feminine hygiene pads prefer pads configured such that discharged menstrual fluid effectively moves suitably rapidly through the topsheet in a z-direction to absorbent material beneath, such that the x-y dimensions of staining of the topsheet by received fluid are as small as possible and centralized about the discharge locus. This visual signal indicates to the user that the absorbent system is working effectively to receive, capture and contain discharged fluid. Thus, a pattern of low bulk portions 165 such as depicted by way of non-limiting examples in FIGS. 26A, 26B, and 29, that does not include continuous channels such as depicted in FIGS. 18 and 19 at the intersection of the lateral and longitudinal axes and/or proximate the expected discharge locus 112b on the topsheet, may be preferred. Without intending to be bound by theory, it is believed that a pattern of discrete low bulk portions 165 occupying a total area (such as an area that is predominately circumscribed by one or more channel portions 164), is most effective at draining fluid in a z-direction when the discrete low bulk portions 165 occupy a fraction of the total area occupied by the pattern of 5 percent to 30 percent, more preferably 8 percent to 25 percent, and even more preferably 10 percent to 22 percent, of the total area occupied by the pattern.

Figure 28:
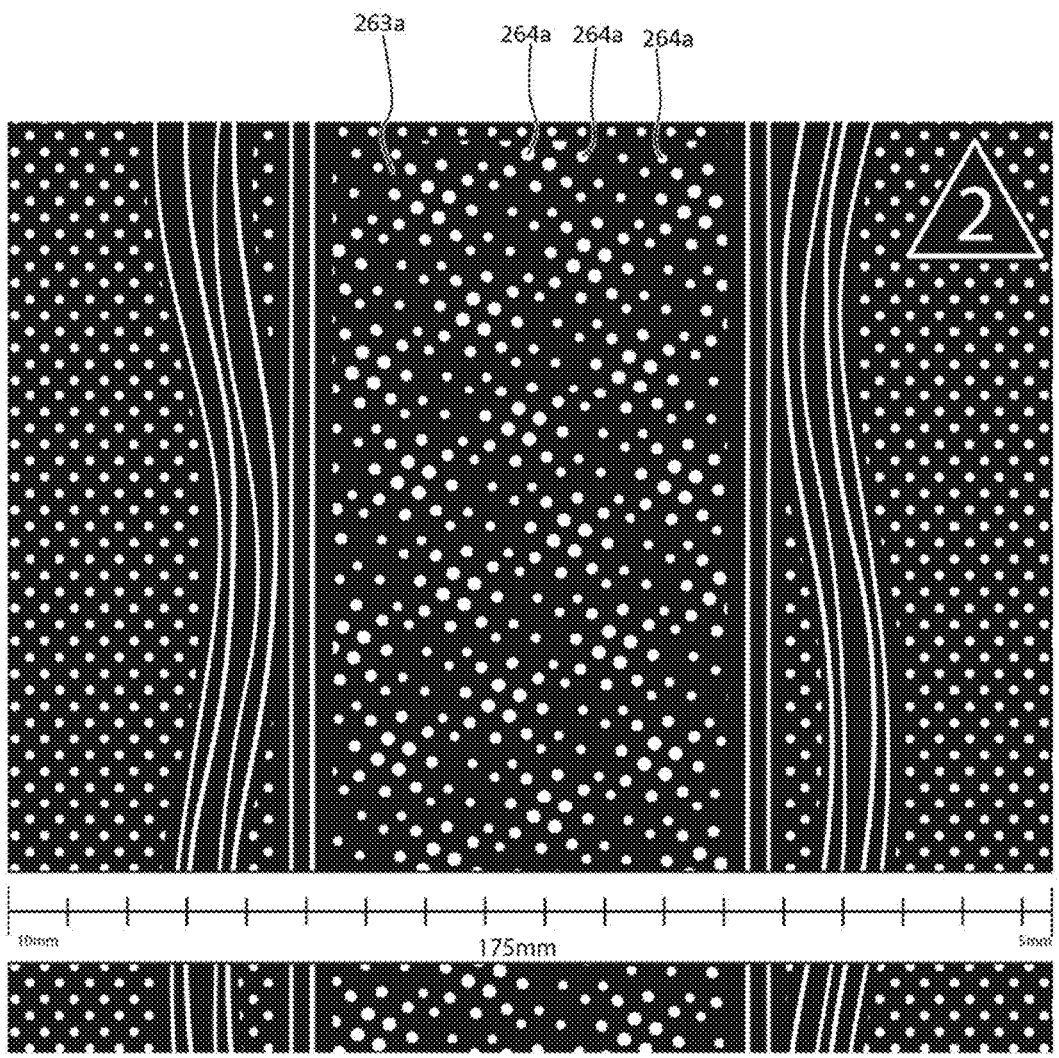
FIG. 28 is an image of a portion of a mask used to produce a forming belt used to make the nonwoven web material sample depicted in FIG. 26B, with a superimposed dimension scale indicator.

For purposes herein, the percent fraction of the total area occupied by discrete low bulk portions reflects, and may be determined by, measurement of the corresponding area of the airflow blocked regions 264 in the x-y plane on the forming belt 260 used to form the topsheet material (described below), which, in turn, may also be reflected by corresponding resin curing regions 264a (shown in FIGS. 28 and 30) and/or resin non-curing regions 263a (shown in FIGS. 28 and 30) on a mask used to make the forming belt (according to the manufacturing method described below). Additionally, the percent fraction of a total area occupied by a pattern of discrete low bulk portions 165 may be measured directly from the topsheet web itself using a Pattern Analysis Test as described in either of U.S. Provisional Applications Ser. Nos. 62/842,792 and 62/842,807. Where a range for percent fraction of a total area occupied by a pattern of discrete low bulk portions 165 is specified and/or recited in a claim herein, it is intended to apply to and cover such range as may be determined by any of the methods identified in this paragraph. If a Pattern Analysis Test set forth in one of the applications referenced above is found to be insufficient to measure such percent fraction under particular circumstances, resort to one of the other methods (e.g. measurement of area of airflow blocked regions 264 on forming belt, or measurement of area of resin curing regions 264a and/or resin non-curing regions 263a on a mask) may be had.

Figure 22:
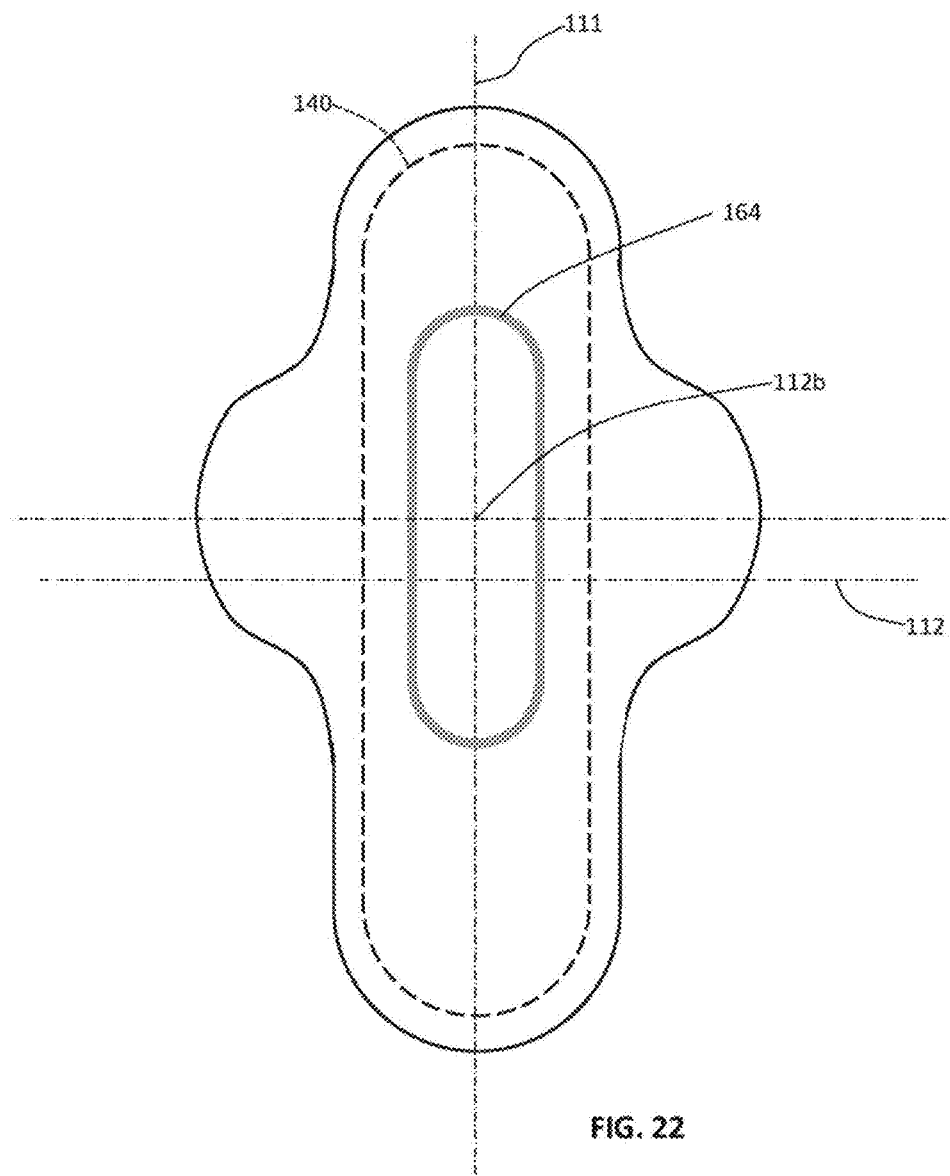
FIG. 22 is a plan view of an example of a feminine hygiene pad with a configuration of a channel portion.
Figure 23A:
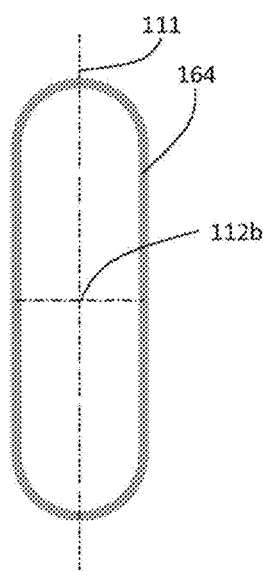
FIGS. 23A-23K are plan views of examples of configurations of channel portions for a topsheet.
Figure 23B:
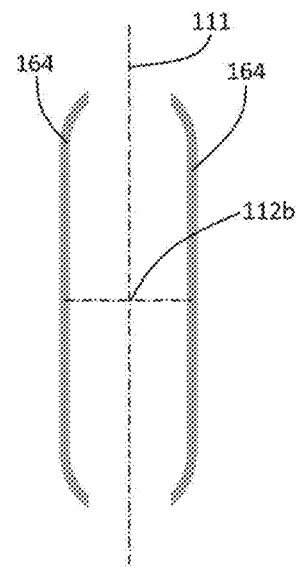
Figure 23C:
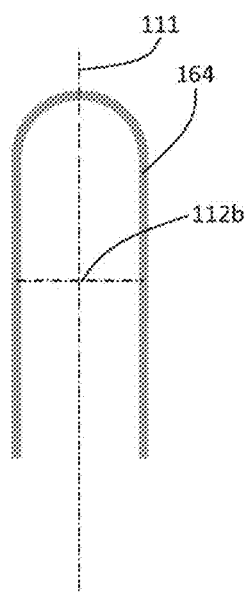
Figure 23D:
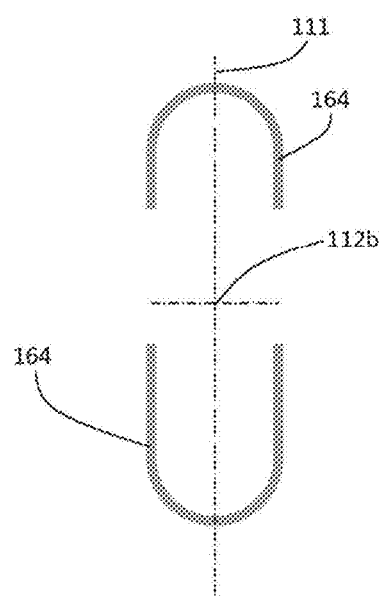
Figure 23E:
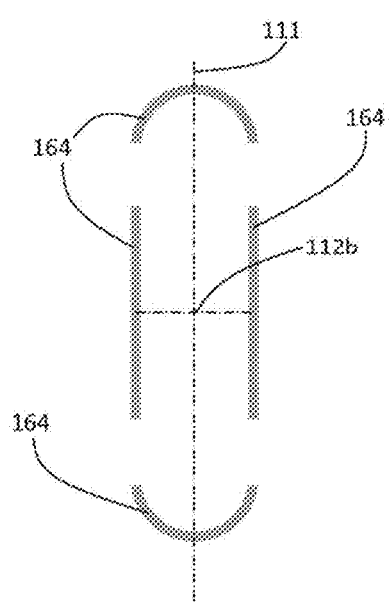
Figure 23F:
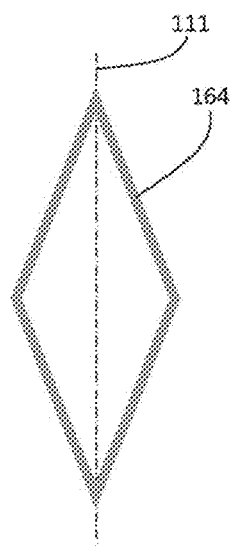
Figure 23G:
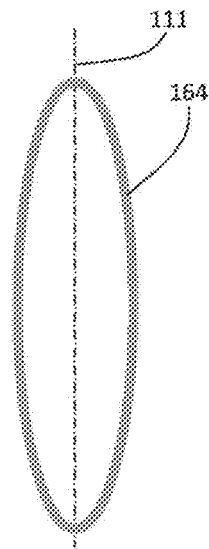
Figure 23H:
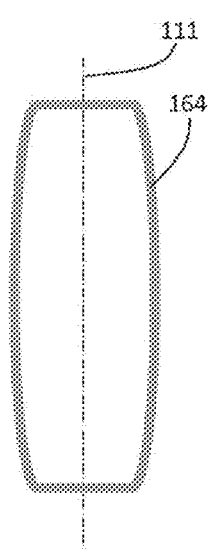
Figure 23I:
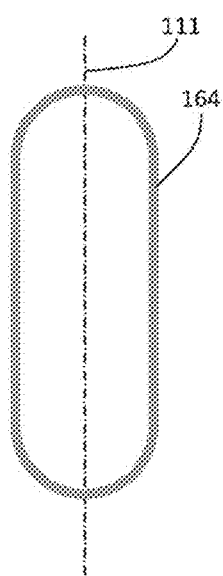
Figure 23J:
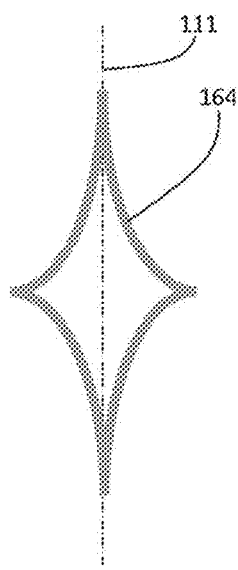
Figure 23K:
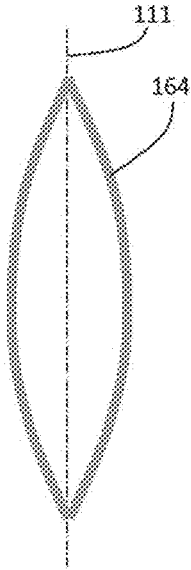

By way of particular, non-limiting example, referring to FIG. 22, if the total area circumscribed by channel portion 164 is occupied by a pattern of discrete low bulk portions collectively occupying 8 percent to 22 percent of the area occupied by the pattern, it is believed that optimal z-direction fluid draining effect may be achieved for the topsheet configuration.

In addition to controlling the area collectively occupied by discrete low bulk portions in a pattern thereof, their individual sizes may be regulated (via design of the forming belt 260, as described below) for beneficial effect. If a majority or all of the discrete low bulk portions 165 in the pattern each have an area of at least 0.8 mm$^2$ and no greater than 20 mm$^2$, more preferably no greater than 7 mm$^2$, user perceptions of tactile softness of the topsheet may be enhanced, while chances of exposure of the user's skin to the wet absorbent structure will be minimized while still maintaining optimal draining performance and control of stain spreading. (When the discrete low bulk portions have a circular shape, the ranges set forth immediately above equate with a low bulk portion diameter of at least 1 mm and no greater than 5 mm, more preferably no greater than 3 mm.)

As suggested in FIGS. 26A, 26B, 27, and 29, a pattern 275 of discrete low bulk portions 165 occupying longitudinally and/or laterally central portions of the topsheet of may be partially or entirely surrounded by one or more channel portions 164. One or more channel portions 164 may be configured to predominately circumscribe a discharge locus 112b and otherwise function as described above. A pattern of low bulk portions present proximate and/or about the intersection of the lateral and longitudinal axes and/or at the expected discharge locus 112b on the topsheet may be included within any of the configurations of channel portions 164 described herein, and illustrated by way of non-limiting example in FIGS. 6, 22, 23A-23K, 24A, 24B, 24C, 24E and 25. Channel portions are further described in U.S. Patent Application Publication No. US 2019/0298587.

As will be apparent from the description below, the method and process of formation of the web material will result in "sidedness," wherein one x-y surface of the formed web material exhibits a substantially greater visible topography with visible z-direction "heights" of well-defined built-up regions (on the side most proximate the forming belt during formation—forming belt side), than does the opposing x-y surface (opposite side). This sidedness makes it desirable that, when the web material is used to form a topsheet, the forming belt side faces the wearer on the end product. This makes the topography more visible to the wearer, may enhance visual and tactile softness signals conveyed by the topographical features, and facilitates the functionality of the topsheet as described herein.

Absorbent Structure

Referring back to FIGS. 1 and 2, the absorbent structure may comprise an absorbent core and a fluid management layer. The absorbent structure may be joined to the topsheet in any suitable manner Some examples include the use of a plurality of discrete fusion bonds, ultrasonic bonds, pressure bonds, adhesive, or combinations thereof.

The absorbent core may comprise any suitable absorbent core known in the art. The absorbent core may be manufactured from a wide variety of liquid-absorbent materials commonly used in disposable absorbent articles such as comminuted wood pulp which is generally referred to as airfelt. The absorbent core may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials.

The configuration and construction of the absorbent core may vary (e.g., the absorbent core may have varying caliper zones, a hydrophilic gradient, a superabsorbent gradient, or lower average density and lower average basis weight acquisition zones; or may comprise one or more layers or structures). In some forms, the absorbent core may comprise one or more channels, such as two, three, four, five, or six channels.

The absorbent core of the present disclosure may comprise one or more adhesives, for example, to help immobilize the SAP or other absorbent materials within a core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

Fluid Management Layer

As noted, the absorbent structure 140 may further comprise a fluid management layer. The fluid management layer may be disposed between the absorbent core and the topsheet. The fluid management layer of the present disclosure may comprise a plurality of carded, integrated fibers. The fluid management layer of the present disclosure may comprise one or more carded webs which are subsequently fiber integrated with one another. Where only one carded web is utilized, the fibers of the carded web are integrated.

A wide variety of configurations for a fluid management layer may be achieved. However, it is important that the fluid management layer of the present disclosure have adequate openness to allow for quick acquisition of fluid. With this in mind, the carded webs which make up the fluid management layer may be different from one another. For example, one of the carded webs may comprise a different fiber blend than the others. Specifically, assuming the first carded web would be closest to the wearer-facing surface in an absorbent article, the fiber selection for a first carded web may be such that there is more openness associated with this web. A second carded web may be similarly configured. In contrast, a third carded web may be configured to collect liquid insults from the void space of the first and second carded webs and effectively distribute these liquid insults to an absorbent core. Where a fiber makeup of one of the carded webs is different than a fiber makeup of another carded web, where the two carded webs are integrated, is a heterogenous configuration. Alternatively, where the carded webs being integrated all have the same fiber makeup is termed a homogeneous configuration.

Once the carded web(s) are integrated, they cannot be manually separated—at least not without substantial effort and time. Each carded nonwoven web forms a stratum in the overall fluid management layer. Each stratum can maintain its unique properties for at least a portion of the stratum along the z-direction, even when integrated into a larger fluid management layer. The fluid management layer can provide capillary suction to "pull" fluid through the topsheet, which is competing for trickle/low flow conditions. The fluid management layer also can contain a gush for providing distribution functions to efficiently utilize the absorbent core, as well as provide intermediate storage until the absorbent core can accept fluid.

The fluid management layer of the present disclosure can have a basis weight of up to 75 grams per square meter (gsm); or a basis weight of up to 70 gsm; or a basis weight in the range of between about 30 gsm to about 75 gsm, from about 45 gsm to about 70 gsm, and between about 50 gsm to about 65 gsm, including any values within these ranges and any ranges created thereby.

Some absorbent articles may not require as much basis weight as recited above. For example, liners which generally do not have the same level of absorbent capacity as menstrual pads may be able to have a reduced basis weight over that which was recited above. For example, the fluid management layer may have a basis weight of between 20 gsm to 70 gsm or between 35 gsm to about 65 gsm, or from about 40 gsm to about 60 gsm, specifically including all values within these ranges and any ranges created thereby. In one specific example, the fluid management layer of the present disclosure can have a basis weight of between about 45 gsm to about 70 gsm. The basis weights of the fluid management layers of the present disclosure may be determined by the Basis Weight method disclosed herein.

The fluid management layer provides increased caliper to the absorbent article which can translate into a softer feeling article. Additionally, the fluid management layer of the present disclosure can provide increased resiliency to the absorbent article over that of currently available absorbent articles. Typically, there is a tradeoff with resiliency and softness. Softer materials may have difficulty recovering their shape from applied forces in one or more directions. And the converse may be true for resilient materials. In the absorbent article context, resilient materials typically exhibit good recovery from applied forces; however, they are typically not perceived as being very soft. It is also worth noting that many absorbent articles can exhibit good resilience properties when dry; however, upon absorption of a liquid insult, their resiliency decreases substantially. The absorbent articles of the present disclosure exhibit good resiliency properties both in dry and wet conditions.

Notably, typical calipers of webs from conventional spunlace lines achieve a caliper factor (caliper per 10 gsm of basis weight) of 0.03 to 0.12. In contrast, the fluid management layers of the present disclosure can exhibit a caliper factor of at least 0.13 mm, more preferably at least about 0.15 mm, or most preferably about 0.2 mm, including any values within these ranges and any ranges created thereby. The fluid management layer of the present disclosure can have a caliper factor of between 0.13 mm to about 0.3 mm, or more preferably from about 0.14 mm to about 0.25 mm, or most preferably from about 0.15 mm to about 0.22 mm, including all values within these ranges and any ranges created thereby. Caliper data is provided hereafter for an Inventive Sample as well as a Comparative Sample. The caliper and caliper factor of the fluid management layers of the present disclosure may be determined by the Caliper and Caliper Factor test methods disclosed herein. It is important to note that the caliper factors mentioned heretofore are with regard to caliper obtained using 0.5 kPa of applied pressure as noted in the Caliper method disclosed herein.

The inventors have surprisingly discovered that in order to achieve the increase in caliper factor, a simpler process path may be utilized to produce the spunlace web. Generally, the web path through a hydroentangling line is tortuous and subjects the web to both compressive and tensile stresses. This tortuous web path requires water jet pressures high enough to entangle the fibers, creating tensile strength sufficient to survive subsequent web handling. These water jets are applied to both surfaces of the web. This additional water pressure required to create sufficient entanglement for tensile strength is generally in excess of the pressure needed to create the desired fluid handling pore structure and meaningfully reduces caliper of the resultant web. Additionally, the web is subject to significant radial compression and tensile stress as the web is wound around a variety of vacuum drums and rolls such that additional water jets can further entangle the constituent fibers of the strata. Moreover, these webs may be subsequently wound around dryer drums subjecting them to additional compressive force. However, the inventors have found that winding of the web around these rolls causes compression on the web and actually reduces the caliper of the web.

In contrast, the inventors have discovered that through the use of a simplified web path that reduces radial compressive stresses/excessive tensile forces and the appropriate selection of fibers in the fluid management layer, caliper of the fluid management layers of the present disclosure can be maintained. For example, the use of rolls and the number of water jets utilized can be reduced via the simplified path. As such, while the level of entanglement is not to the extent provided by the conventional process, sufficient tensile strength in the web can be provided by selecting the appropriate combination of fibers as disclosed herein, e.g. stiffening fibers which can be heat treated. Again, the simplified path and appropriate fiber selection as described herein, allows the fluid management layers of the present disclosure to achieve caliper factors that have heretofore not been achievable.

Additionally, the caliper factors of the fluid management layers of the present disclosure mentioned above were derived from caliper data from material which was rolled for storage/shipping. Caliper measures pre-winding could be taken which would yield much higher caliper factors. However, such caliper measurements may not necessarily reflect the fluid management layer that makes it into an article.

The inventors have also found that the processing technique for creating caliper in the fluid management layer can be utilized not only on spunlace materials where the strata are heterogeneous but also where the strata are homogeneous, e.g. each stratum has the same fiber makeup. Additionally, the inventors have surprisingly found that spunlace materials constructed with this process along with appropriate fiber selection can also provide good resiliency and recovery from compression, with improved fluid handling performance above those spunlace materials that are produced via typical spunlace processes.

In addition to the softness and resiliency benefits of the absorbent articles of the present disclosure, some additional benefits include stain size control and faster fluid acquisition. Stain size is important in the way the absorbent article is perceived. In the menstrual context, when the stain is large, users may feel like their product is near failure just from the optics of the stain in relation to the outer periphery of the absorbent article. In contrast, smaller stains can provide users with assurance that the absorbent article will not fail as the stain is more inboard of the outer periphery than its large stain counterpart.

Regarding fluid acquisition speed, this attribute is key in making the user feel dry and clean. When the absorbent article takes a long time to drain liquid insults from the topsheet, users can feel wet. Additionally, when fluid stays on the topsheet for an extended period of time, users can feel like their skin in the intimate area is unclean.

It is also worth noting that due to the fiber integration, the fluid management layer does not require adhesives or latex binders for stability. Additionally, the carded nonwoven of the fluid management layers of the present disclosure can be manufactured from an assortment of suitable fiber types that produce the desired performance characteristics. For example, the fluid management layer may comprise a combination of stiffening fibers, absorbent fibers and resilient fibers.

As will be discussed in additional detail hereafter, the types of fibers in the fluid management layer of the present disclosure are described in terms of their functionality within the fluid management layer. For example, absorbent fibers are utilized to absorb liquid insults. Stiffening fibers are utilized to bond together via heat treatment thereby providing stiffness and resiliency to the fluid management layer. Resilient fibers are utilized to provide recovery from compressive forces which act against the fluid management layer.

In order to enhance the stabilizing effect of the integration, crimped, carded fibers may be utilized. One or more of the absorbent fibers, stiffening fibers, and resilient fibers may be crimped prior to integration. For example, where synthetic fibers are utilized, these fibers may be mechanically crimped via intermeshing teeth. As for the absorbent fibers, these fibers may be mechanically crimped and/or may have a chemically induced crimp due to the variable skin thickness formed during creation of the absorbent fibers.

As noted previously, the amount of absorbent fibers can impact the absorption of liquid insults to the wearer-facing surface or topsheet. However, when absorbent fibers absorb liquid, they tend to lose some of their structural integrity. The loss of structural integrity can reduce the resiliency of the absorbent article and lead to increased bunching and increased leakage. Accordingly, while in principle, a large percentage of absorbent fibers is good for draining liquid insults from the wearer-facing surface and/or topsheet rapidly, a large percentage can also lead to other problems with the absorbent article as mentioned heretofore.

In light of the potential problems associated with having too much of a weight percentage of absorbent fibers, the inventors have found that the fluid management layer of the present disclosure may comprise from about 10 percent to about 60 percent by weight, from about from about 15 percent to about 50 percent by weight, from about 20 percent to about 40 percent by weight, specifically including any values within these ranges and any ranges created thereby of absorbent fibers. In one specific example, the fluid management layer may comprise from about 20 percent to about 30 percent by weight of absorbent fibers. The weight percentages of the absorbent fibers, resilient fibers, and/or stiffening fibers may be determined via the Material Compositional Analysis method disclosed herein.

Additionally, due to the loss of integrity of the absorbent fibers when wet, the fluid management layer also can comprise sufficient weight percentage of resilient fibers which impact the recovery of the absorbent article from compressive loads experienced during use. The inventors have found that the fluid management layer of the present disclosure may comprise from about 15 percent to about 70 percent, from about 20 percent to about 60 percent, or from about 25 percent to about 50 percent by weight of resilient fibers, specifically reciting all values within these ranges and any ranges created thereby. In one specific example, the fluid management layer may comprise from about 30 percent by weight to about 40 percent by weight resilient fibers.

Moreover, stiffening fibers may be utilized to help the fluid management layer of the present disclosure provide resiliency to the absorbent article. For example, as discussed hereafter, stiffening fibers may be bonded to one another via heat treatment of the fluid management layer during production. This bonding of the stiffening fibers creates a support matrix which helps with resiliency and stiffness of the fluid management layer. With this in mind, the fluid management layer may comprise from about 25 percent to about 70 percent, from about 30 percent to about 60 percent, or from about 40 percent to about 55 percent of stiffening fiber, specifically reciting all values within these ranges and any ranges created thereby. In one specific example, the fluid management layer may comprise from about 40 percent by weight to about 50 percent by weight of stiffening fibers.

As mentioned previously, the fluid management layers of the present disclosure can provide their respective absorbent articles with a soft cushiony feel with good resiliency. Where caliper, resiliency, and a soft cushiony feel are the objective, the weight percentage of stiffening fibers may be greater than or equal to the weight percentage of resilient fibers. The weight percentage of absorbent fibers can be less than the weight percentage of resilient fibers and/or stiffening fibers. In general, a higher weight percentage of absorbent fibers is considered to be beneficial in rapidly absorbent fluid insults; however, given the proximity of the absorbing fibers to the topsheet, it is beneficial for the absorbent core to dewater the absorbing fibers. Where there is a larger percentage of absorbing fibers, typically a larger core is required to dewater the absorbent fibers. This typically leads to higher costs. With this in mind, a ratio of absorbent fibers in the fluid management layers of the present disclosure to stiffening fibers by weight percentage can be from about 1:7 to about 2:1, from about 1:4 to about 1.5:1, from about 1:2 to about 1:1, specifically reciting all values within these ranges and any ranges created thereby Similarly a ratio of absorbent fibers to resilient fibers by weight percentage can be from about 1:7 to about 3:1, from about 1:2 to about 2:1, or from about 1:1.5 to about 1:1, specifically reciting all values within these ranges and any ranges created thereby.

Regardless of whether the fluid management layer is utilized in an adult incontinence article menstrual article, liner, or other hygiene article, of importance is the ability of the fluid management layer to acquire liquid insults from the topsheet and to pull the liquid far enough from the topsheet, such that the topsheet does not feel wet. To accomplish this, the inventors have found that the increased caliper of the fluid management layer discussed herein can facilitate fluid acquisition due to the increased void volume of the fluid management layer. The higher caliper at the lower basis weight equals more void volume with higher permeability. Additionally, the increased caliper of the fluid management layer can also provide a stain masking benefit. Namely, the stains that are visible through the topsheet with absorbent articles using the fluid management layer of the present disclosure, appear much smaller than their conventional fluid management layer counterparts.

It is worth noting that for a set basis weight of a fiber, larger diameter fibers can provide more void volume between adjacent fibers as compared to their smaller diameter counterparts. As such, the fiber size of the fibers in the fluid management layer can be important. For example, for a set percentage weight of fiber, as fiber size goes up there are fewer fibers per gram, and fewer fibers can equal more space between the fibers. Ideally, particularly in the context of menstrual fluid, the fluid management layer can have void volume as well as some degree of capillarity to drain the topsheet.

With the above in mind, the inventors have also surprisingly discovered that careful selection of the fiber types in each of the strata in the fluid management layer and the linear densities of the fiber types can achieve the desired outcome of quick acquisition and low rewet. The fiber types of the individual strata are discussed in additional detail hereafter. It is worth noting that the discussion below regarding fiber types in the strata of the fluid management layer assumes that the first carded nonwoven web is nearer to the topsheet than the web(s) of the additional card(s).

Some suitable linear density values of absorbent fibers for use in the fluid management layers of the present disclosure are provided. For example, the absorbent fiber linear density may range from about 1 dtex to about 7 dtex, from about 1.2 dtex to about 6 dtex, or from about 1.3 dtex to about 5 dtex, specifically reciting all values within these ranges and any ranges created thereby. In one specific example, the absorbent fiber may comprise a linear density of about 1.3 dtex. In another specific example, the absorbent fiber may comprise a linear density of about 1.7 dtex. The dtex of the absorbent fibers, stiffening fibers, and resilient fibers may be determined via the Fiber Decitex method disclosed herein.

The absorbent fibers of the fluid management layer may have any suitable shape. Some examples include trilobal, "H," "Y," "X," "T," round, or flat ribbon. Further, the absorbing fibers can be solid, hollow or multi-hollow. Other examples of suitable multi-lobed, absorbent fibers for utilization in the fluid management layers detailed herein are disclosed in U.S. Pat. No. 6,333,108 to Wilkes et al, U.S. Pat. No. 5,634,914 to Wilkes et al., and U.S. Pat. No. 5,458,835 to Wilkes et al. The trilobal shape can improve wicking and improve masking. Suitable trilobal rayon is available from Kelheim Fibres and sold under the trade name Galaxy. While each stratum may comprise a different shape of absorbing fiber, much like mentioned above, not all carding equipment may be suited to handle such variation between/among strata. In one specific example, the fluid management layer comprises round absorbent fibers.

Any suitable absorbent material for the absorbent fibers may be utilized. Some examples of absorbent materials include cotton, pulp, rayon or regenerated cellulose or combinations thereof. In one example, the fluid management layer 30 may comprise viscose cellulose fibers. The length of the absorbent fibers can be in the range of about 20 mm to about 100 mm, or about 30 mm to about 50 mm or about 35 mm to about 45 mm, specifically reciting all values within these ranges and any ranges created thereby. In general, the fiber length of pulp is from about 4 to 6 mm and cannot used in conventional carding machines because the pulp fibers are too short. So, if pulp is desired as a fiber in the fluid management layer, then additional processing to add pulp to the carded webs may be required. As an example, pulp may be airlaid between carded webs with the combination being subsequently integrated. As another example, tissue may be utilized in combination with the carded webs and the combination may be subsequently integrated.

As noted previously, in addition to absorbent fibers, the fluid management layer of the present disclosure may comprise stiffening fibers. Stiffening fibers may be utilized to help provide structural integrity to the fluid management layer. The stiffening fibers can help increase structural integrity of the fluid management layer in a machine direction and/or in a cross-machine direction which can facilitate web manipulation during processing of the fluid management layer for incorporation into a disposable absorbent article.

Some suitable linear density values of stiffening fiber are provided. For example, the stiffening fiber linear density may range from about 1.0 dtex to about 6 dtex, from about 1.5 dtex to about 5 dtex, or from about 2.0 dtex to about 4 dtex, specifically reciting all values within these ranges and any ranges created thereby. In another specific example, the dtex of the stiffening fibers is about 2.2 dtex.

Some examples of suitable stiffening fibers include bi-component fibers comprising polyethylene and polyethylene terephthalate components or polyethylene terephthalate and co-polyethylene terephthalate components. The components of the bi-component fiber may be arranged in a core sheath arrangement, a side by side arrangement, an eccentric core sheath arrangement, a trilobal arrangement, or the like. In one specific example, the stiffening fibers may comprise bi-component fibers having polyethylene/polyethylene terephthalate components arranged in a concentric, core-sheath arrangement where the polyethylene is the sheath.

While other materials may be useful, the inventors have found that the stiffness of polyethylene terephthalate is useful in creating a resilient structure. In contrast, the polyethylene component of the stiffening fibers can be utilized to bond to one another during heat treatment. This can help provide tensile strength to the web in both the MD and CD. Additionally, the bonding of the polyethylene component to other polyethylene components of stiffening fibers can create fixed points in the nonwoven. These fixed points can reduce the amount of fiber-to-fiber sliding which can increase the resiliency of the material.

One of the benefits of the stiffening fibers is that the integrated nonwoven may be heat treated post fiber entanglement. The heat treatment can provide additional structural integrity to the integrated nonwoven by forming bonds between adjacent stiffening fibers. So, where there is a higher percentage of stiffening fibers, more connection points may be created. Too many connection points can yield a much stiffer fluid management layer which may negatively impact comfort/softness. As such, the weight percentage of the stiffening fibers is of critical importance when designing an absorbent article.

Regarding the heat stiffening process, any suitable temperature may be utilized. And, the suitable temperature may be impacted, in part, by the constituent chemistry of the stiffening fibers as well as by the processing fluid management layer web. For example, the fluid management layer web may be heat stiffened at a temperature of about 132 degrees Celsius. However, it is also worth noting, that in order to provide a uniform stiffness property across the fluid management layer, any heating operation should be set up to provide uniform heating to the fluid management layer web. Even small variations in temperature can greatly impact the tensile strength of the fluid management layer.

As noted previously, the fluid management layer of the present disclosure comprises resilient fibers. The resilient fibers can help the fluid management layer maintain its permeability and compression recovery. Any suitable size fiber may be utilized. For example, the resilient fibers can have a linear density of about 4 dtex to about 15 dtex, from about 5 dtex to about 12 dtex, or from about 6 dtex to about 10 dtex, specifically reciting all values within these ranges and any ranges created thereby. In one specific example, the fluid management layer may comprise resilient fibers having variable cross sections, e.g. round and hollow spiral, and/or may comprise resilient fibers having variable dtex's. In yet another specific example, the resilient fibers of the present disclosure may comprise a dtex of about 10. In such forms, the resilient fibers may be hollow spiral.

The resilient fibers can be any suitable thermoplastic fiber, such as polypropylene (PP), polyethylene terephthalate, or other suitable thermoplastic fibers known in the art. The length of the resilient fibers can be in the range of about 20 mm to about 100 mm, or about 30 mm to about 50 mm or about 35 mm to about 45 mm. The thermoplastic fibers can have any suitable structure or shape. For example, the thermoplastic fibers can be round or have other shapes, such as spiral, scalloped oval, trilobal, scalloped ribbon, and so forth. Further, the PP fibers can be solid, hollow or multi-hollow. The resilient fibers may be solid and round in shape. Other suitable examples of resilient fibers include polyester/co-extruded polyester fibers. Additionally, other suitable examples of resilient fibers include bi-component fibers such as polyethylene/polypropylene, polyethylene/polyethylene terephthalate, polypropylene/polyethylene terephthalate. These bi-component fibers may be configured as a sheath and a core. The bi-component fibers may provide a cost-effective way to increase basis weight of the material while additionally enabling optimization of the pore size distribution.

The resilient fibers can be polyethylene terephthalate (PET) fibers, or other suitable non-cellulosic fibers known in the art. The PET fibers can have any suitable structure or shape. For example, the PET fibers can be round or have other shapes, such as spiral, scalloped oval, trilobal, scalloped ribbon, hollow spiral, and so forth. Further, the PET fibers can be solid, hollow or multi-hollow. In one particular example, fibers may be fibers made of hollow/spiral PET. Optionally, the resilient fibers may be spiral-crimped or flat-crimped. The resilient fibers may have a crimp value of between about 4 and about 12 crimps per inch (cpi), or between about 4 and about 8 cpi, or between about 5 and about 7 cpi, or between about 9 and about 10 cpi. Particular non-limiting examples of resilient fibers can be obtained from Wellman, Inc. Ireland under the trade names H1311 and T5974. Other examples of suitable resilient fibers for utilization in the carded staple-fiber nonwovens detailed herein are disclosed in U.S. Pat. No. 7,767,598 to Schneider et al.

It is worth noting that the stiffening fibers and resilient fibers should be carefully selected. For example, while the constituent chemistries of the stiffening fibers and the resilient fibers may be similar, resilient fibers should be selected such that their constituent material's melting temperature is higher than that of the stiffening fibers. Otherwise, during heat treatment, resilient fibers could bond to stiffening fibers and vice versa and could create an overly rigid structure.

Without wishing to be bound by theory, it is believed that for weight percentage of absorbent fibers above about 30 percent, within the gsm ranges disclosed herein, the resilient fibers and/or stiffening fibers should be carefully selected. Where a soft, cushiony fluid management layer with a caliper factor of at least 0.13 or greater as described herein, the resilient and/or stiffening fibers can be selected to counteract the loss of structural integrity of the absorbent fibers when wet. For example, a higher dtex of resilient fiber may be beneficial in counteracting the loss of integrity experienced by the absorbent fibers. In such instances, resilient fibers may be utilized having a dtex of between about 5 dtex to about 15 dtex, from about 6 dtex to about 12 dtex, or from about 7 dtex to about 10 dtex.

In addition to or an alternative thereof, the stiffening fibers may be configured to provide greater structural integrity. For example, the stiffening fibers may comprise bicomponent fibers in a core-sheath configuration where the sheath is co-polyethylene terephthalate. However, with such a material change, additional problems may occur. For example, the joining of materials to the fluid management layer may then only be via adhesive as opposed to fusion bonding.

Still another example which is in addition to or independent of the foregoing is an increase in bonding of the stiffening fibers. Where the absorbent fibers comprise more than 30 percent by weight of the fluid management layer, the heat at which the stiffening fibers are bonded may be increased and/or the time of exposure may be increased. This can increase the number of bonds in the stiffening fiber matrix which can counteract the loss of integrity of the absorbent fibers when wet. However, with the increase in the number of bonds comes an increase in stiffness. The increase in stiffness can decrease the perception of softness by the user. In a similar regard, in addition to or alternatively thereto, the linear density of the stiffening fibers may be increased to combat the loss of integrity of the absorbent fibers, where the absorbent fibers make up 30 percent by weight or more. In such instances, the linear density of the stiffening fibers may be from about 3 dtex to about 6 dtex, from about 4 dtex to about 6 dtex.

It is worth noting that while it may appear that the solution to wet collapse is simply to use larger dtex fibers, their use must be balanced. Particularly for viscous fluids, the fluid management layers of the present disclosure can have some degree of capillarity to help drain liquid insults to the wearer-facing surface of the article. Unfortunately, while the use of large dtex fibers can provide caliper benefits, it also detracts from capillarity which can lead to fluid handling issues.

Figure 4A:
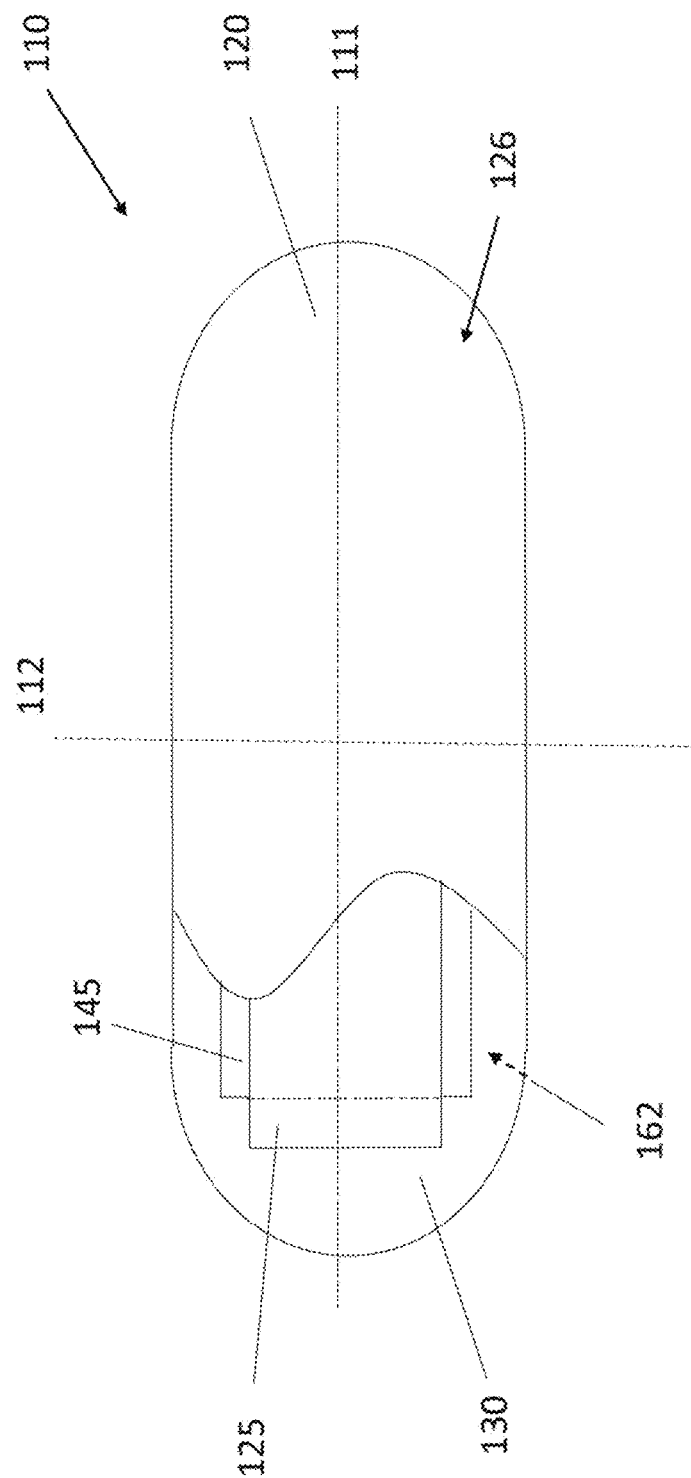
FIG. 4A is a schematic view of another pad constructed in accordance with the present disclosure having portions remove for ease of visualization of the components beneath the topsheet.

The arrangement of the fluid management layer in the pad 110 of the present disclosure is shown in FIG. 4A. As shown, pad 110 comprises an absorbent core 145 and a fluid management layer 135 are disposed between the topsheet 120 and the backsheet 130. The fluid management layer 135 is disposed between the topsheet 20 and the absorbent core 145. The absorbent article has the wearer-facing surface 126 and an opposing garment-facing surface 162. The wearer-facing surface 126 primarily comprises the topsheet 120 while the garment-facing surface 162 primarily comprises the backsheet 130. Additional components may be included in either the wearer-facing surface 126 and/or the garment-facing surface 162. For example, where the absorbent article is an incontinent pad, a pair of barrier cuffs which extend generally parallel to a longitudinal axis 111 of the pad 110, may also form a portion of the wearer-facing surface 126. Similarly, a fastening adhesive may be present on the backsheet 130 and form a portion of the garment-facing surface 162 of the absorbent article.

Figure 4B:
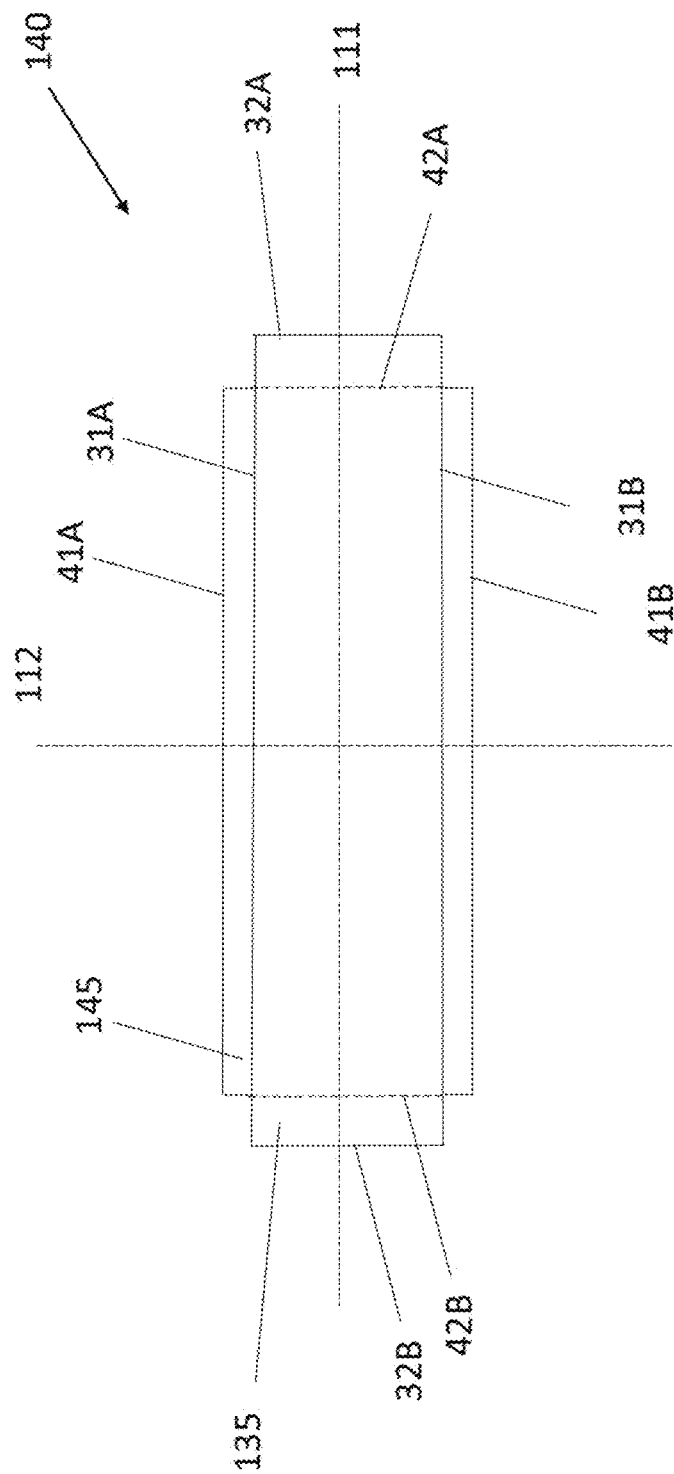
FIG. 4B is a schematic representation of a fluid management layer and absorbent core of the pad of FIG. 4A.
Figure 5A:
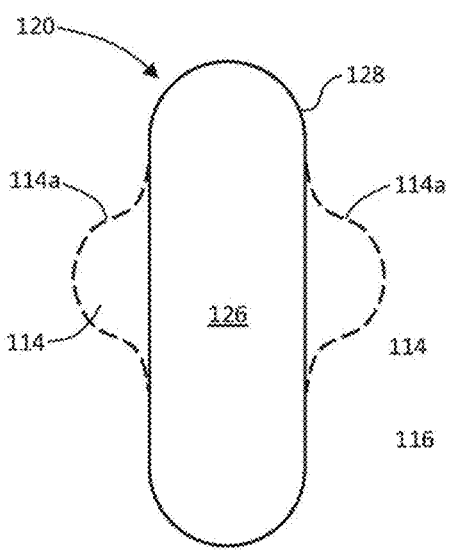
FIGS. 5A-5D are plan views of non-exclusive examples of topsheets of various shapes.
Figure 5B:
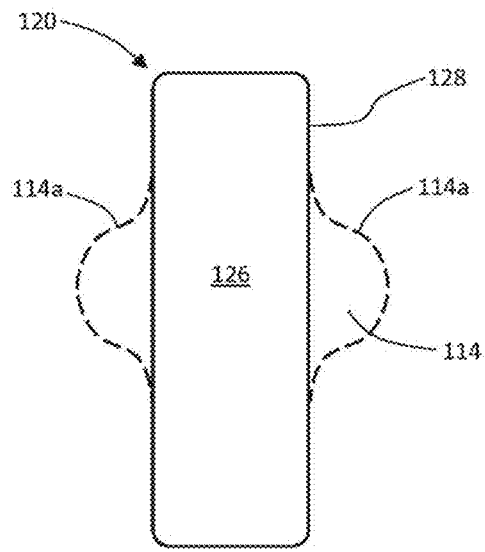
Figure 5C:
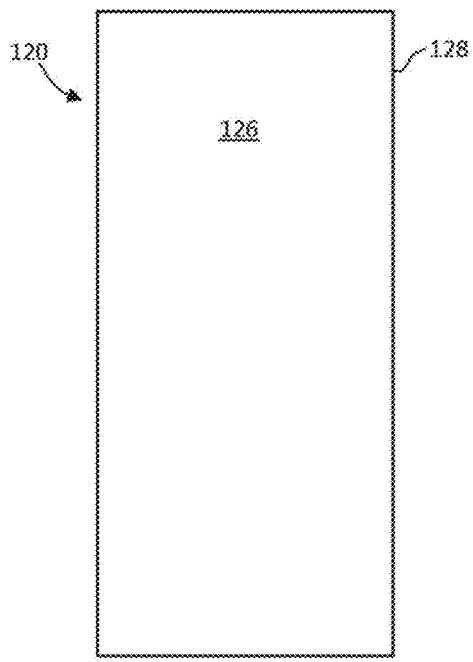
Figure 5D:
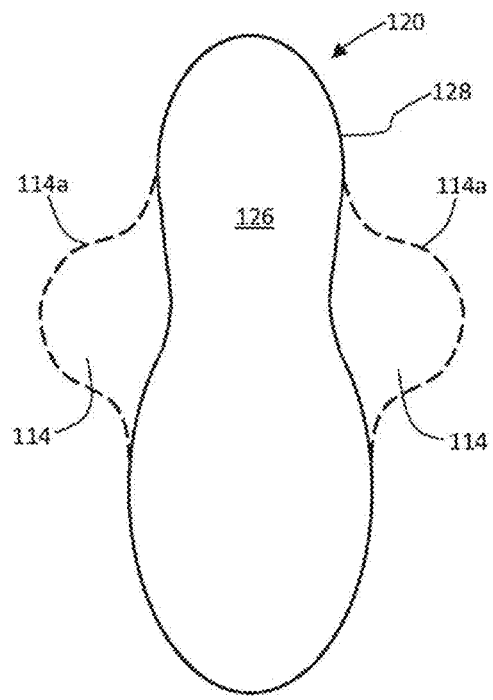

An exemplary configuration for the fluid management layer of the present disclosure is shown in FIG. 4B. As shown, the fluid management layer 135 comprises opposing end edges 32A and 32B which may extend generally parallel to a transverse axis 112. And, the fluid management layer 135 comprises side edges 31A and 32B which may extend generally parallel to the longitudinal axis 111. Similarly, the absorbent core 40 comprises opposing end edges 42A and 42B which may extend generally parallel to the transverse axis 112. And, the absorbent core 145 may comprise side edges 41A and 41B which extend generally parallel to the longitudinal axis 111.

As shown, each of the end edges 32A and 32B of the fluid management layer 135 may be disposed longitudinally outboard of the absorbent core 145. However, this is not necessarily required. For example, the end edges 32A and/or 32B may be coextensive with the absorbent core 40 or the end edges 32A and/or 32B may be disposed longitudinally inboard of the end edges 42A and/or 42B of the absorbent core 145.

Similarly, the side edges 31A and/or 31B may be disposed transversely outboard of the side edges 41A and/or 41B of the absorbent core 145. Or, the side edges 31A and/or 31B may be coextensive with the side edges 41A and/or 41B of the absorbent core 145.

An exemplary process for forming the fluid management layer of the present disclosure is shown in FIG. 4C. As shown, a plurality of carding machines 210, 220, and 230 may each create a carded nonwoven web, e.g. 214, 224, and 234, respectively, which is transferred to a carrier belt 240. Each of the carded nonwoven webs 214, 224, and 234, may be provided to the carrier belt 240 via a web chute 212, 222, 232, respectively. It is also worth noting that after the carded nonwoven 214 is deposited on the carrier belt 240, the carded nonwoven 224 is then deposited on the first carded nonwoven 214 on the carrier belt 240. Similarly, the third carded nonwoven web 234 deposited on the second carded nonwoven 224 and the first carded nonwoven 214 on the carrier belt 240. Subsequently, each of the first, second, and third carded nonwoven webs 214, 224, and 234 are then provided to an integration process 250 which utilizes either needles and/or high-pressure water streams to entangle the fibers of the first, second, and third carded nonwoven webs. Both carding and integration processes are well known in the art.

Additional carding machines may be utilized. Additionally, the fluid management layer of the present disclosure may be produced utilizing only two out of the three cards. In such instances, the first carded web 214 would be deposited on the carrier belt 240. And, subsequently, the second carded web 224 would be deposited on the first carded web 214. Then, the first carded web 214 and the second carded web 224 would be integrated as described herein.

It is worth noting that with the arrangement provided in schematic diagram of FIG. 4C, a wide variety of configurations for a fluid management layer may be achieved. However, it is important that the fluid management layer of the present disclosure have adequate openness to allow for quick acquisition of fluid yet also are able to lock away liquid insults to reduce the likelihood of rewet. With this in mind, the carded webs, i.e. 214, 224, and/or 234, may be different from one another. For example, one of the carded webs may comprise a different fiber blend than the others. Specifically, assuming the first carded web would be closest to the wearer-facing surface in an absorbent article, the fiber selection for the first carded web 214 may be such that there is more openness associated with this web. The second carded web 224 may be similarly configured. In contrast, the third carded web 234 may be configured collect liquid insults from the void space of the first and second carded webs 214 and 224 and effectively distribute these liquid insults to an absorbent core. Alternatively, the first carded web 214, the second carded web 224 and the third carded web 234 may be configured the same.

To illustrate the breakthrough advantages of the exemplary fluid management layer two samples were compared. The comparative sample is a current market material and the inventive sample is created in accordance with the present disclosure. Comparative example fluid management layer—basis weight of 50 gsm, having 40 percent by weight viscose cellulose fibers having a 1.7 dtex; 20 percent by weight polyethylene terephthalate having a 4.4 dtex; and 40 percent by weight bi-component fibers having a first component of polypropylene and a second component of polyethylene having a 1.7 dtex.

Inventive Sample fluid management layer—basis weight of 55 gsm having 20 percent by weight viscose cellulose fibers having a 1.7 dtex; 30 percent by weight hollow spiral polyethylene terephthalate fibers having a 10 dtex; and 50 percent by weight bi-component fibers having a first component polyethylene terephthalate and polyethylene in a core-sheath configuration where the polyethylene is the sheath.

Table 1 shows caliper and caliper factor of the fluid management layers of the inventive sample versus the comparative sample. Note that the calipers were taken at 0.5 kPa. Each of the fluid management layers was removed from a finished product.

TABLE 1

| Sample | Caliper (mm) | Caliper Factor (mm/10 gsm) |
| --- | --- | --- |
| Comparative Sample | 0.47 | 0.09 |
| Inventive Sample | 0.85 | 0.15 |

As shown, the fluid management layer of the present disclosure is 80 percent thicker than its comparative counterpart with only a 10 percent difference in basis weight. And, as noted previously regarding the caliper factor, for the Inventive Sample is much higher than that of the Comparative Sample.

Adjusting Topsheet Surface Chemistry for Hydrophilicity

Figure 20:
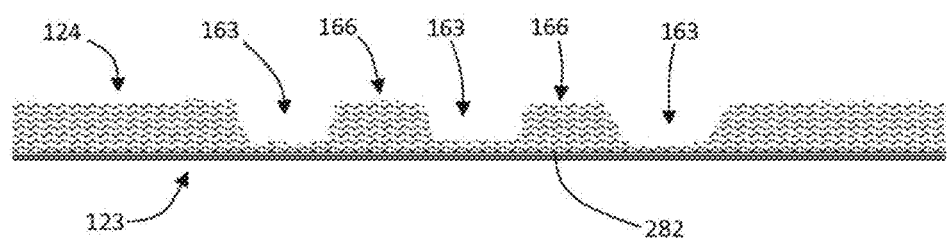
FIGS. 20 and 21 are schematic lateral cross-section views of portions of examples of topsheets formed of nonwoven web material, illustrating presence of materials added to primary filament components.

Referring to FIG. 20, the functions of a topsheet formed as described herein may be enhanced by adding hydrophilic material to the formed nonwoven web material at select locations. In some examples, a surfactant may be selectively applied to the absorbent-facing surface 123 of the topsheet material. In a more particular example, a surfactant, or solution or emulsion containing a surfactant, may be applied to an absorbent-facing side of the topsheet material via, for example, use of a kiss roll coater, spray application, printing technique, or any other suitable liquid deposition technique, to deposit an application of surfactant or solution or emulsion containing a surfactant 282 to the material. Under suitable conditions including suitable disposition of filaments and/or fibers in nonwoven web material, and process techniques/conditions, filaments and/or fibers and/or portions thereof occupying and defining the absorbent-facing surface 123 of the topsheet material and the bottoms of the channel portions 164 will have the surfactant applied to them, while filaments and/or fibers and/or portions thereof occupying and defining the wearer-facing surface 124, and built-up regions 166 thereof will have little or no applied surfactant on their wearer-facing surfaces, such that the surfactant is present in a quantity greater on filaments proximate the absorbent-facing side than on filaments proximate the wearer-facing side. In the resulting topsheet, aqueous fluid (liquid body exudate) may be more likely to flow in and along the channels 164 and/or drain into discrete low bulk portions 165, and through the bottom portions thereof generally along a z-direction, to reach absorbent material disposed below the topsheet in the absorbent article, and the built-up regions 166 adjacent the attenuated regions 163, having a relatively greater number of hydrophobic filaments and/or fibers, may tend to slow or block passage of aqueous fluid along the wearer-facing surface 124, along an x-y plane toward the outer perimeter 128 of the in-use wearer-facing portion 126 of the topsheet. It will be appreciated that, to refine or enhance the desired fluid channeling/barrier and/or draining effect, surfactant application techniques and equipment may be adapted to selectively apply surfactant to limited or defined portions of the section(s) of nonwoven web material forming the topsheet. For example, surfactant may be applied only to portions of the absorbent-facing surface 123 lying to the inside of one or more of the channel portions 164 (with respect to an x-y plane occupied by the material), or to portions of the absorbent-facing surface 123 that does not include wing portions 114, etc. Where the nonwoven is predominately formed of polypropylene, in a non-limiting example, a surfactant suitable for application via KISS roll equipment or alternatively inkjet printing equipment may include STANTEX S6887 surfactant spin finish, a product of Pulcra Chemicals/Fashion Chemicals GmbH & Co., Geretsried, Germany.

The surface of the hydrophobic thermoplastic fiber or filament may be rendered hydrophilic by treatment with a surfactant, such as a nonionic or anionic surfactant, e.g., by spraying the fiber or filament with a surfactant, by dipping the fiber or filament into a surfactant or by including the surfactant as part of the polymer melt in producing the thermoplastic fiber. Upon melting and resolidification, the surfactant will tend to remain at the surfaces of the thermoplastic fiber or filament. Suitable surfactants include nonionic surfactants such as BRIJ 76 manufactured by ICI Americas, Inc. of Wilmington, Delaware, and various surfactants sold under the PEGOSPERSE by Glyco Chemical, Inc. of Greenwich, Connecticut Besides nonionic surfactants, anionic surfactants may also be used.

Surfactants may be applied to the thermoplastic fibers of the topsheet at levels of, for example, from about 0.1 to about 0.8 gsm (gram per square meter), more preferably from about 0.1 to about 0.7 gsm, or most preferably from about 0.1 to about 0.5 gsm, specifically reciting all values within these ranges in 0.1 increments and all ranges created thereby, of thermoplastic fiber or filament.

Figure 21:
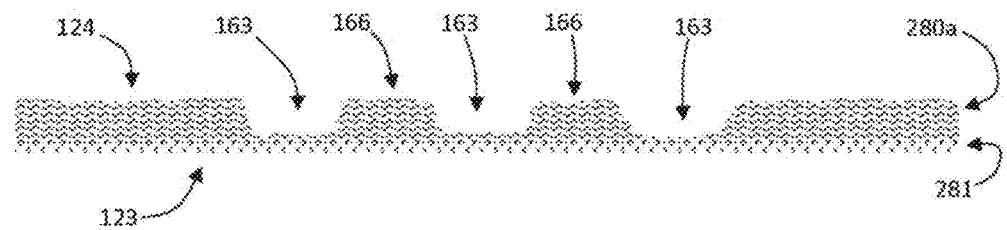

Referring to FIG. 21, in another example, for effects similar to those described immediately above, a nonwoven web material formed as described herein may be coupled via bonding or otherwise with a second layer 281 of filaments and/or fibers formed of hydrophilic material, to form the absorbent-facing surface of the topsheet. In some examples, this second layer 281 may be a second, separately manufactured web material. In other examples, this second layer 281 may be a deposit of filaments and/or fibers deposited over the primary (hydrophobic) filaments and/or fibers forming the built-up regions 166 and channel portions 164 and the wearer-facing surface 124, during the same web manufacturing process.

Coloration

Polymer component resins to be melt spun may include coloring agents such as tinting or pigmenting agents, and/or whitening and/or opacifying agents. In some examples, all of the filaments and/or fibers forming the nonwoven web material may be tinted or pigmented. Alternatively, a second layer 281, of nonwoven material, or of deposited, spun filaments and/or fibers may also include filaments and/or fibers spun from polymer resin blended with a tinting and/or pigmenting agent, to impart a color to the filaments and/or fibers that contrasts with the color of the filaments and/or fibers in first layer 280a. This may be desired for enhancing the visual impact of the ordered arrangement of changes in fiber and/or filament area density and basis weight between the attenuated regions 163 and the built-up regions 166 (see description below) of the web material. In one non-limiting example, filaments and/or fibers of the first layer 280a may include no tinting or pigmenting agents, while filaments and/or fibers of the second layer 281 may include one or more tinting or pigmenting agents. In another non-limiting example, filaments and/or fibers of the first layer 280*a* may include a whitening and/or opacifying agent (such as, for example, $TiO_2$), and filaments and/or fibers of the second layer may include a coloring agent such as a non-white pigmenting or tinting agent. It will be appreciated that these and other combinations of tinting, whitening, opacifying and/or pigmenting agents may be used to impart visible color contrast between first and second layers forming the web material. In still other examples, underlying materials such as materials forming the absorbent structure and/or the backsheet may include whitening, tinting or pigmenting agents selected to provide visual contrast with the topsheet. Pigmenting, whitening and/or opacifying agents may be obtained pre-dispersed in carrier resins, in color masterbatch products suitable for blending with filament component resin(s) prior to or during introduction into the extruder(s). The agent(s) selected are preferably solid, powdered compositions that do not dissolve in or react chemically with the polymer resins when blended and dispersed within the filament component resins as they are melted, extruded and spun into filaments under ordinary melt-spinning process conditions. Suitable pigmenting agents may include solid inorganic or organic compositions, and in some examples may be solid organometallic compositions.

Suitable white pigment masterbatch products typically include solid metallic and/or organometallic compositions, for example, Antimony White, Barium Sulfate, Lithopone, Cremnitz White, Titanium White ($TiO_2$), and Zinc White (ZnO).

In some examples, filaments forming the finished, formed nonwoven web material 280, or at least a first layer 280*a* thereof, may be spun from polymer resin(s) to which a blue pigmenting agent has been added. The inventors believe that an appropriate concentration of blue pigment added to the filament component resin may have a dramatic impact on visibility of the variances in basis weight and caliper in the ordered arrangement, enhancing the appearance of z-direction depth and overall three-dimensional structure. Without intending to be bound by theory, the inventors believe that other single pigments or combinations of pigments, admixed with the filament resin(s) to select weight percent concentrations, may have a similar effect on enhancing the visibility of apparent depth and/or visibility of three-dimensional structural features of the nonwoven web 280.

Suitable blue pigment masterbatch products typically also include solid metallic and/or organometallic compositions, for example, Ultramarine, Persian Blue, Cobalt Blue, Cerulean Blue, Egyptian Blue, Han Blue, Azurite, Prussian Blue, YImMn Blue and Manganese Blue. In a particular example, a blue color masterbatch product may be admixed to a concentration of approximately 0.25% of total weight polypropylene filament spinning resin, where the masterbatch product comprises approximately 36% by weight blue pigment composition. It is believed that an effective weight percent concentration of blue pigment material within the total spinning resin blend, for purposes of enhancing visibility of apparent depth and/or visibility of three-dimensional structural features of the nonwoven web 280 as described above, may be from approximately 0.03 percent to approximately 0.15 percent, more preferably from approximately 0.06 percent to 0.12 percent.

In yet another approach, an ink of a non-white color or color that contrasts with the spun filament color, may be applied via any suitable technique to the surface of the nonwoven web material that will become the absorbent-facing surface of a topsheet, to enhance visual impact as described above.

Process for Manufacturing Topsheet Material

Formed nonwoven web material from which topsheets as described above may be formed using equipment, processes and materials described in, for example, any of US application pub. nos. US 2017/0191198; US 2017/0029994; US 2017/0029993 and US 2017/0027774, and U.S. application Ser. Nos. 15/840,455; 15/879,474; 15/879,477; 15/881,910; 62/527,216; 62/527,224, 62/819,729; and 62/819,744, the disclosures of which are incorporated by reference herein.

Formed nonwoven web materials may be manufactured from spun filaments in a spunbond process, utilizing a specially adapted forming belt. The topsheet may be formed predominately of spunbond filaments or substantially entirely of spunbond filaments. Additional web loft and manufacturing efficiency may be achieved when the topsheet is formed of spunbond, bicomponent filaments. Bicomponent filaments may spun so as to have a side-by-side bicomponent configuration, such that suitable selection of differing resin components will impart crimp or curl to the filaments as they cool; crimp or curl of the filaments can help contribute to loft of the resulting web.

Topsheet Formation Process Components

Figure 11:
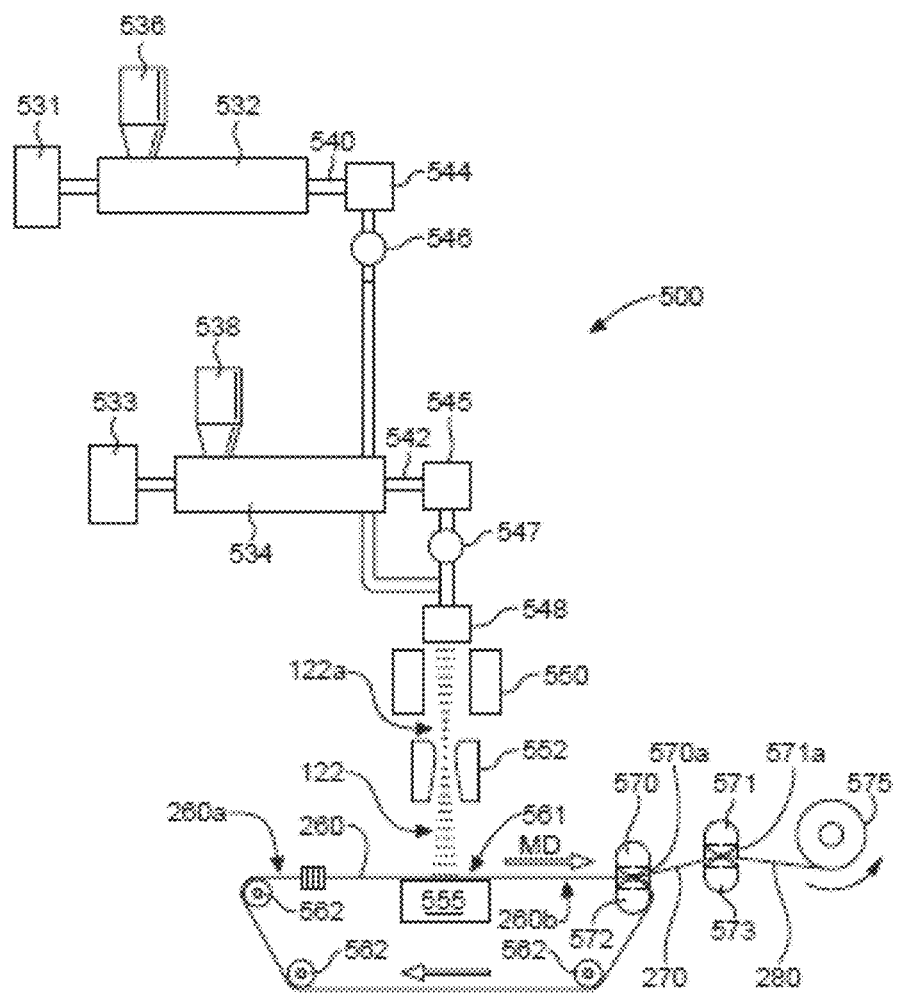
FIG. 11 is a schematic side-view illustration of an example of configuration of equipment for manufacturing a nonwoven web material.

For example, referring to FIG. 11, a process line 500 for manufacturing a formed nonwoven web material of bicomponent filaments may include a pair of melt extruders 532 and 534, driven by extruder drives 531 and 533, respectively, for separately melting and extruding a first polymer component resin and a second polymer component resin. The first polymer component resin may be fed into the respective extruder 532 from a first hopper 536 and the second polymer component resin may be fed into the respective extruder 534 from a second hopper 538. The first and second polymer component resins may be melted and driven by the extruders 532 and 534 through respective polymer conduits 540 and 542 then through filters 544 and 545, to melt pumps 546 and 547, which help pump the polymer into and through a spin pack 548. Spin packs with spinnerets used in spinning bicomponent filaments are known in the art and therefore are not described here in great detail. Generally described, a spin pack 548 may include a housing which includes a plurality of plates stacked one on top of the other with a pattern of openings arranged to create flow paths for directing the melted first and second polymer component resins separately through spinneret openings. The spin pack 548 may have spinneret openings arranged in one or more rows. As the melted polymer resins are forced through them, the spinneret openings emit a downward curtain of individual melted polymer streams 122*a*. For the purposes of the present disclosure, spinnerets may be arranged to form streams for sheath/core or side-by-side bicomponent filaments. Bicomponent filaments may be preferred in some circumstances for their particular characteristics. Side-by-side or eccentric or asymmetric core/sheath bicomponent filaments may be preferred where it is desired that the spun filaments have a spiral or curl imparted by differing cooling contraction rates of differing components, wherein spiral or curl in the spun filaments may contribute to enhanced loft and bulk of the nonwoven web material. Core/sheath bicomponent filaments may be preferred where it is desired that the respective components have differing attributes or properties that might be advantageously balanced. Such attributes or properties might include raw material (resin) cost, or spun tensile strength, or surface feel or surface friction. In one example, a core/sheath filament in which the core component is predominately polypropylene and the sheath component is predominately polyethylene may be preferred, wherein polypropylene is selected for the core component for its relatively lower cost and contribution to filament tensile strength, and polyethylene is selected for the sheath component for a relatively lower melting point (for purposes of thermal bonding between filaments) and a relatively lower-friction, silkier feel it imparts to the filament surfaces.

Although the above description contemplates spinning bicomponent filaments, it will be appreciated that the equipment and materials supplied may be adapted, selected and configured to spin monocomponent filaments, or multicomponent filaments having more than two components.

Spinnerets may be configured and adapted to form streams with generally circular cross-sections (to form filaments with generally round/circular cross sections), or streams with generally non-round cross sections such as asymmetric, multi-lobal, e.g., trilobal cross sections (to form asymmetric, lobed, e.g., trilobal filaments). Lobed filaments may be desired in some circumstances for their effects on fluid flow along their surfaces, for their effects on filament and nonwoven opacity, for their effects on fiber and nonwoven feel, or a combination of these effects. Generally, a nonwoven web material formed of lobed filaments such as trilobal filaments has greater opacity than an otherwise comparable nonwoven web material formed of round filaments, as a result of greater light refraction and/or diffusion through trilobal filaments. Fluid flow along filament surfaces may be enhanced or inhibited to a greater extent by lobed cross sections, depending upon whether the surfaces of the filaments are hydrophilic or hydrophobic, respectively.

The process line 530 also may include a quench blower 550 positioned beneath/adjacent the location the polymer streams 122a exit the spinnerets. Temperature, velocity and direction of air from the quench air blower 550 may be suitably controlled to quench the polymer streams, causing them to partially solidify. Quench air may be provided and directed at one (upstream or downstream) side of the curtain or both sides of the curtain.

An attenuator 552 may be positioned below the spinneret to receive the quenched polymer streams 122a. Filament draw units or aspirators for use as attenuators in melt spinning polymers are known in the art. Suitable filament draw units for use in the process of the present disclosure may include a linear filament attenuator of the type shown in U.S. Pat. No. 3,802,817, or eductive guns of the type shown in U.S. Pat. Nos. 3,692,618 and 3,423,266, the disclosures of which are incorporated herein by reference. Generally, the attenuator 552 may include and define an elongate vertical passage through which the polymer streams 122a may be entrained in a downward air stream, drawn downward, elongated and reduced in cross section to form filaments 122.

A shaped, at least partially foraminous, forming belt 260 may be positioned below the attenuator 552 and to receive the downward-moving continuous filaments from the outlet opening of the attenuator 552. The forming belt 260 is a continuous belt, having an outer receiving side 260a and an inner side 260b, and cycles about guide rollers 562, one or more of which may be driven at a controlled speed to cause the belt to translate along an x-y plane and along a machine direction MD through a working location 561 beneath the attenuator. A forming vacuum system 555 may be positioned below the working location 561 of the belt 260 where the filaments are deposited, to draw the air of the air stream through the belt, and thereby draw the entrained filaments toward and against the belt surface. Although the forming belt 260 is shown and described as a belt herein, it will be understood that a forming device with a suitable forming surface may also have other forms, such as a rotatable drum with a suitable cylindrical forming surface. Features of examples of shaped forming belts are described below. In operation of the process line 500, the hoppers 536 and 538 may be supplied with the respective desired first and second polymer component resin(s). First and second polymer component resin(s) may be melted by the respective extruders 532 and 534 and forced in their melted state through polymer conduits 540 and 542 to spin pack 548. The line may include filters 544, 545 to filter out solid impurities from the melted resins, and the line may also include supplemental melt pumps 546, 547 to increase pressure in the conduits and thereby assist in driving the polymer components to and through the spin pack 548. Although the temperatures of the melted polymer resins can be controlled and varied for the polymers used and desired process conditions, when one or both of polyethylene and polypropylene are predominately the component resins, the temperatures of the melted polymer resins may be controlled to be within a range from about 190 deg. C. to about 240 deg. C.

Topsheet Filament Spinning Resin Formulation

Non-limiting examples of particularly suitable polymeric resins for spinning bicomponent filaments contemplated herein include PH835 polypropylene obtained from LyondellBasell (Rotterdam, Netherlands) and Aspun-6850-A polyethylene obtained from Dow Chemical Company (Midland, Michigan, USA). Although polypropylene and polyethylene are contemplated as predominant polymer resin constituents for spinning filaments, for their thermodynamic and mechanical attributes combined with their costs at the present time, a wide variety of polymers may be suitable for use within the scope of the present disclosure. Other suitable examples include PP3155 and ACHIEVE 3854 products available from ExxonMobil, Irving, TX.

Non-limiting examples of potentially suitable synthetic polymers include thermoplastic polymers, such as polyesters, nylons, polyamides, polyurethanes, polyolefins (such as polypropylene, polyethylene and polybutylene), polyvinyl alcohol and polyvinyl alcohol derivatives, sodium polyacrylate (absorbent gel material), and copolymers of polyolefins such as polyethylene-octene or polymers comprising monomeric blends of propylene and ethylene, and biodegradable or compostable thermoplastic polymers such as polylactic acid, polyvinyl alcohol, and polycaprolactone. Potentially suitable natural polymers include starch, starch derivatives, cellulose and cellulose derivatives, hemicellulose, hemicelluloses derivatives, chitin, chitosan, polyisoprene (cis and trans), peptides and polyhydroxyalkanoates. In one example, a predominate polymer component for spinning filaments may be a thermoplastic polymer selected from the group consisting of: polypropylene, polyethylene, polyester, polylactic acid, polyhydroxyalkanoate, polyvinyl alcohol, polycaprolactone, styrene-butadiene-styrene block copolymer, styrene-isoprene-styrene block copolymer, polyurethane, and mixtures thereof. In another example, the thermoplastic polymer may be selected from the group consisting of: polypropylene, polyethylene, polyester, polylactic acid, polyhydroxyalkanoate, polyvinyl alcohol, polycaprolactone, and mixtures thereof. Alternatively, the polymer may comprise one derived from monomers which are partially produced by biological processes, such as bio-polyethylene or bio-polypropylene.

In some circumstances it may be desired to manipulate and/or the enhance features of the spun filaments such as color, opacity, pliability, hydrophilicity/hydrophobicity and/or surface feel (e.g., surface coefficient of friction) of fibers spun from the component resin(s). In such circumstances one or more melt additives may be included with the resin(s) fed to the extruder(s).

Inorganic fillers such as the oxides of magnesium, aluminum, silicon, and titanium may be added to the polymer resins as whiteners, opacifiers, fillers or processing aides. Other inorganic materials include hydrous magnesium silicate, titanium dioxide, calcium carbonate, clay, chalk, boron nitride, limestone, diatomaceous earth, mica glass quartz, and ceramics.

Topsheet Filament Surface Property Manipulation

Slip agent melt additives may be included in an amount sufficient to affect and/or enhance desired haptic properties (e.g., impart a soft/silky/slick feel) to the filaments. Some slip agents when melt-blended with the resin gradually migrate to the filament surfaces during cooling or after fabrication, hence forming a thin coating with lubricating effects, in the filament surfaces. It may be desired that the slip agent be a fast-bloom slip agent and can be a hydrocarbon having one or more functional groups selected from hydroxide, aryls and substituted aryls, halogens, alkoxys, carboxylates, esters, carbon unsaturation, acrylates, oxygen, nitrogen, carboxyl, sulfate and phosphate. In one particular form, the slip agent is a salt derivative of an aromatic or aliphatic hydrocarbon oil, notably metal salts of fatty acids, including metal salts of carboxylic, sulfuric, and phosphoric aliphatic saturated or unsaturated acid having a chain length of 7 to 26 carbon atoms, preferably 10 to 22 carbon atoms. Examples of suitable fatty acids include the monocarboxylic acids lauric acid, stearic acid, succinic acid, stearyl lactic acid, lactic acid, phthalic acid, benzoic acid, hydroxystearic acid, ricinoleic acid, naphthenic acid, oleic acid, palmitic acid, erucic acid, and the like, and the corresponding sulfuric and phosphoric acids. Suitable metals include Li, Na, Mg, Ca, Sr, Ba, Zn, Cd, Al, Sn, Pb and so forth. Representative salts include, for example, magnesium stearate, calcium stearate, sodium stearate, zinc stearate, calcium oleate, zinc oleate, magnesium oleate and so on, and the corresponding metal higher alkyl sulfates and metal esters of higher alkyl phosphoric acids.

In other examples, the slip agent may be a non-ionic functionalized compound. Suitable functionalized compounds include: (a) esters, amides, alcohols and acids of oils including aromatic or aliphatic hydrocarbon oils, for example, mineral oils, naphthenic oils, paraffinic oils; natural oils such as castor, corn, cottonseed, olive, rapeseed, soybean, sunflower, other vegetable and animal oils, and so on. Representative functionalized derivatives of these oils include, for example, polyol esters of monocarboxylic acids such as glycerol monostearate, pentaerythritol monooleate, and the like, saturated and unsaturated fatty acid amides or ethylenebis(amides), such as oleamide, erucamide, linoleamide, and mixtures thereof, glycols, polyether polyols like Carbowax, and adipic acid, sebacic acid, and the like; (b) waxes, such as carnauba wax, microcrystalline wax, polyolefin waxes, for example polyethylene waxes; (c) fluoro-containing polymers such as polytetrafluoroethylene, fluorine oils, fluorine waxes and so forth; and (d) silicon compounds such as silanes and silicone polymers, including silicone oils, polydimethylsiloxane, amino-modified polydimethylsiloxane, and so on.

Fatty amides that may be useful for purposes of the present disclosure are represented by the formula: RC(O)NHR[1], where R is a saturated or unsaturated alkyl group having 7 to 26 carbon atoms, preferably 10 to 22 carbon atoms, and R1 is independently hydrogen or a saturated or unsaturated alkyl group having from 7 to 26 carbon atoms, preferably 10 to 22 carbon atoms. Compounds according to this structure include for example, palmitamide, stearamide, arachidamide, behenamide, oleamide, erucamide, linoleamide, stearyl stearamide, palmityl palmitamide, stearyl arachidamide and mixtures thereof.

Ethylenebis(amides) that may be useful for purposes of the present disclosure are represented by the formula:

RC(O)NHCH$_2$CH$_2$NHC(O)R, where each R is independently is a saturated or unsaturated alkyl group having 7 to 26 carbon atoms, preferably 10 to 22 carbon atoms. Compounds according to this structure include for example, stearamidoethylstearamide, stearamidoethylpalmitamide, palmitamidoethylstearamide, ethylenebisstearamide, ethylenebisoleamide, stearylerucamide, erucamidoethylerucamide, oleamidoethyloleamide, erucamidoethyloleamide, oleamidoethylerucamide, stearamidoethylerucamide, erucamidoethylpalmitamide, palmitamidoethyloleamide and mixtures thereof.

Commercially available examples of fatty amides include Ampacet 10061 (Ampacet Corporation, White Plains, New York, USA) which comprises 5 percent of a 50:50 mixture of the primary amides of erucic and stearic acids in polyethylene; Elvax 3170 (E.I. du Pont de Nemours and Company/DuPont USA, Wilmington, Delaware, USA) which comprises a similar blend of the amides of erucic and stearic acids in a blend of 18 percent vinyl acetate resin and 82 percent polyethylene. Slip agents also are available from Croda International Plc (Yorkshire, United Kingdom), including Crodamide OR (an oleamide), Crodamide SR (a stearamide), Crodamide ER (an erucamide), and Crodamide BR (a behenamide); and from Crompton, including Kemamide S (a stearamide), Kemamide B (a behenamide), Kemamide O (an oleamide), Kemamide E (an erucamide), and Kemamide (an N,N'-ethylenebisstearamide). Other commercially available slip agents include Erucamid ER erucamide.

Other suitable melt additives for softness/reduction of the coefficient of friction include erucamide, stearamide, oleamide, and silicones e.g. polydimethylsiloxane. Some specific examples include CRODAMIDE slip & anti-block agents from Croda International Plc (Yorkshire, United Kingdom), and slip BOPP agents from Ampacet Corporation (White Plains, New York, USA). Some additional specific examples of softness/reduction of the coefficient of friction melt additives specifically tailored for polypropylene are available from Techmer PM Company (Clinton, Tennessee, USA).

Nonwoven web materials within contemplation of the present disclosure may include slip agents/softness melt additives independently, or in conjunction with other additives that affect the surface energy (hydrophilicity/hydrophobicity), or in conjunction with other filament feature variations including but not limited to filament size, filament cross-sectional shape, filament cross-sectional configuration, and/or curled filament variations. For examples of nonwoven web materials including two or more web layers, or two or more deposited layers of differing filaments, additives may be included in filaments of one layer but not the other, or differing additives may be included in filaments of differing layers.

As noted herein, in some examples it may be desired that filaments present at and proximate to the absorbent-facing surface 123 of the topsheet have hydrophilic surface energy properties. To impart the filaments with such properties, they may be spun from one or more resin(s) inherently having such properties, or alternatively, they may be spun from resin(s) blended with a melt additive that renders the resulting spun filaments hydrophilic. Alternatively, after spinning, the filaments, the batt or the finished web may be treated with a material such as a surfactant renders them hydrophilic. This may be desired for purposes of selectively imparting portions of the topsheet (such as the absorbent-facing surface 123) with hydrophilicity, to affect its fluid handling characteristics.

In conjunction therewith, it may be desired that filaments present within the topsheet at locations more removed from the absorbent-facing surface 123, including filaments present at and proximate to the wearer-facing surface 124, be spun from inherently hydrophobic resin, or additionally or alternatively, be spun from resin blended with a melt additive that renders the resulting spun filaments hydrophobic, or enhances hydrophobicity. Inherent and/or enhanced hydrophobicity of filaments as spun may help prevent unwanted migration of an applied solution, emulsion or concentrate of surfactant in a z-direction from the absorbent-facing surface toward the wearer-facing surface, and may also enhance the capability of the filaments in built-up regions 166 of the topsheet to serve as barriers to migration of aqueous body exudate across the topsheet along a direction in the x-y plane, toward the outer edges of the pad. Hydrophobicity of filaments may be enhanced via addition of hydrophobizing melt additives to the resin(s) from which the filaments are to be spun.

In some examples, a hydrophobizing melt additive may be added directly or as master batch to the polymer melt during the spinning process. Suitable melt additives may include, for example, lipid esters or polysiloxanes. When a hydrophobizing melt additive is blended into resin(s), the additive in the resulting spun filament can bloom to its external surface and create a film covering portions of the surface, form fibrils, flakes, particles, or other surface features that have low surface energy.

Any suitable hydrophobizing melt additive may be utilized. Examples of hydrophobizing melt additives include fatty acids and fatty acid derivatives. The fatty acids may originate from vegetable, animal, and/or synthetic sources. Some fatty acids may range from a C8 fatty acid to a C30 fatty acid, or from a C12 fatty acid to a C22 fatty acid. In other forms, a substantially saturated fatty acid may be used, particularly when saturation arises as a result of hydrogenation of fatty acid precursor. Examples of fatty acid derivatives include fatty alcohols, fatty acid esters, and fatty acid amides. Suitable fatty alcohols (R—OH) include those derived from C12-C28 fatty acids.

Suitable fatty acid esters include those fatty acid esters derived from a mixture of C12-C28 fatty acids and short chain (C1-C8, preferably C1-C3) monohydric alcohols preferably from a mixture of C12-C22 saturated fatty acids and short chain (C1-C8, preferably C1-C3) monohydric alcohols. The hydrophobizing melt additive may comprise a mixture of mono, di, and/or tri-fatty acid esters. An example includes fatty acid ester with glycerol as the backbone as illustrated in illustration [1], below:

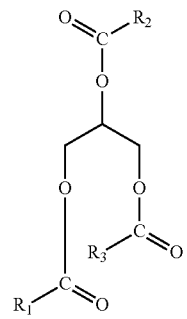

[1]

where R1, R2, and R3 each is an alkyl ester having carbon atoms ranging from 11 to 29. In some forms, the glycerol derived fatty acid ester has at least one alkyl chain, at least two, or three chains to a glycerol, to form a mono, di, or triglyceride. Suitable examples of triglycerides include glycerol thibehenate, glycerol tristearate, glycerol tripalmitate, and glycerol trimyristate, and mixtures thereof. In the case of triglycerides and diglycerides, the alkyl chains could be the same length, or different length. Example includes a triglyceride with one alkyl C18 chain and two C16 alkyl chain, or two C18 alkyl chains and one C16 chain. Preferred triglycerides include alkyl chains derived from C14-C22 fatty acids.

Suitable fatty acid amides include those derived from a mixture of C12-C28 fatty acids (saturated or unsaturated) and primary or secondary amines A suitable example of a primary fatty acid amide includes those derived from a fatty acid and ammonia as illustrated in illustration [2], below:

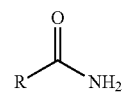

[2]

where R has a number of carbon atoms ranging from 11 to 27. In at least one other form, the fatty acids may range from a C16 fatty acid to a C22 fatty acid. Some suitable examples include erucamide, oleamide and behanamide Other suitable hydrophobizing melt additives include hydrophobic silicones. Additional suitable hydrophobizing melt additives are disclosed in U.S. patent application Ser. No. 14/849,630 and U.S. patent application Ser. No. 14/933,028. Another suitable hydrophobizing melt additive is available from Techmer PM in Clinton, Tenn. under the trade name PPM17000 High Load Hydrophobic. One specific example of a hydrophobizing melt additive is glycerol tristearate. As used herein, glycerol tristearate is defined as a mixture of long-chained triglycerides containing predominately C18 and C16 saturated alkyl chain lengths. Additionally, there could be varying degrees of unsaturation and cis to trans unsaturated bond configurations. The alkyl chain lengths could range from about C10 to about C22. The degrees of unsaturation typically will range from 0 to about 3 double bonds per alkyl chain. The ratio of cis to trans unsaturated bond configurations can range from about 1:100 to about 100:1. Other suitable examples for use with polypropylene and/or polyethylene, a triglyceride which contains either stearic acid or palmic acid or both as the fatty acid components, or a mixture of such triglycerides. Other suitable hydrophobizing melt additives may comprise erucamide or polysiloxanes.

As noted herein, in some examples, it may be desired that constituents of the web material include filaments having surface energy properties that make them hydrophilic. As noted, it may be desired in some circumstances that filaments forming and proximate to the absorbent-facing surface of the topsheet have hydrophilic surfaces. In some examples this may be accomplished via use of hydrophilizing melt additives to the resin(s) from which filaments are spun.

Any suitable hydrophilizing additive can be used. Some suitable examples include those available from Techmer PM, Clinton, Tennessee sold under the trade name of TECHMER PPM15560; TPM12713, PPM19913, PPM 19441, PPM19914, PPM112221 (for polypropylene), PM19668, PM112222 (for polyethylene). Additional examples are available from Polyvel Inc. located in Hammonton, N.J., sold under the trade name of POLYVEL VW351 PP Wetting Agent (for polypropylene); from Goulston Technologies Inc. located in Monroe, N.C. sold under the trade name HYDROSORB 1001; as well as those hydrophilizing additives disclosed in U.S. Patent Application Publication No. 2012/0077886 and U.S. Pat. Nos. 5,969,026 and 4,578,414.

Nucleating agents may be included along with melt additives. Nucleating agents can help to drive more or faster blooming of either a hydrophilizing or hydrophobizing melt additive. A nucleating agent when melt-blended with constituent resin(s) and a hydrophilizing or hydrophobizing melt additive will enhance the hydrophilizing or hydrophobizing effect or wetting contact angle effect in the filaments (depending on the type of additive), as compared with the same hydrophilizing or hydrophobizing melt-additive used without a nucleating agent. Suitable nucleating agents may include a nonitol, a trisamide and/or a sorbitol-based nucleating agent. Specific but non-limiting examples include: organic nucleation agents such as MILLAD NX 8000 or (in its new trade name) NX ULTRACLEAR GP110B from Milliken & Company, Spartanburg, South Carolina. An example of an effective inorganic nucleating agent is $CaCO_3$, or other and especially nano-clay or nano-scale mineral molecules.

Some melt additives may serve to enhance tactile softness and/or reduce surface coefficient of friction, as well as modify surface energy, and thereby serve dual purposes. For example, fatty amides when used as melt additives may serve to both reduce surface friction and enhance hydrophobicity of the filaments. These melt additives are listed herein under hydrophobic melt additives. Other non-limiting examples of potentially suitable softness-enhancing and hydrophobizing melt additives are identified in US 2017/0258651.

During manufacture or in a post-treatment or even in both, the formed nonwoven web materials contemplated herein may be treated with surfactants or other agents to either hydrophilize the material or make it hydrophobic. This is known in the fields of manufacturing and converting nonwoven web materials used to make components of absorbent articles. For example, a formed nonwoven web material used for a topsheet may be treated with a surfactant or other hydrophilizing agent so as to make it more receptive and/or permeable by aqueous body exudates such as urine. For other absorbent articles, the topsheet may allowed to remain at its naturally hydrophobic state or be made even more hydrophobic, through the addition of a hydrophobizing material or surfactant.

Spinning

As the polymer streams 122*a* exit the spinnerets, a stream of quenching air from the quench blower 550 at least partially quenches the polymers forming the streams, and, for certain polymers, induces crystallization in the polymers. To increase the rate of crystallization/solidification if desired, the quench blower(s) may be configured to direct quench air in a direction approximately perpendicular to the length of the streams. The quenching air may be cooled or heated as deemed suitable to be at a temperature of about 0 deg. C. to about 35 deg. C. and a velocity from about 100 to about 400 feet per minute when it contacts the polymer streams. The streams may be quenched sufficiently to reduce their surface tackiness so as to prevent them from bonding or fusing together to any undesirable extent, upon contact therebetween, as they travel to and are deposited and accumulate on the forming belt 260.

After quenching, the polymer streams 122*a* may be drawn into the vertical passage of an attenuator 552 and entrained by downward air flow generated by the attenuator 552. The attenuator may in some examples be positioned 30 to 60 inches below the bottom of the spinnerets. The air flow generated by the attenuator moves at a higher downward velocity than that of the entering quenched polymer streams. The attenuating air flow entrains the polymer streams and draws them downwardly, and thereby elongates and reduces their cross sections, thereby forming filaments 122.

The filaments 122 exit the attenuator 552 and travel downwardly substantially in a z-direction with respect to the cycling forming belt 260 having an upward-facing portion moving along the machine direction MD through the working location 561, beneath the attenuator 552. The entraining air exiting the attenuator may be drawn through the air-permeable portions of the forming belt 260 by the forming vacuum system 555, and the filaments 122 are stopped in their z-direction travel by the outer receiving side 260*a* of the forming belt 260, are deposited and accumulated thereon, and then travel with the forming belt 260 in the machine direction along therewith. It will be appreciated that the rate of deposit and accumulation of the filaments on the forming belt 260 may be controlled by controlling the speed at which the forming belt is cycled, the rate at which the filaments are spun, or a combination of these. As will be further explained below, the forming belt 260 may be configured with features that affect localized rates and depths of accumulation of filaments across its overall surface area in the x-y plane, to result in formation of a batt of filaments 270 and subsequent finished nonwoven web material 280 with a desired ordered arrangement of regions of varying basis weight and/or filament area density and/or thickness or caliper.

In some circumstances it may be desired to include discrete filaments of differing compositions in the nonwoven web material. It will be appreciated that this may be accomplished by configuring equipment carrying differing polymer resins arranged in parallel or in series/sequentially to one or more combinations of spin pack(s), quenching equipment and attenuating equipment configured to spin filaments and direct them at the forming belt. In one non-limiting example, it may be desired that the nonwoven web material has layered deposits of filaments of differing compositions with differing levels of hydrophilicity/hydrophobicity. Referring to FIG. 21, in a particular example, it may be desired that hydrophobic filaments are predominately present proximate the wearer-facing surface 124 of a topsheet material, while hydrophilic filaments are predominately present proximate the absorbent-facing surface 123. It will be appreciated that, to produce such a configuration, the filament spinning equipment may be configured to spin and deposit a first layer 280*a* of hydrophobic filaments onto the forming belt, and sequentially downstream in the process, to spin and deposit a second layer 281 of differing, hydrophilic filaments over the hydrophobic filaments, as the batt moves along a machine direction on the moving forming belt.

Compaction and Bonding

The process line 500 may further include one or more consolidating devices such as compaction rolls 570 and 572, which form a nip 570a through which the batt 270 may be compacted. Optionally, one or both compaction rolls 570, 572 may be heated to promote partial softening and plastic deformation of the filaments. It may be desired, further, to apply a combination of heat and pressure to the filaments in the nip 570a sufficient to induce some bonding between intermeshing/crossing filaments traveling through nip 570a.

Compaction facilitates neat removal of the batt 270 from the forming belt, and some bonding may enhance this effect as well as impart added machine- and/or cross-direction tensile strength to the finished material. The compaction rolls 570, 572 may be a pair of smooth surface stainless steel rolls with independent heating controllers. One or both compaction rolls may be heated by electric elements or hot oil circulation. The gap between the compaction rolls may be controlled, e.g., hydraulically, to impose desired pressure on the batt as it passes through the nip 570a. In one example, with a forming belt caliper of 1.4 mm, and a spunbond nonwoven having a basis weight of 30 gsm, the nip gap between the compaction rolls 570, 572 may be about 1.35 to 1.50 mm.

In one example, upper compaction roll 570 may be heated to a temperature sufficient to induce melting of bond filaments on the upper surface of the batt 270, to impart cohesion and strength to the batt that may facilitate its removal from forming belt 260 without losing integrity. As shown in FIG. 11, for example, as rolls 570 and 572 rotate, forming belt 260 with the batt laid down on it enter the nip 570a between rolls 570 and 572. Heated roll 570 can heat the portions of nonwoven fabric 10 that are pressed against it most closely, by land surfaces 262a of airflow blocking structures 262 on forming belt 260 (described below), to deform and/or flatten and/or bond filaments proximate the upper surface (i.e., attenuator-side) surface of batt 270, to an extent desired. As can be understood by the description herein, the attenuated regions in which filaments are so deformed will reflect the pattern of the airflow blocking structures 262 on forming belt 260.

After compaction, the compacted batt may be lifted away or separated from the forming belt 260 and be directed through a second nip 571a formed by calender rolls 571, 573. The calender rolls 571, 573 may be stainless steel rolls, one having an engraved or otherwise formed pattern of raised bonding protrusions about its cylindrical surface (bonding roller), and the other being a smooth roll (anvil roller). The bonding roller, or both bonding and anvil rollers, may be heated such that they heat and partially melt the filaments so as to cause them to fuse together in the nip, between the radially outermost surfaces of the bonding protrusions and the anvil roller. The bonding protrusions on the bonding roller may be configured in any suitable regular pattern of relatively closely-spaced bonding "pins" that will effect a like pattern of point bonds in the finished web material 280. The radially outermost surfaces of the bonding protrusions effect localized elevated compression of the batt in the nip 571a, between the bonding protrusions and the anvil roller. These surfaces may have a cumulative surface area about the bonding roller that amounts to a percent fraction of the total cylindrical surface area of the working portion of the bonding roller (bonding area percentage), which will be approximately reflected in the percent fraction of the surface area, in the x-y plane, of the web material that is bonded (bonded area percentage). The bonding area percentage of the bonding roller, and the resulting bonded area percentage of the web material, may be approximately from 3% to 30%, from 6% to 20%, or from 7% to 15%. A pattern of thermal calender point-bonds may serve to improve cohesiveness of the web and enhance machine direction and cross-direction tensile strength and dimensional stability, useful in downstream processing and incorporation of the formed nonwoven web material into finished products.

Additionally or alternatively, in some examples the batt may be bonded via a hot air bonding process. Through-air thermal bonding may be another approach to create higher loft nonwoven structures which may be desired in some circumstances. Through-air thermal bonding involves the application of hot air to the surface of the filament batt. The hot air flows through holes in a plenum positioned just above the nonwoven. However, the air is not pushed through the nonwoven, as in common hot air ovens. Negative pressure or suction pulls the air through the open conveyor apron that supports the nonwoven as it passes thorough the oven. Pulling the air through the nonwoven fabric allows much more rapid and even transmission of heat and minimizes fabric distortion. As an alternative to use of a conventional through-air bonding unit, it is contemplated placing the bonding unit over the forming belt 260 while a vacuum is operated beneath the belt to draw hot air through the batt, effecting a process similar to that effected by a conventional through-air bonding unit.

Forming Belt Manufacture

A forming belt 260 may be made according to the methods and processes described in U.S. Pat. Nos. 6,610,173; 5,514,523; 6,398,910; or US 2013/0199741, each with the improved features and patterns disclosed herein for making spunbond nonwoven webs. The '173, '523, '910 and '741 disclosures describe belts that are representative of papermaking belts made with cured resin on a belt substrate member, which belts, with improvements and suitable configurations, may be utilized as described herein.

A forming belt 260 having three-dimensional features and patterns for making spunbond nonwoven webs may also be made by the following methods and processes and/or on the following apparatuses, including with modifications as desired for structures taught herein: rotary screen processes as taught in U.S. Pat. No. 7,799,382; polymer extrusion as taught in US 2007/0170610; resin system grafting as taught in U.S. Pat. No. 7,105,465; perforated film as taught in U.S. Pat. No. 8,815,057; successive layer treatment as taught in US 2006/0019567; polymeric droplet deposition as taught in U.S. Pat. No. 7,005,044; polymeric droplet deposition with a sacrificial material as taught in U.S. Pat. No. 7,014,735; air permeable film technology as taught by U.S. Pat. No. 8,454,800 or U.S. Pat. No. 8,822,009; multilayer belt structures as taught in US 2016/0090692; laser etching as taught by U.S. Pat. No. 8,758,569 or 8,366,878; extruded mesh technology as taught in US 2014/0272269; nonwoven belts as described in US 2008/0199655; and additive manufacturing methods and processes as taught in US 2015/0102526A1, or US 2016/0159007, or WO 2016/085704, or US 2016/0185041.

Figure 12:
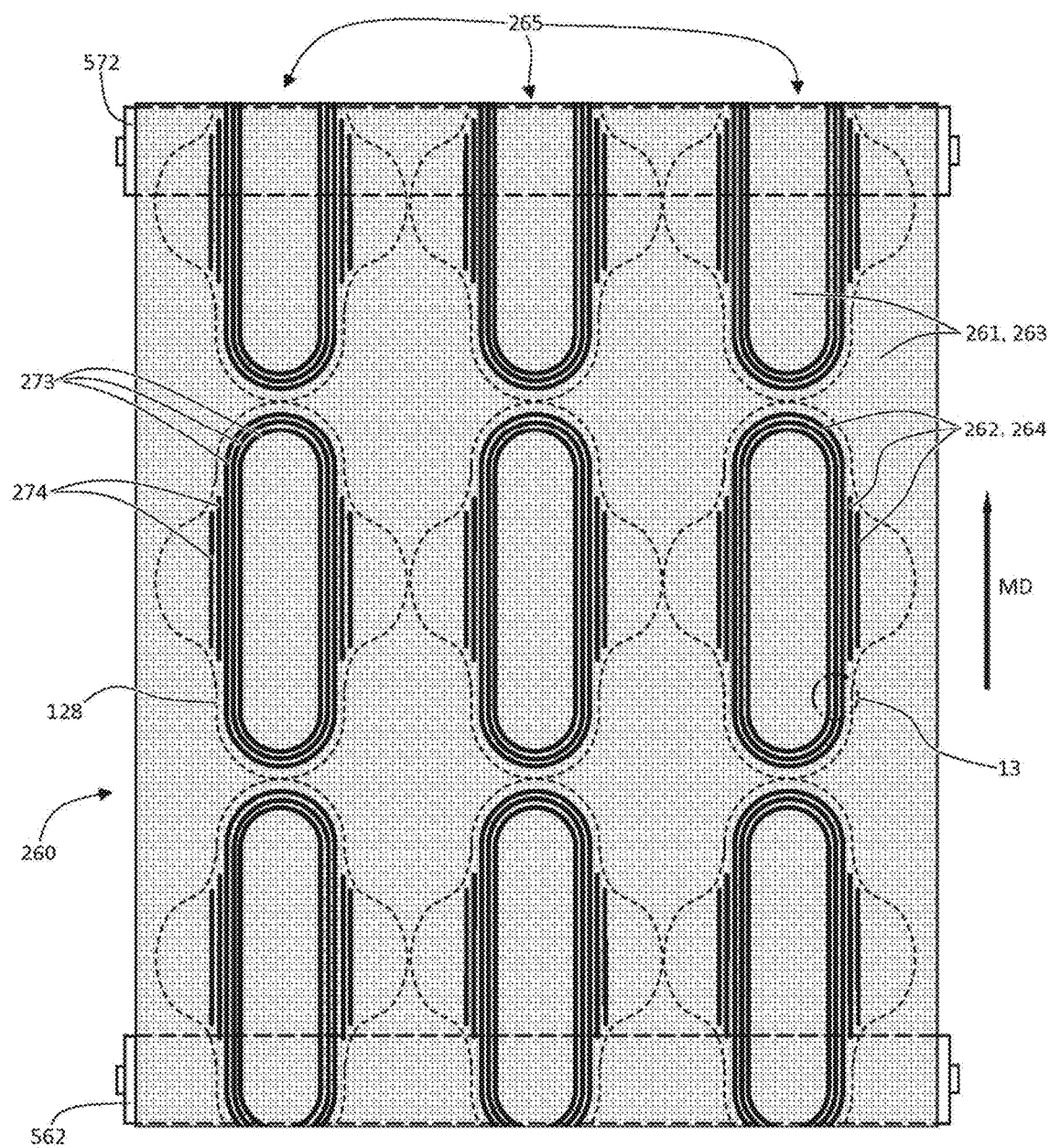
FIG. 12 is a schematic plan view of an example of a portion of a forming belt receiving side as it might appear with the belt disposed about guide/drive rollers.
Figure 13:
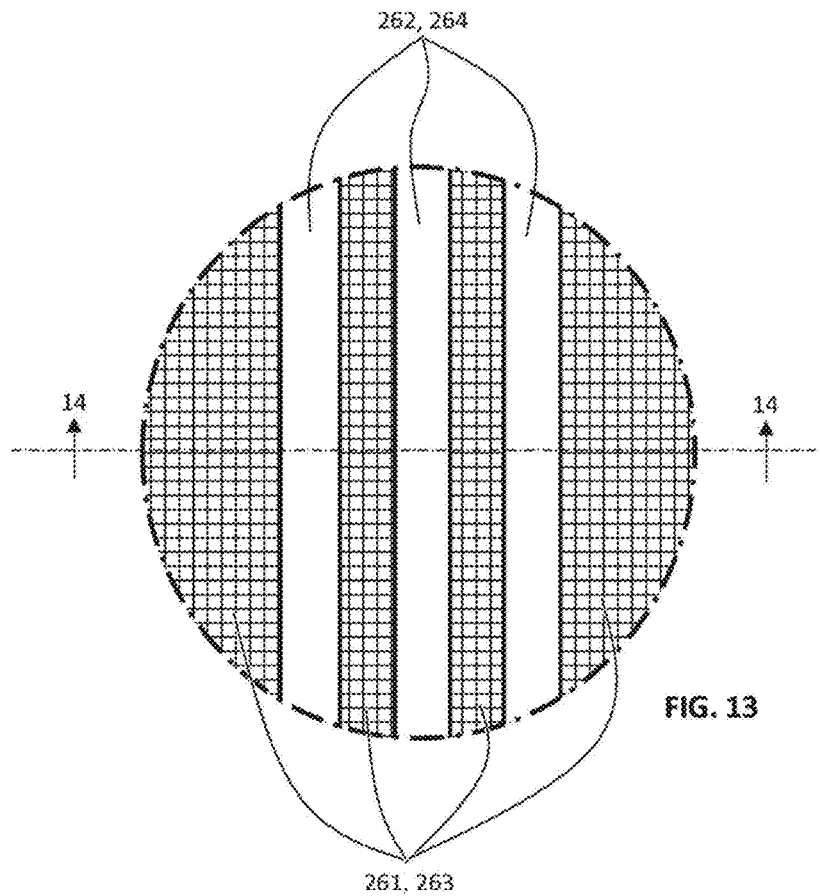
FIG. 13 is an expanded schematic view of the portion of the forming belt receiving side identified as "13" in FIG. 12.
Figure 14:
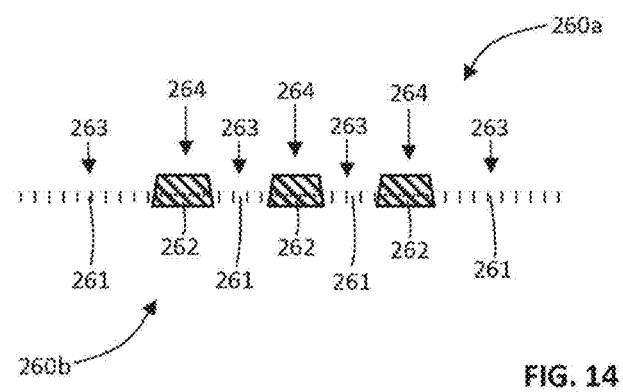
FIG. 14 is a schematic lateral cross section of the portion of the forming belt shown in FIG. 13.

An example of a forming belt 260 of the type useful for purposes of the present disclosure and which may be made according to the disclosure of U.S. Pat. No. 5,514,523, is schematically depicted in FIGS. 12-14. As taught in the '523 patent, a flat sheet of substrate belt material 261 is thoroughly coated with a liquid photosensitive polymeric resin to a preselected thickness. The substrate belt material 261 (called a "reinforcing structure" in the '523 patent) may be an air-permeable wire mesh or screen material, a woven mat or sheet material, an apertured metal or polymer sheet material, or any other material that provides suitable process dimensional stability and durability under conditions of use contemplated herein, and a relatively high degree of air permeability in a z-direction combined with a relatively small spacing and sizing of air passageways, such that spun filaments striking the belt will accumulate thereon rather than being blown or drawn through air passageways to any substantial extent, by air moving therethrough in the z-direction. A transparent film or mask printed with, or otherwise reflecting in the negative, opaque portions defining a desired pattern, arrangement, sizes and shape(s) for desired airflow blocking structures 262, is laid down over the liquid photosensitive resin. The resin is then exposed to light of an appropriate wavelength through the film, such as UV light for a UV-curable resin. This exposure to light causes curing of the resin beneath the transparent portions (e.g., non-printed portions) of the mask. Uncured resin (beneath the opaque portions in the mask) may then be removed from the substrate (e.g., via use of a solvent), leaving behind solid, airflow blocking structures formed of the cured resin formed on the substrate, arranged in the desired pattern and shape(s), for example, the pattern of airflow blocking structures 262 shown in FIG. 12. Other patterns of airflow blocking structures for imparting any desired decorative or functional features to a nonwoven web material can also be formed. Airflow blocking structures 262 form and define airflow blocked regions 264 of forming belt 260, through which z-direction air flow through the belt is blocked. The portions of the substrate belt material 261 on which the resin was left uncured, and from which it was removed, form and define airflow permeable regions 263 of forming belt 260, through which z-direction air flow through the belt is permitted. The resin may be formed and cured on the belt to a depth and in a manner such that airflow blocking structures 262 have a desired z-direction depth, and flat land surfaces 262a generally along an x-y plane. Following formation of the airflow blocking structures, ends of the sheet of substrate belt material with the airflow blocking structures formed thereon may be joined in any suitable manner to form a continuous forming belt 260.

Batt and Web Formation

Figure 15:
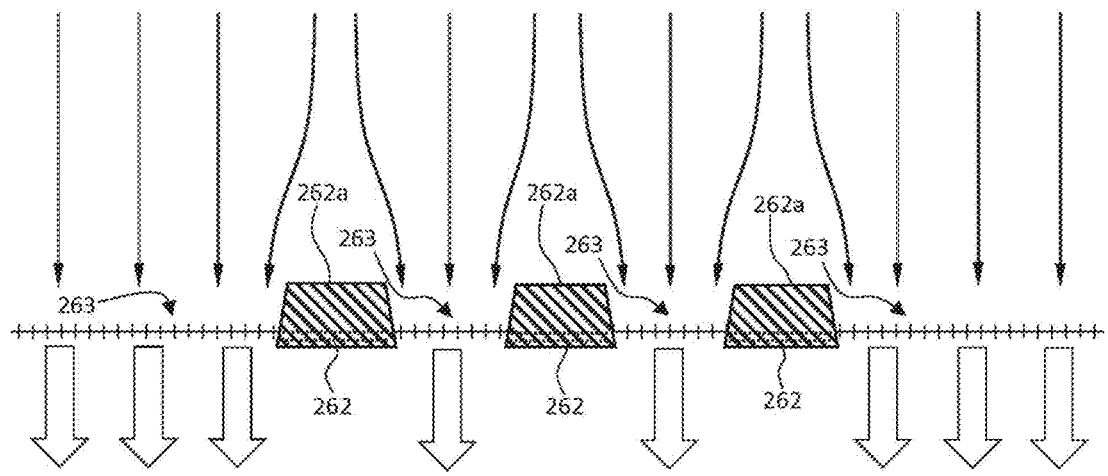
FIG. 15 is an expanded schematic view of the cross section of FIG. 14, illustrating the general directions of filament travel to, and air flow through, the forming belt when in operation.
Figure 16:
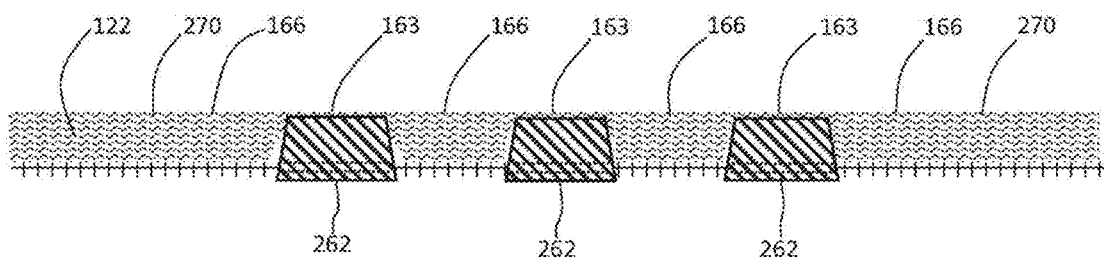
FIG. 16 is a schematic lateral cross section view of filament accumulation on the portion of the forming belt as shown in FIG. 15, following deposition of filaments thereon to form a batt.
Figure 17:
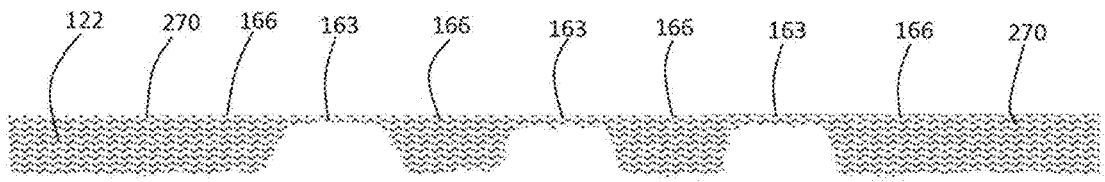
FIG. 17 is a schematic lateral cross section view of a batt of filaments formed on the portion of a forming belt shown in FIG. 16, following removal therefrom.

FIGS. 15-17 illustrate the manner in which spun filaments may be accumulated on forming belt 260, with the location and depth of filament accumulation being affected by the arrangement and depth of airflow blocking structures 262 on the forming belt. Because the filaments are entrained in attenuating air being driven downward and drawn through the belt in the z-direction by the forming vacuum system 555 (see FIG. 11) they follow the air as it finds its way around and past the blocking structures 262 and are deposited predominately on/over airflow permeable regions 263 of the forming belt. Accordingly, the filaments accumulate to a greater depth and/or filament area density and weight over the airflow permeable regions 263, to form built-up regions 166 of a batt 270 of filaments accumulated on the belt. As previously noted, the extent of filament accumulation on the forming belt, generally, may be controlled by controlling the belt cycling speed and the filament spinning rate, or a combination thereof. Turbulence and resulting randomness in the air flow as it approaches the belt, and machine direction movement of the belt, will cause a smaller accumulation of filaments (which are generally continuous as spun) crossing over and thereby accumulating to a lesser extent over the land surfaces 262a of the airflow blocking structures 262, forming attenuated regions 163 in the batt 270 of accumulated filaments. This effect is schematically illustrated in FIG. 9, which depicts a relatively small accumulation of filaments 122 crossing through channel portions 164, as they may be formed by appropriately configured airflow blocking structures, and also in FIG. 16. The relative distribution of filaments between attenuated regions 163 and built-up regions 166, and resulting relative basis weights therebetween, may be adjusted at least in part by regulating the air flow rate drawn through the forming belt 260 by the forming vacuum system 555. Generally, a relatively lesser number of filaments will accumulate over the land surfaces 262a of the airflow blocking structures 262, and a relatively greater number of filaments will accumulate over the airflow permeable regions 263, with a relatively greater air flow rate into vacuum system 555—and vice versa. Alternatively or in combination with regulation of air flow rate drawn by the forming vacuum system 555, the relative distribution of filaments between the attenuated regions 163 and the built-up regions 166 may be controlled by selection of the substrate forming belt material 261. Generally, a relatively lesser number of filaments will accumulate over the land surfaces 262a of the airflow blocking structures 262, and a relatively greater number of filaments will accumulate over the airflow permeable regions 263, with a relatively greater air permeability of the substrate belt material 261 and consequently, of the airflow permeable regions 263, of the forming belt 260—and vice versa.

Following compaction between compaction rollers 571, 572 (shown in FIG. 11) and subsequent removal from the forming belt, as illustrated in FIG. 17 the batt 270 will have a structure with built-up regions 166 and attenuated regions 163 substantially corresponding to the arrangement of airflow blocking structures on the forming belt. As noted, filaments and/or portions thereof occupying the attenuated regions 163 may be somewhat plastically deformed (e.g., flattened) as a result of compaction between compaction roller 570 and the land surfaces 262a of the airflow blocking structures 262. Correspondingly, filaments and/or portions thereof occupying the built-up regions 166 generally will not be deformed by compaction or may be deformed to a substantially lesser extent, because during compaction they are disposed in the spaces between the airflow blocking structures and thus are not so closely compressed as the batt passes through compaction nip 270a.

Using a forming belt 260 and process as described above, a difference between the fiber and/or filament area density, and/or the basis weight, of the batt, of the built-up regions versus the attenuated regions can be achieved to a level of 2:1, 3:1 or even 4:1 or greater. The overall basis weight of the nonwoven material can be between about 10 gsm to about 50 gsm, more preferably from about 15 gsm to about 40 gsm, or most preferably from about 20 gsm to about 35 gsm, specifically reciting all values within these ranges and any ranges created thereby.

As noted herein the diameter of the filaments may be about 18 microns. However, other filament diameters are contemplated. For example, filament diameters can be about 10 microns to about 30 microns or more preferably from about 15 microns to about 20 microns, specifically reciting all values within these ranges or any ranges created thereby. From the description above and the figures, it will also be appreciated that a formed nonwoven web material manufactured according to the process described will exhibit "sidedness," meaning a difference between features of the surface that will be comprised by a wearer-facing surface of a topsheet, and features of the opposing surface that will be comprised by an absorbent-facing surface of the topsheet. Referring to FIGS. 16 and 17, for example, it will be appreciated that the surface of the batt (and subsequent nonwoven web material) formed by filaments that reached the forming belt first in time (first-formed surface) will exhibit topographic features and/or texture, according to the ordered arrangement, that have substantially greater z-direction depth, than any topographic features and/or texture of the opposing surface, i.e., the surface formed by filaments that reached the forming belt last in time (last-formed surface), prior to compaction of the batt. As a result of such sidedness, visual discernibility of zones reflecting an ordered arrangement may be substantially greater on the first-formed surface (which may form the wearer-facing surface of a topsheet). Consequently, the visual impact of the zones and of the resulting topographic/textural features may be more dramatic on the first-formed surface, than on the opposing last-formed surface. In conjunction therewith and with the method of manufacture, those portions of filaments occupying the attenuated regions will generally be closer in the z-direction, to the last-formed surface.

Although a melt spinning/spunbond process and deposition of filaments onto a forming belt is described above, it is also contemplated that other filaments and/or fiber deposition and basis weight distribution techniques and processes may be employed, including so-called co-forming processes described in, for example, U.S. Pat. Nos. 9,944,047; 8,017,534; 5,508,102; 4,100,324; and US 2003/0211802; PCT application publication number WO 2018/064595 A1; and US 2018/002848; US 2017/002486; US 2017/000695; US 2017/0342617; US 2016/0355950; and other techniques such as spunlace formation techniques in which a web formed of airlaid fibers (including natural and/or synthetic/polymeric fibers) have fiber location and distribution within the web material modified by controlled and ordered hydroenhancement/hydroentanglement, to form the ordered arrangement of channel portions, hinge portions, built-up and attenuated regions contemplated herein, and resulting ordered arrangements of features, which may be formed so as to be visually discernible. Other examples include the use of carded nonwovens having staple length fibers, combinations of carded, staple length fibers, spunbond filaments, and/or airlaid fibers.

Balancing Filament Surface Hydrophobicity and Hydrophilicity

As discussed above, filaments to be spun and accumulated to form the nonwoven web may be extruded from a polymer resin or blend of resins selected for various properties they impart to the filaments including tensile strength, tactile softness (affected by properties such as filament stiffness and surface coefficient of friction), hydrophilicity/hydrophobicity, etc., as well as cost. Additionally, the filaments and/or the formed nonwoven web may receive post-formation treatments applied, such as, for example, application of a surfactant to one or more surfaces.

Depending on the polymeric resin(s) used to spin them, surfaces of individual synthetic fibers or filaments may be slightly to highly hydrophilic, slightly to highly hydrophobic, or neutral, affecting the extent of the fibers'/filaments' tendency, or lack thereof, to attract aqueous fluid and draw it along their surfaces. Within a nonwoven web structure that includes numerous fiber/filament surfaces of varying geometry and/or spatial orientation, the extent of hydrophilicity or hydrophobicity of individual fiber surfaces in the aggregate, together with the extent of fiber consolidation that affects the porosity of the structure, will on a macroscopic level impart overall hydrophilicity, hydrophobicity, wicking, and absorption properties to the web structure. Including fibers or filaments of differing composition in the nonwoven will also have impact. Thus, depending upon the type(s) of constituent fibers or filaments used to form it, the macroscopic surface of a nonwoven web may be neutral, slightly to highly hydrophilic or slightly to highly hydrophobic, affecting the extent of its tendency to attract aqueous fluid, conduct ("wick") the fluid through interstices or pores within the fibrous structure, and retain (i.e., absorb) the fluid within the structure.

The extent to which a nonwoven as an overall structure tends to repel, or alternatively to attract, wick and/or retain aqueous fluid may be manipulated through selection of fiber/filament material composition, fiber spinning/processing, web structuring and fiber consolidation, and post formation treatment. Additives may be blended with polymer resins, which will modify the extent of hydrophilicity or hydrophobicity of the surfaces of the fibers or filaments spun from the resins. Following spinning of the fibers or filaments and/or formation of the nonwoven web material, hydrophobizing or hydrophilizing agents may be applied to the surfaces of the fibers or filaments and/or nonwoven.

In designing a nonwoven suitable for use as topsheet material for a wearable absorbent article such as a feminine hygiene pad, the manufacturer may face an inherent conflict. On one hand, the material must be sufficiently hydrophilic and have suitable porosity to accept a discharge of fluid such as urine or menses, and wick it in the z-direction so as to pass it through to an absorbent structure disposed beneath the topsheet. A topsheet that does not sufficiently and rapidly accept discharged fluid and move it in the z-direction down to the absorbent structure beneath increases the risk that the fluid will escape the article and soil underwear, outer garments, bedclothes, etc. On the other hand, if the material is hydrophilic and has a porosity level conducive to effective wicking, it may also be prone to incomplete drainage and/or rewetting, i.e., retaining and holding some portion of the discharged fluid, or reacquiring fluid from the absorbent structure. A topsheet that retains discharged fluid or is prone to rewetting is generally not preferred by users/wearers because it tends to feel unpleasantly wet and can promote overhydration of the skin.

It has been learned that a balance of hydrophobic and hydrophilic filament/nonwoven properties may be achieved within the structured topsheet material described herein, between suitable fluid acquisition rate and suitable low rewet tendency. Through prototyping and consumer testing it has been learned that consumer-users of feminine hygiene pads, for example, most prefer a pad configured with a topsheet that exhibits a maximum Rewet (expressed in grams of fluid) of no greater than 0.50 g, more preferably no greater than 0.45 g., and even more preferably no greater than 0.40 g, when the pad is tested using the Rewet measurement method set forth herein. Rewet as measured for purposes herein is a reflection of the absorbent structure/topsheet combination's tendency (or lack thereof) to pass absorbed fluid back into the topsheet under particular conditions, which reflect the topsheet's tendency to undesirably feel wet to the user under use conditions. Using the materials and topsheet structuring methods described herein, for example, a combination of polymeric spinning resin (e.g., polyolefin, e.g., polypropylene and/or polyethylene) whose inherent hydrophobicity may be supplemented by inclusion of a suitable hydrophobizing melt additive, rewet tendencies can be reduced, even down to substantially little or no rewet tendency.

However, a topsheet formed of a nonwoven of spun filaments with very low rewet tendency will necessarily be quite hydrophobic and/or of low porosity—and therefore, resistant to fluid penetration and movement in the z-direction therethrough. Upon contacting the wearer-facing surface of such a topsheet, fluid will tend to roll over the surface along an x-y direction without penetrating it, increasing the risk that the fluid will remain in contact with the user's skin and create an insecure wet feeling, and the risk that it will escape the pad and soil surrounding underwear, outer garments, etc. Accordingly, while a low rewet tendency for a topsheet may be desirable in theory, it must be balanced with other features that enable the topsheet to receive and move the fluid in a z-direction.

An ordered arrangement of zones including attenuated regions and built-up regions as described herein, which may be combined with application of a surfactant as described herein, provides a way of striking this balance. The attenuated regions, being relatively sparsely populated by filaments, provide pathways for fluid to move in a z-direction through the topsheet. Additionally, application of a surfactant to the absorbent-facing side of the topsheet web (where the absorbent-facing side is the side of the web that faced away from the forming belt 260 during formation of the web) results in a predominant number of filaments in the attenuated regions having surfactant on their surfaces and thereby being rendered hydrophilic, while filaments on the wearer-facing side of the built-up regions 166 remain relatively hydrophobic. On a macroscopic level, the attenuated regions exhibit behavior akin to small drains in the topsheet through which fluid will be drawn in a z-direction down through the topsheet. The surfactant may be selected and applied at a chosen coverage quantity to adjust the rapidity with which fluid will move through the topsheet.

However, just as excessive hydrophobicity can frustrate fluid acceptance and movement within the topsheet, excessive hydrophilicity imparted by, e.g., excessive application of surfactant, can impart unacceptable rewet tendency. Through prototyping and consumer testing it has been learned that consumer-users of feminine hygiene pads most prefer a pad configured with an absorbent structure and a topsheet that exhibits an Acquisition Time (expressed in seconds) of no greater than 25 s, when the pad is tested using the Acquisition Time measurement method set forth herein. Acquisition Time as measured for purposes herein is a reflection of the absorbent structure/topsheet combination's tendency (or lack thereof) to receive and transfer fluid in a z-direction to the absorbent structure under particular conditions. Rapid acquisition is preferable but cannot be reduced freely without adversely increasing rewet tendency of the topsheet. Using the materials and topsheet structuring methods described herein, for example, a combination of fibers having inherent and/or supplemented hydrophobicity, Acquisition Time can be reduced. It has been learned that consumer users most prefer a combination of absorbent structure and topsheet in which a balance has been struck between an Acquisition Time no greater than 25 s, more preferably no greater than 20 s, and even more preferably no greater that 15 s and Rewet no greater than 0.50 g.

Data collected through experimentation and consumer testing suggests that lower limits on these ranges may exist, within the context of the materials and structures described herein. Through experimentation the lowest Rewet level achieved with an Acquisition Time no greater than 15 s was about 0.24 g. The lowest Acquisition Time with a Rewet no greater than 0.50 g was about 4 s. Without intending to be bound by theory, however, it is believed that these combined values may be reduced further with suitable experimentation with materials and structures as described herein. The operative combination of maximum Rewet and maximum Acquisition Time is believed to be an important discovery of consumer preference for and consumer satisfaction with a pad with a functionally structured, visually appealing topsheet as described herein.

Experimental Samples

Prototype/sample feminine hygiene pads R, L, P were manufactured having the following components:

Each pad had a topsheet cut from a nonwoven web material formed of side-by-side bicomponent spunbond filaments with a 70:30 component weight ratio of two differing polypropylene resin compositions. Approximately 1 percent by weight titanium dioxide was blended into the resin compositions. Erucamide was added to the resin compositions for the differing samples, in quantities shown in Table 2 below. The differing polypropylene components exhibited differing contraction rates on cooling, resulted in helically crimped or curled spun filaments. Spinning and attenuating equipment was adjusted to impart the spun filaments with an average diameter of approximately 18 μm. The spun filaments were deposited onto a moving forming belt formed with airflow blocking structures of shapes and sizes reflected by the image of the mask depicted in FIG. 28, to result in a nonwoven having the ordered arrangement of zones depicted in FIG. 26B. Filament spinning and deposition rates were controlled to impart the nonwoven with an average basis weight of approximately 27-32 gsm. Following filament spinning and deposition on the forming belt, the batt was compacted in a nip as schematically depicted as element 570a in FIG. 11, wherein the compaction roller was heated to approximately 140 C. Following compaction and removal from the forming belt the batt was calender bonded in a nip between patterned and anvil bonding rollers heated to approximately 140-145 C. The patterned bonding roller was configured to impart a regular pattern of regularly-spaced circular bonds each having a diameter of approximately 0.8 mm, and suitable numerical density per unit surface area to result in a total bonded area for the finished web product of approximately 10 percent of the total surface area on one side.

The topsheet was overlaid directly onto a secondary topsheet/acquisition/distribution layer having a basis weight of 55 gsm and formed of carded spunlace staple fibers consisting of a blend of 40 percent by weight viscose fibers of 1.7 decitex, 40 percent by weight polyethylene/polypropylene bicomponent fibers of 1.7 decitex, and 20 percent by weight PET fibers of 4.4 decitex.

The secondary topsheet directly overlaid an additional absorbent structure layer formed of a blend of cellulose fibers, bicomponent polymer staple fibers and particles of absorbent gelling material, airlaid to a basis weight of 160 gsm, which has been used in product in the market.

The additional absorbent structure layer directly overlaid a backsheet formed of liquid impervious polyethylene film, which was bonded about its perimeter via adhesive to the topsheet, whereby the topsheet and the backsheet formed an envelope containing the absorbent structure including the secondary topsheet and the additional absorbent structure layer.

For purposes of studying the effects and interactions between an example of a melt additive and an example of a surfactant and consumer preferences, the polypropylene resins used to spin the topsheet filaments, for varying sample, had varying levels of erucamide added and blended into the melted resin as melt additive prior to spinning. The finished topsheet materials for the varying samples had the indicated varying levels of surfactant applied to the core-facing surface, via inkjet printing equipment. The surfactant applied was STANTEX S6887, obtained via a U.S. sales office representing Pulcra Chemicals/Fashion Chemicals GmbH & Co., Geretsried, Germany. The amount of melt additive included and the amount of surfactant applied for various samples is set forth in Table 2 below.

For each sample, the Acquisition Time and the Rewet were measured using the Acquisition Time and Rewet Measurement methods set forth below. From the data, it can be seen that Acquisition Time and Rewet in combination may be manipulated by manipulation of the amounts of melt additive added and surfactant applied. As noted, it has been concluded from consumer testing that a pad having a combination of Rewet of no greater than 0.50 g, more preferably no greater than 0.45 g, and even more preferably no greater than 0.40 g, and an Acquisition Time of no greater than 25 seconds, more preferably no greater than 20 seconds, and even more preferably no greater than 15 seconds, is acceptable or preferred by consumers, over a pad that falls outside these parameters. Generally, the data reflected that, while a relatively shorter Acquisition Time was preferred, a trade-off was a relatively greater Rewet, which was not preferred. Manipulation of features described herein, including a topsheet formed as described herein, enabled a suitable balance of acceptable levels of these fluid handling characteristics. Prototype/sample feminine hygiene pads G, E, and N, were manufactured having the following components:

Each of the sample pads G, E, and N, had a topsheet cut from a nonwoven web material formed of side-by-side bicomponent spunbond filaments with a 70:30 component weight ratio of two differing polypropylene resin compositions. Approximately 1 percent by weight titanium dioxide was blended into the resin compositions. Erucamide was added to the resin compositions for the differing samples, in quantities shown in Table 2 below. The differing polypropylene components exhibited differing contraction rates on cooling, resulted in helically crimped or curled spun filaments. Spinning and attenuating equipment was adjusted to impart the spun filaments with an average diameter of approximately 18 μm. The spun filaments were deposited onto a moving forming belt formed with airflow blocking structures of shapes and sizes reflected by the image of the mask depicted in FIG. 30, to result in a nonwoven having the ordered arrangement of zones depicted in FIG. 29. Filament spinning and deposition rates were controlled to impart the nonwoven with an average basis weight of approximately 25-27 gsm. Following filament spinning and deposition on the forming belt, the batt was compacted in a nip as schematically depicted as element 570a in FIG. 11, wherein the compaction roller was heated to approximately 140 C. Following compaction and removal from the forming belt the batt was calender bonded in a nip between patterned and anvil bonding rollers heated to approximately 140-145 C. The patterned bonding roller was configured to impart a regular pattern of regularly-spaced circular bonds each having a diameter of approximately 0.8 mm, and suitable numerical density per unit surface area to result in a total bonded area for the finished web product of approximately 10 percent of the total surface area on one side.

The finished topsheet materials for the varying samples had the indicated varying levels of surfactant applied to the core-facing surface, via inkjet printing equipment. The surfactant applied was STANTEX S6887, obtained via a U.S. sales office representing Pulcra Chemicals/Fashion Chemicals GmbH & Co., Geretsried, Germany. The amount of melt additive included and the amount of surfactant applied for various samples is set forth in Table 2 below.

Sample G comprised a fluid management layer having carded, spunlace fibers, the fluid management layer having a basis weight of 55 gsm with 20 percent by weight viscose cellulose fibers having a 1.7 dtex; 30 percent by weight hollow spiral polyethylene terephthalate fibers having a 10 dtex; and 50 percent by weight bi-component fibers having a first component polyethylene terephthalate and polyethylene in a core-sheath configuration where the polyethylene is the sheath. The fluid management layer of Sample G was constructed in accordance with the present disclosure.

Sample E comprised a fluid management layer having carded, spunlace fibers, the fluid management layer having a basis weight of 65 gsm with 20 percent by weight viscose cellulose fibers having a 1.3 dtex; 30 percent by weight hollow spiral polyethylene terephthalate fibers having a 10 dtex; and 50 percent by weight bi-component fibers having a first component polyethylene terephthalate and polyethylene in a core-sheath configuration where the polyethylene is the sheath having a 2.2 dtex. The fluid management layer of Sample E was constructed in accordance with the present disclosure.

Sample N comprised a fluid management layer having carded, spunlace fibers, the fluid management layer having a basis weight of 50 gsm with 40 percent by weight viscose fibers of 1.7 dtex, 40 percent by weight polyethylene/polypropylene bicomponent fibers of 1.7 dtex, and 20 percent by weight PET fibers of 4.4 dtex. The fluid management layer of Sample N was formed via conventional spunlace processing and is currently available on the market.

Each of Samples G, E, and N, also comprised an absorbent core formed of a blend of cellulose fibers, bicomponent polymer staple fibers and particles of absorbent gelling material, airlaid to a basis weight of 182 gsm, an absorbent structure composition which has been used in product in the market.

Each of Samples G, E, and N, also comprised a backsheet formed of liquid impervious polyethylene film, which was bonded about its perimeter via adhesive to the topsheet, whereby the topsheet and the backsheet formed an envelope containing the absorbent structure including the secondary topsheet and the absorbent core. Additionally, adhesive was utilized to join the topsheet to the secondary topsheet positioned between the topsheet and the absorbent core.

For each of Samples G, E, and N, the Acquisition Time and the Rewet were measured using the Acquisition Time and Rewet Measurement methods as described herein.

TABLE 2

| Sample Code | Melt additive % by weight | Surfactant level (gsm) | First Dose Acquisition Time (s) | Second Dose Acquisition Time (s) | Third Dose Acquisition Time (s) | Rewet (g) |
|---|---|---|---|---|---|---|
| R | 0.0% | 1.0 | 4 | 5.5 | 7 | 0.64 |
| L | 1.5% | 0.85 | 4.5 | 6.5 | 7.5 | 0.42 |
| P | 1.5% | 0.13 | 16.5 | 11.5 | 13 | 0.29 |
| G | 1.5% | 0.16 | 5 | 5 | 5 | 0.19 |
| E | 1.5% | 0.16 | 6 | 5 | 5 | 0.18 |
| N | 1.5% | 0.16 | 8 | 10 | 11 | 0.16 |

From the data, it can be seen that Acquisition Time and Rewet in combination may be impacted by manipulation of the amounts of melt additive added and surfactant applied. Consumer preference, as noted herein, is quick acquisition speed and low rewet. Unfortunately, these two metrics are diametrically opposed. Generally, faster acquisition speeds go hand in hand with higher rewets and vice versa. However, creation of the topsheet described herein, enables a suitable balance in achieving acceptable levels of these fluid handling characteristics. For example, Samples L, P, G, E, and N, provided good acquisition speeds along with low rewet.

The Acquisition Time and the Rewet data for Samples G, E, and N, demonstrated even better performance characteristics over those of Samples L and P. As shown, Samples G, E, and N. constructed in accordance with the present disclosure exhibited an acquisition speed for each of the first, second, and third gush which was lower than 15 seconds coupled with rewet values of less than 0.40 grams. Additionally, as Samples G and E comprised the additional benefit of a fluid management layer of the present disclosure, Samples G and E exhibited acquisition speeds for each of the first, second, and third gush which were lower than 10 seconds coupled with rewets of less than 0.30 grams.

Absorbent articles of the present disclosure may exhibit acquisition speeds at the first, second, and/or third, gush of less than 15 seconds, more preferably 10 seconds or less, or most preferably 6 seconds or less, specifically reciting all values within these ranges and any ranges created thereby. For example, absorbent articles constructed in accordance with the present invention may exhibit acquisition speeds at the first, second, and/or third gush, of from between about 3 seconds to about 15 seconds, more preferably from between about 3 seconds to about 10 seconds, or most preferably from about 3 seconds to about 7 seconds, specifically reciting all values within these ranges and any ranges created thereby.

Additionally, where the absorbent articles include the fluid management layers of the present disclosure along with the topsheets of the present disclosure even better acquisition speeds can be achieved without a corresponding increase in rewet. For example, these absorbent articles, e.g. Samples G and E, exhibit an acquisition speed at the first, second, and/or third acquisition speed of 10 seconds or less, more preferably 8 seconds or less, or most preferably 7 seconds or less, specifically reciting all values within these ranges and any ranges created thereby. As another example, the acquisition speeds for the first, second, and/or third gush, are between 3 second to about 10 seconds, more preferably from about 3 seconds to about 8 seconds, or most preferably from about 3 seconds to about 7 seconds, specifically reciting all values within these ranges and any ranges created thereby.

For example, Sample G and E, may exhibit an acquisition speed during the first gush of less than 8 seconds, more preferably less than 7 seconds, or most preferably less than 6 seconds, specifically reciting all values within these ranges and any ranges created thereby. Sample G and E may exhibit an acquisition speed at first gush of from between 3 second to about 8 seconds, more preferably 3 seconds to about 7 seconds, or most preferably from about 3 seconds to about 6 seconds, specifically including all values within these ranges and any ranges created thereby.

For the second gush, Samples G and E may exhibit an acquisition speed of 8 seconds or less, more preferably 7 seconds or less, or most preferably 6 seconds or less, specifically reciting all values within these ranges and any ranges created thereby. For example, acquisition speed of Samples G and E for the second gush may be from between 3 seconds to about 8 seconds, more preferably from about 3 seconds to about 7 seconds, or most preferably 3 seconds to about 6 seconds, specifically including all values within these ranges and any ranges created thereby.

For the third gush, Samples G and E may exhibit an acquisition speed of 9 seconds or less, more preferably 8 seconds or less, or most preferably 7 seconds or less, specifically reciting all values within these ranges and any ranges created thereby. For example, Samples G and E may exhibit acquisition speeds during the third gush of from between 3 seconds to about 9 seconds, more preferably from about 3 seconds to about 8 seconds, or most preferably from about 3 seconds to about 7 seconds, specifically reciting all values within these ranges and any ranges created thereby.

These absorbent articles, e.g. Samples G and E, may also exhibit a difference between the first gush acquisition and the second gush acquisition of less than 2 seconds, or more preferably 1 second or less. Additionally, these absorbent article may exhibit a difference between the first gush acquisition and the third gush acquisition speed of less than 3 seconds or more preferably less than 2 seconds, or most preferably less than 1 second.

Similarly, absorbent articles of the present disclosure, e.g., Samples G, E, and N, may exhibit rewet of less than 0.4 grams, more preferably less than 0.3 grams, or most preferably less than 0.2 grams, specifically reciting all values within these ranges and any ranges created thereby. For example, absorbent articles of the present disclosure may exhibit rewet values of from between 0.1 to about 0.4 grams, more preferably from about 0.1 grams to about 0.3 grams, or most preferably 0.1 to about 0.2 grams, specifically reciting all values within these ranges and any ranges created thereby.

Additionally, the absorbent articles which include the fluid management layers of the present disclosure coupled with the topsheets of the present disclosure can exhibit rewet values which are less than 0.25 grams or more preferably less than 0.20 grams, specifically reciting all values within these ranges and any ranges created thereby. For example, these absorbent articles can exhibit rewet values from between 0.10 to about 0.25 grams or more preferably from about 0.10 grams to about 0.20 grams, specifically reciting all values within these ranges and any ranges created thereby.

The acquisition speeds and rewet values exhibited, particularly by Samples G, E, and N, are believed to be, in part, due to the use of melt additive and surfactant on the topsheet. Melt additive can be provided to the topsheets of the present disclosure at about 0.5 percent by weight to about 2 percent by weight or more preferably from about 0.5 percent by weight to about 1.5 percent by weight, specifically reciting all values within these ranges in every 0.1 increment and including all ranges created thereby. The surfactant level in gsm was discussed previously.

Test and Measurement Methods

Localized Basis Weight

Localized basis weight of a region of a formed nonwoven web material may be determined by several available techniques, but a simple representative technique when the region is suitably large involves cutting a sample piece of the web representing the selected region from the overall area of the material. The sample piece is then weighed and divided by its area to yield the localized basis weight of the nonwoven fabric in, units of grams per square meter (gsm). Results are reported as a mean of 2 samples per selected region.

Micro-CT Intensive Property Measurement Method

The micro-CT intensive property measurement method measures the basis weight, thickness and volumetric density values within visually discernable regions of a sample of nonwoven web material. It is based on analysis of a 3D x-ray sample image obtained on a micro-CT instrument (a suitable instrument is the Scanco μCT 50 available from Scanco Medical AG, Switzerland, or equivalent). The micro-CT instrument is a cone beam microtomograph with a shielded cabinet. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. A 3D image of the sample is generated by collecting several individual projection images of the sample as it is rotated, which are then reconstructed into a single 3D image. The instrument is interfaced with a computer running software to control the image acquisition and save the raw data. The 3D image is then analyzed using image analysis software (a suitable image analysis software is MATLAB available from The Mathworks, Inc., Natick, MA, or equivalent) to measure the basis weight, thickness and volumetric density intensive properties of regions within the sample.

Sample Preparation

To obtain a sample for measurement, lay a single layer of the formed nonwoven web material of interest out flat on a work surface, and die cut therefrom a circular piece with a diameter of 30 mm.

If the material is a layer of an absorbent article, for example a topsheet, backsheet nonwoven, acquisition layer, distribution layer, or other component layer; tape the absorbent article to a rigid flat surface in a planar configuration. Carefully separate the layer from the absorbent article. A scalpel and/or cryogenic spray (to substantially deactivate adhesives) (such as Cyto-Freeze, Control Company, Houston TX) may be used as necessary to remove a substrate layer from additional underlying layers, if necessary, to avoid any longitudinal and lateral extension of the material.

Once the substrate layer has been removed from the article proceed with die cutting the sample as described above.

A sample may be cut from any location containing the zone to be analyzed. Within a zone, regions to be analyzed are ones associated with an ordered arrangement as defined herein. The zone includes a least two regions. A zone and regions thereof may be visually discernible or otherwise identifiable due to changes in fiber and/or filament area density, basis weight, opacity, caliper/thickness or z-direction elevation. Regions within different samples taken from the same substrate material may be analyzed and compared to each other. Care should be taken to avoid folds, wrinkles or tears when selecting a location on the formed nonwoven web material of interest for sampling.

Image Acquisition

Set up and calibrate the micro-CT instrument according to the manufacturer's specifications. Place the sample into the appropriate holder, between two rings of low density material, which have an inner diameter of 25 mm. This will allow the central portion of the sample to lay horizontal and be scanned without having any other materials directly adjacent to its upper and lower surfaces. Measurements should be taken in this region. The 3D image field of view is approximately 35 mm on each side in the x-y plane with a resolution of approximately 5000 by 5000 pixels, and with a sufficient number of 7 micron thick slices collected to fully include the z-direction of the sample. The reconstructed 3D image resolution contains isotropic voxels of 7 microns. Images are acquired with the source at 45 kVp and 133 μA with no additional low energy filter. These current and voltage settings may be optimized to produce the maximum contrast in the projection data with sufficient x-ray penetration through the sample, but once optimized held constant for all substantially similar samples. A total of 1500 projections images are obtained with an integration time of 1000 ms and 3 averages. The projection images are reconstructed into the 3D image and saved in 16-bit RAW format to preserve the full detector output signal for analysis.

Image Processing

Load the 3D image into the image analysis software. Threshold the 3D image at a value which separates, and removes, the background signal due to air, but maintains the signal from the sample fibers within the substrate.

Three 2D intensive property images are generated from the threshold 3D image. The first is the Basis Weight Image. To generate this image, the value for each voxel in an x-y plane slice is summed with all of its corresponding voxel values in the other z-direction slices containing signal from the sample. This creates a 2D image where each pixel now has a value equal to the cumulative signal through the entire sample.

In order to convert the raw data values in the Basis Weight Image into real values a basis weight calibration curve is generated. Obtain a substrate that is of substantially similar composition as the sample being analyzed and has a uniform basis weight. Follow the procedures described above to obtain at least ten replicate samples of the calibration curve substrate. Accurately measure the basis weight, by taking the mass to the nearest 0.0001 g and dividing by the sample area and converting to grams per square meter (gsm), of each of the single layer calibration samples and calculate the average to the nearest 0.01 gsm. Following the procedures described above, acquire a micro-CT image of a single layer of the calibration sample substrate. Following the procedure described above, process the micro-CT image, and generate a Basis Weight Image containing raw data values. The real basis weight value for this sample is the average basis weight value measured on the calibration samples. Next, stack two layers of the calibration substrate samples on top of each other, and acquire a micro-CT image of the two layers of calibration substrate. Generate a basis weight raw data image of both layers together, whose real basis weight value is equal to twice the average basis weight value measured on the calibration samples. Repeat this procedure of stacking single layers of the calibration substrate, acquiring a micro-CT image of all of the layers, generating a raw data basis weight image of all of the layers, the real basis weight value of which is equal to the number of layers times the average basis weight value measured on the calibration samples. A total of at least four different basis weight calibration images are obtained. The basis weight values of the calibration samples must include values above and below the basis weight values of the original sample being analyzed to ensure an accurate calibration. The calibration curve is generated by performing a linear regression on the raw data versus the real basis weight values for the four calibration samples. This linear regression must have an R2 value of at least 0.95, if not repeat the entire calibration procedure. This calibration curve is now used to convert the raw data values into real basis weights.

The second intensive property 2D image is the Thickness Image. To generate this image the upper and lower surfaces of the sample are identified, and the distance between these surfaces is calculated giving the sample thickness. The upper surface of the sample is identified by starting at the uppermost z-direction slice and evaluating each slice going through the sample to locate the z-direction voxel for all pixel positions in the x-y plane where sample signal was first detected. The same procedure is followed for identifying the lower surface of the sample, except the z-direction voxels located are all the positions in the x-y plane where sample signal was last detected. Once the upper and lower surfaces have been identified they are smoothed with a 15×15 median filter to remove signal from stray fibers. The 2D Thickness Image is then generated by counting the number of voxels that exist between the upper and lower surfaces for each of the pixel positions in the x-y plane. This raw thickness value is then converted to actual distance, in microns, by multiplying the voxel count by the 7 μm slice thickness resolution.

The third intensive property 2D image is the Volumetric Density Image. To generate this image divide each x-y plane pixel value in the Basis Weight Image, in units of gsm, by the corresponding pixel in the Thickness Image, in units of microns. The units of the Volumetric Density Image are grams per cubic centimeter (g/cc).

Micro-CT Basis Weight, Thickness and Volumetric Density Intensive Properties

Begin by identifying the region to be analyzed. A region to be analyzed is one associated with a zone. The zone includes a least two regions. A zone and regions thereof, may be visually discernible or otherwise identifiable due to changes in fiber and/or filament area density, basis weight, opacity, caliper/thickness or z-direction elevation. Next, identify the boundary of the region to be analyzed. The boundary of a region is identified by visual discernment of differences in intensive properties when compared to other regions within the sample. For example, a region boundary may be identified based by visually discerning a thickness/caliper difference when compared to another region in the sample. Any of the intensive properties may be used to discern region boundaries on either the physical sample itself of any of the micro-CT intensive property images. Once the boundary of the region has been identified, draw an oval or circular "region of interest" (ROI) within the interior of the region. The ROI should have an area of at least 0.1 mm$^2$ and be selected to measure an area with intensive property values representative of the identified region. From each of the three intensive property images calculate the average basis weight, thickness and volumetric density within the ROI. Record these values as the region's basis weight to the nearest 0.01 gsm, thickness to the nearest 0.1 micron and volumetric density to the nearest 0.0001 g/cc.

Acquisition Time and Rewet Measurement

Artificial Menstrual Fluid (AMF) Preparation

The Artificial Menstrual Fluid (AMF) is composed of a mixture of defibrinated sheep blood, a phosphate buffered saline solution and a mucous component. The AMF is prepared such that it has a viscosity between 7.15 to 8.65 centistokes at 23° C.

Viscosity on the AMF is performed using a low viscosity rotary viscometer (a suitable instrument is the Cannon LV-2020 Rotary Viscometer with UL adapter, Cannon Instrument Co., State College, PA, or equivalent). The appropriate size spindle for the viscosity range is selected, and instrument is operated and calibrated as per the manufacturer. Measurements are taken at 23° C.±1 C.° and at 60 rpm. Results are reported to the nearest 0.01 centistokes.

Reagents needed for the AMF preparation include: defibrinated sheep blood with a packed cell volume of 38% or greater (collected under sterile conditions, available from Cleveland Scientific, Inc., Bath, OH, or equivalent), gastric mucin with a viscosity target of 3-4 centistokes when prepared as a 2% aqueous solution (crude form, available from Sterilized American Laboratories, Inc., Omaha, NE, or equivalent), 10% v/v lactic acid aqueous solution, 10% w/v potassium hydroxide aqueous solution, sodium phosphate dibasic anhydrous (reagent grade), sodium chloride (reagent grade), sodium phosphate monobasic monohydrate (reagent grade) and distilled water, each available from VWR International or an equivalent source.

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add distilled water to volume. Mix thoroughly. To prepare the phosphate buffered saline solution, add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. To determine the amount of gastric mucin needed to achieve AMF within the target viscosity range (7.15-8.65 centistokes at 23° C.) prepare 3 batches of AMF with varying amounts of gastric mucin in the mucous component, and then interpolate the exact amount needed from a concentration versus viscosity curve with a least squares linear fit through the three points. A successful range of gastric mucin is usually between 38 to 50 grams.

To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5 C°. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range. After the 2.5 hours has elapsed, remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1 C°.

Allow the temperature of the sheep blood and mucous component to come to 23° C.±1 C°. Using a 500 mL graduated cylinder, measure the volume of the entire batch of the previously prepared mucous component and add it to a 1200 mL beaker. Add an equal volume of sheep blood to the beaker and mix thoroughly. Using the viscosity method previously described, ensure the viscosity of the AMF is between 7.15-8.65 centistokes. If not the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1 C°. Any unused portion is discarded after testing is complete.

Measurement

Acquisition Time is measured for an absorbent article loaded with Artificial Menstrual Fluid (AMF), prepared as described herein.

A known volume of AMF is introduced three times, each successive dose starting two minutes after the previous dose has absorbed. The time required for each dose to be absorbed by the article is recorded. Subsequent to the acquisition test, a rewet method is performed to determine the mass of fluid expressed from the article under pressure. Sample feminine hygiene pads are conditioned at 23 C±2 C and 50%±2% relative humidity for 2 hours prior to testing, and all testing is performed under these conditions.

The confining weight used for the rewet test has a flat level base with a contact surface that is 64±1 mm wide by 83±1 mm long and a mass of 2268±2 grams (5 pounds). This weight provides a confining pressure of 4.1 kPa (0.60 psi) on the test article. The rewet substrate is two sheets of filter paper with dimensions 4 inch by 4 inch. A suitable filter paper is Ahlstrom Grade 989 (available from Ahlstrom-Munksjo North America LLC, Alpharetta, GA) or equivalent.

Perform the Acquisition Time measurement as follows. Remove the sample from its wrapper. If folded, gently unfold and smooth out any wrinkles. Place the sample flat on a horizontal planar work surface, with the topsheet facing upward. Position the tip of a mechanical pipette about 1 cm above the center (intersection of longitudinal and lateral axes) of the article's absorbent structure, and accurately pipette 1.00 ml±0.05 ml of AMF onto the surface. The fluid is dispensed without splashing, within a period of 2 seconds. As soon as the fluid makes contact with the test sample, start a timer accurate to 0.01 seconds. After the fluid has been acquired (no pool of fluid left on the surface), stop the timer and record the acquisition time to the nearest 0.01 second. Wait 2 minutes. In a similar manner, respective second and third doses of AMF are applied to the test sample, and the acquisition times are recorded to the nearest 0.01 second. Proceed with the Rewet test 2 minutes after the third dose has been acquired.

Perform the Rewet part of the test as follows. Measure the dry mass of two filter papers together to the nearest 0.0001 grams, and record as MassDry. Gently place the dry filter papers over the center (intersection of longitudinal and lateral axes) of the sample's absorbent structure, with the filter papers themselves also centered about such point. Gently place the base of the confining weight over such center, positioning the length (long side) of the weight parallel to the longitudinal direction of the sample Immediately upon placement of the weight to rest over the sample and filter papers, start a timer accurate to 0.01 seconds. After 30 seconds, carefully remove the weight. Measure the mass of the filter papers to the nearest 0.0001 grams and record as MassWet. Calculate Rewet as the difference between MassWet and MassDry for the filter papers and record as Rewet to the nearest 0.0001 grams.

This entire procedure is repeated on five substantially similar replicate articles. The reported value is the average of the five individual recorded measurements for each Acquisition Time (first, second and third) to the nearest 0.01 second and Rewet to the nearest 0.0001 gram.

Material Compositional Analysis

The quantitative chemical composition of a test specimen comprising a mixture of fiber types is determined using ISO 1833-1. All measurements are performed in a laboratory maintained at 23° C.±2 C.° and 50%±2% relative humidity.

Analysis is performed on test samples taken from rolls or sheets of the raw material, or test samples obtained from a material layer removed from an absorbent article. When excising the material layer from an absorbent article, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained and tested as per ISO 1833-1 to quantitatively determine its chemical composition.

Caliper

The caliper, or thickness, of a test specimen is measured as the distance between a reference platform on which the specimen rests and a pressure foot that exerts a specified amount of pressure onto the specimen over a specified amount of time. All measurements are performed in a laboratory maintained at 23° C.±2 C.° and 50%±2% relative humidity and test specimens are conditioned in this environment for at least 2 hours prior to testing.

Caliper is measured with a manually-operated micrometer equipped with a pressure foot capable of exerting a steady pressure of 0.50 kPa±0.01 kPa onto the test specimen. The manually-operated micrometer is a dead-weight type instrument with readings accurate to 0.01 mm A suitable instrument is Mitutoyo Series 543 ID-C Digimatic, available from VWR International, or equivalent. The pressure foot is a flat ground circular movable face with a diameter that is smaller than the test specimen and capable of exerting the required pressure. A suitable pressure foot has a diameter of 25.4 mm, however a smaller or larger foot can be used depending on the size of the specimen being measured. The test specimen is supported by a horizontal flat reference platform that is larger than and parallel to the surface of the pressure foot. The system is calibrated and operated per the manufacturer's instructions.

Obtain a test specimen by removing it from an absorbent article, if necessary. When excising the test specimen from an absorbent article, use care to not impart any contamination or distortion to the test specimen layer during the process. The test specimen is obtained from an area free of folds or wrinkles, and it must be larger than the pressure foot.

To measure caliper, first zero the micrometer against the horizontal flat reference platform. Place the test specimen on the platform with the test location centered below the pressure foot. Gently lower the pressure foot with a descent rate of 3.0 mm±1.0 mm per second until the full pressure is exerted onto the test specimen. Wait 5 seconds and then record the caliper of the test specimen to the nearest 0.001 mm. In like fashion, repeat for a total of ten replicate test specimens. Calculate the arithmetic mean for all caliper measurements and report as Caliper to the nearest 0.001 mm Caliper Factor The caliper factor, as mentioned previously is the caliper per 10 gsm of basis weight of the sample. So, the equation is caliper/(basis weight/10).

Fiber Decitex (Dtex)

Textile webs (e.g. woven, nonwoven, airlaid) are comprised of individual fibers of material. Fibers are measured in terms of linear mass density reported in units of decitex. The decitex value is the mass in grams of a fiber present in 10,000 meters of that fiber. The decitex value of the fibers within a web of material is often reported by manufacturers as part of a specification. If the decitex value of the fiber is not known, it can be calculated by measuring the cross-sectional area of the fiber via a suitable microscopy technique such as scanning electron microscopy (SEM), determining the composition of the fiber with suitable techniques such as FT-IR (Fourier Transform Infrared) spectroscopy and/or DSC (Dynamic Scanning calorimetry), and then using a literature value for density of the composition to calculate the mass in grams of the fiber present in 10,000 meters of the fiber. All testing is performed in a room maintained at a temperature of 23° C.±2.0° C. and a relative humidity of 50%±2% and samples are conditioned under the same environmental conditions for at least 2 hours prior to testing.

If necessary, a representative sample of web material of interest can be excised from an absorbent article. In this case, the web material is removed so as not to stretch, distort, or contaminate the sample.

SEM images are obtained and analyzed as follows to determine the cross-sectional area of a fiber. To analyze the cross section of a sample of web material, a test specimen is prepared as follows. Cut a specimen from the web that is about 1.5 cm (height) by 2.5 cm (length) and free from folds or wrinkles. Submerge the specimen in liquid nitrogen and fracture an edge along the specimen's length with a razor blade (VWR Single Edge Industrial Razor blade No. 9, surgical carbon steel). Sputter coat the specimen with gold and then adhere it to an SEM mount using double-sided conductive tape (Cu, 3M available from electron microscopy sciences). The specimen is oriented such that the cross section is as perpendicular as possible to the detector to minimize any oblique distortion in the measured cross sections. An SEM image is obtained at a resolution sufficient to clearly elucidate the cross sections of the fibers present in the specimen. Fiber cross sections may vary in shape, and some fibers may consist of a plurality of individual filaments. Regardless, the area of each of the fiber cross sections is determined (for example, using diameters for round fibers, major and minor axes for elliptical fibers, and image analysis for more complicated shapes). If fiber cross sections indicate inhomogeneous cross-sectional composition, the area of each recognizable component is recorded and dtex contributions are calculated for each component and subsequently summed. For example, if the fiber is bi-component, the cross-sectional area is measured separately for the core and sheath, and dtex contribution from core and sheath are each calculated and summed. If the fiber is hollow, the cross-sectional area excludes the inner portion of the fiber comprised of air, which does not appreciably contribute to fiber dtex. Altogether, at least 100 such measurements of cross-sectional area are made for each fiber type present in the specimen, and the arithmetic mean of the cross-sectional area $a_k$ for each are recorded in units of micrometers squared ($\mu m^2$) to the nearest 0.1 $\mu m^2$.

Fiber composition is determined using common characterization techniques such as FTIR spectroscopy. For more complicated fiber compositions (such as polypropylene core/polyethylene sheath bi-component fibers), a combination of common techniques (e.g. FTIR spectroscopy and DSC) may be required to fully characterize the fiber composition. Repeat this process for each fiber type present in the web material.

The decitex $d_k$ value for each fiber type in the web material is calculated as follows:

$$d_k = 10\ 000\ m \times a_k \times \rho_k \times 10^{-6}$$

where $d_k$ is in units of grams (per calculated 10,000 meter length), $a_k$ is in units of $\mu m^2$, and $\rho_k$ is in units of grams per cubic centimeter (g/cm$^3$). Decitex is reported to the nearest 0.1 g (per calculated 10,000 meter length) along with the fiber type (e.g. PP, PET, cellulose, PP/PET bico).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed:

1. A disposable absorbent article comprising:
a nonwoven topsheet comprising a lateral axis, a longitudinal axis, and an in-use wearer-facing portion having an elongate outer perimeter, wherein the topsheet is formed of a section of formed nonwoven web material comprising an accumulation of filaments and having an absorbent-facing side and a wearer-facing side, the wearer-facing side comprising an ordered arrangement of zones, wherein each zone comprising one or more attenuated regions adjacent to one or more built-up regions, and wherein the attenuated regions have a first average basis weight and the one or more built-up regions have a second average basis weight, wherein the first average basis weight is less than the second average basis weight, wherein the difference in basis weight corresponds to disposition of the filaments according to the ordered arrangement;
a backsheet;
an absorbent core disposed between the topsheet and the backsheet;
an integrated nonwoven fluid management layer disposed between the topsheet and the absorbent core, wherein the fluid management layer comprises a basis weight in a range of from 40 gsm to 75 gsm as determined by the Localized Basis Weight method, 10 percent to about 60 percent by weight of absorbent fibers, from between about 15 percent to about 70 percent of resilient fibers, and from between about 25 percent to about 70 percent stiffening fibers as determined by the Material Composition Analysis method;
wherein the absorbent article exhibits a third dose acquisition time of less than 10 seconds, and a Rewet of no greater than 0.40 g, when measured in accordance with the Acquisition Time and Rewet Measurement method disclosed herein.

2. The disposable absorbent article of claim 1, wherein the filaments have a diameter of 10 microns to about 30 microns.

3. The disposable absorbent article of claim 1, wherein the topsheet has an overall basis weight of about 10 gsm to about 50 gsm.

4. The disposable absorbent article of claim 1, wherein the topsheet comprises a hydrophilic treatment, and wherein the hydrophilic treatment is applied at about 0.1 to about 0.8 gsm.

5. The disposable absorbent article of claim 1, wherein the nonwoven topsheet comprises a melt additive at a weight fraction of 0.5 percent to about 2 percent.

6. The disposable absorbent article of claim 1, wherein the fluid management layer has a basis weight of about 50 gsm to about 70 gsm.

7. The disposable absorbent article of claim 1, wherein the fluid management layer comprises about 15 percent to about 50 percent by weight absorbent fibers.

8. The disposable absorbent article of claim 1, wherein the fluid management layer comprises absorbent fibers of a linear density of about 1 dtex to about 7 dtex.

9. The disposable absorbent article of claim 1, wherein the fluid management layer comprises about 20 percent to about 60 percent by weight resilient fibers.

10. The disposable absorbent article of claim 1, wherein the fluid management layer comprises resilient fibers having a linear density of about 4 dtex to about 15 dtex.

11. The disposable absorbent article of claim 1, wherein the fluid management layer comprises about 30 percent to about 60 percent by weight stiffening fibers.

12. The disposable absorbent article of claim 1, wherein the fluid management layer comprises stiffening fibers of a linear density of about 1.0 dtex to about 6 dtex.

13. The disposable absorbent article of any of the preceding claims, wherein the fluid management layer is spunlaced.

14. The disposable absorbent article of claim 1, wherein the attenuated regions and the one or more built-up regions are visually discernible.

15. The disposable absorbent article of claim 1 wherein the topsheet has a surfactant applied to the absorbent-facing side such that the surfactant is present in a quantity greater on filaments proximate the absorbent-facing side than on filaments proximate the wearer-facing side.

16. The disposable absorbent article of claim 1 wherein a melt additive comprising a compound selected from the group consisting of erucamide, stearamide, oleamide, silicones, petroleum-based hydrocarbons having from about 4 to about 32 carbon atoms, fatty alcohols having from about 12 to about 24 carbon atoms, polysiloxane compounds, fatty acid esters, alkyl ethoxylates, fatty alcohol ethers having from about 12 to about 28 carbon atoms in their fatty chain, lanolin and its derivatives, glyceride derivatives including acetoglycerides and ethoxylated glycerides of C12-C28 fatty acids, fatty amides, and combinations thereof has been added to the fibers or filaments of the topsheet.

17. The disposable absorbent article of claim 1 wherein the second average basis weight differs from the first average basis weight by at least a factor of 2.

* * * * *